United States Patent
Grubbs et al.

(10) Patent No.: US 9,309,269 B2
(45) Date of Patent: Apr. 12, 2016

(54) TRANSITION-METAL-FREE SILYLATION OF AROMATIC COMPOUNDS

(71) Applicant: CALIFORNIA INSTITUTE OF TECHNOLOGY, Pasadena, CA (US)

(72) Inventors: Robert H. Grubbs, South Pasadena, CA (US); Alexey Fedorov, Zurich (CH); Anton Toutov, Pasadena, CA (US); Kerry Betz, Boulder, CO (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 14/628,641

(22) Filed: Feb. 23, 2015

(65) Prior Publication Data
US 2015/0166579 A1    Jun. 18, 2015

Related U.S. Application Data

(62) Division of application No. 14/043,929, filed on Oct. 2, 2013, now Pat. No. 9,000,167.

(60) Provisional application No. 61/708,931, filed on Oct. 2, 2012, provisional application No. 61/818,573, filed on May 2, 2013, provisional application No. 61/865,870, filed on Aug. 14, 2013.

(51) Int. Cl.
C07F 7/08    (2006.01)

(52) U.S. Cl.
CPC ............ *C07F 7/0829* (2013.01); *C07F 7/0812* (2013.01); *C07F 7/0814* (2013.01); *C07F 7/0816* (2013.01); *C07F 7/0818* (2013.01); *C07F 7/0896* (2013.01)

(58) Field of Classification Search
None
See application file for complete search history.

(56) References Cited

U.S. PATENT DOCUMENTS

| | | |
|---|---|---|
| 4,360,686 A | 11/1982 | Wang et al. |
| 4,363,925 A | 12/1982 | Acker et al. |
| 5,516,908 A | 5/1996 | Freyne et al. |

OTHER PUBLICATIONS

Ball et al., "Gold-Catalyzed Direct Arylation", Science, Sep. 28, 2012, vol. 337, 1644-1648.
Bekele et al., "Improved Synthesis of the Boc and Fmoc Derivatives of 4-(2'-Aminoethyl)-6-dibenzofuranpropionic Acid: An Unnatural Amino Acid That Nucleates β-Sheet Folding", Journal of Organic Chemistry, 1997, 62, 2259-2262.
Cheve et al., "De novo Design, synthesis and pharmacological evaluation of new azaindole derivatives as dual inhibitors of Abl and Src kinases", MedChemComm, 2012, 3, 7, 788-800.
Diez-Gonzalez et al. "Copper, Silver, and Gold Complexes in Hydrosilylation Reactions", Accounts of Chemical Research, vol. 41(2), Feb. 2008, pp. 349-358.
Häbich et al., "Preparation of Aryl- and Heteroaryltrimethylsilanes", Reviews, 1979, 841-876.
Kaur, et al, "(NHC) N-Heterocyclic Carbene) Complexes as Efficient Catalysts for the Reduction of Carbonyl Compounds", Organometallics, 2004, vol. 23, 1157-1160.
Konigs et al., "Base-Free Dehydrogenative Coupling of Enolizable Carbonyl Compounds with Silanes", Org. Lett., vol. 14(11), May 23, 2012, pp. 2842-2845.
Kuznetsov, et al, "General and Practical One-Pot Synthesis of Dihydrobenzosiloles from Styrenes", Org. Lett., Jan. 24, 2012, 14(3), pp. 914-917.
Park et al., "Transition Metal-Catlyzed Ortho-Functionalization in Organic Synthesis", Bull. Korean Chem. Soc., 2005, vol. 26, No. 6, 871-877.
Rychnovsky et al., "Synthesis of Optically Pure Arylsilylcarbinols and Their Use as Chiral Auxiliaries in Oxacarbenium Ion Reactions", Journal of Organic Chemistry, 2003, 68, 10135-10145.
Ulrich, et al., "Elektrophile Sillyberung Elektronenenreicher Heteroaromaten", Synthesis, Nov. 1984, 929-930.

*Primary Examiner* — Timothy R Rozof
(74) *Attorney, Agent, or Firm* — Baker & Hostetler LLP

(57) ABSTRACT

The present invention describes chemical systems and methods for silylating aromatic organic substrates, said system comprising a mixture of (a) at least one organosilane and (b) at least one strong base, said system being substantially free of a transition-metal compound, and said methods comprising contacting a quantity of the organic substrate with a mixture of (a) at least one organosilane and (b) at least one strong base, under conditions sufficient to silylate the aromatic substrate; wherein said system is substantially free of a transition-metal compound.

29 Claims, 22 Drawing Sheets

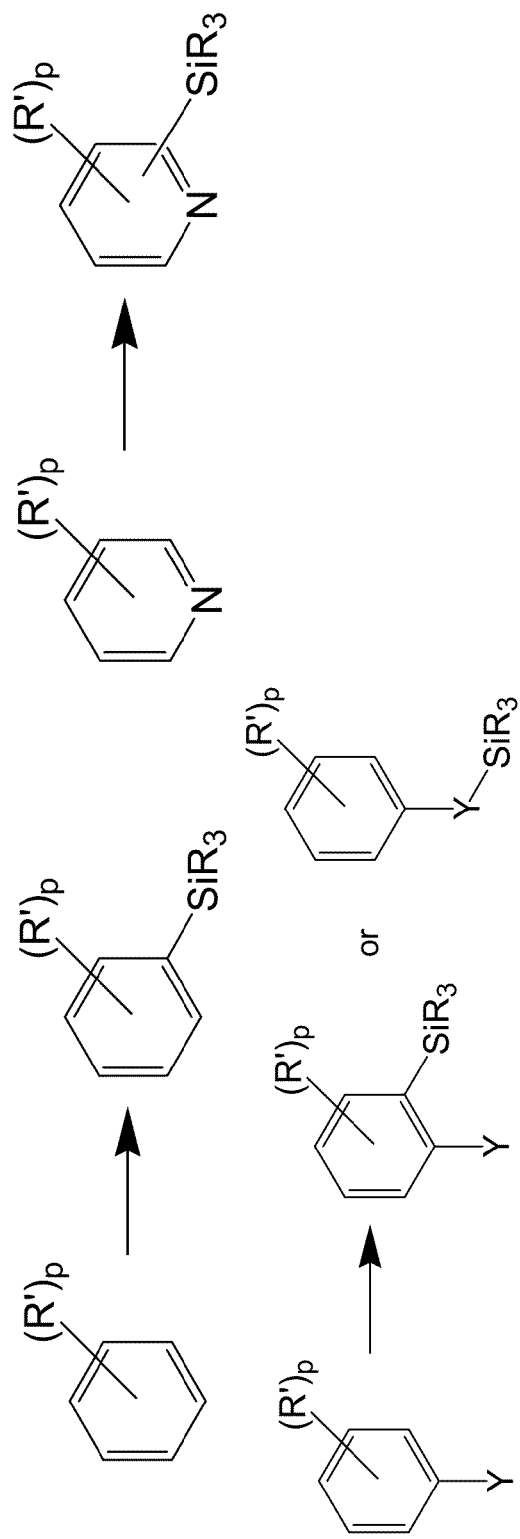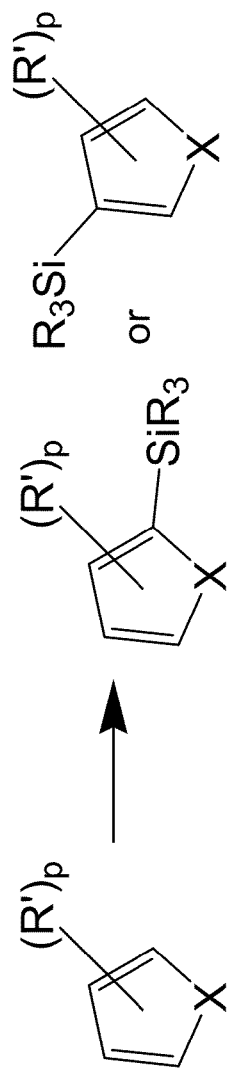
FIG. 1A
FIG. 1B

TRANSITION-METAL-FREE SILYLATION OF AROMATIC COMPOUNDS

CROSS REFERENCE TO RELATED APPLICATIONS

This application is a divisional to U.S. patent application Ser. No. 14/043,929, filed Oct. 2, 2013, which claims priority to U.S. Patent Application Ser. Nos. 61/708,931, filed Oct. 2, 2012, 61/818,573, filed May 2, 2013, and 61/865,870, filed Aug. 14, 2013, the contents of each of which is incorporated by reference in its entirety for all purposes.

TECHNICAL FIELD

The present invention is directed at methods for silylating substrates comprising aromatic moieties.

BACKGROUND

The ability to silylate organic moieties has attracted significant attention in recent years, owing to the utility of the silylated materials in their own rights, or as intermediates for other important materials used, for example, in agrichemical, pharmaceutical, and electronic material applications. Further, the ability to functionalize polynuclear aromatic compounds with organosilanes provides opportunities to take advantage of the interesting properties of these materials.

Historically, the silylation of aromatic compounds has been achieved via free radical processes involving thermally, photochemically, or by otherwise derived radical sources. Aromatic compounds are known react with silicon hydrides in the gas phase at 500-850° C., in the liquid phase under autogenous pressure at 350-500° C., in the presence of peroxides at 135° C. under gas phase condensations, and using electrical discharge reactions. Such reactions conditions are not amenable to non-volatile or thermally sensitive materials.

More recently, the transition metal mediated aromatic C—H silylation has been described, with different systems described based on, for example, Co, Rh, Ir, Fe, Ru, Os, Ni, Pd, and Pt catalysts. But for certain electronic applications, the presence of even low levels of such residues can adversely affect the performance of the silylated materials. Similarly, in certain pharmaceutical applications, limits on residual transition metals are fairly strict, and the ability to avoid them entirely offers benefits during post-synthesis work-up.

The present invention takes advantage of the discoveries cited herein to avoid at least some of the problems associated with previously known methods.

SUMMARY

Various embodiments of the present invention provide chemical systems for silylating organic compounds, each system comprising a mixture of (a) at least one organosilane and (b) at least one strong base, said system being substantially free of a transition-metal compound.

Other embodiments provide methods, each method comprising contacting an organic substrate comprising an aromatic moiety with a mixture of (a) at least one organosilane and (b) at least one strong base, under conditions sufficient to silylate the substrate; wherein said mixture and substrate are substantially free of a transition-metal compound.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings:

FIGS. 1A and 1B illustrate examples of some of the reactions available by the methods described herein.

FIG. 2-15 are $^1$H and $^{13}$C-NMR spectra or HSQC spectra of some of the compounds prepared by the methods described herein. Unless otherwise states, spectra were taken for compounds dissolved in CDCl$_3$ at 300 MHz ($^1$H) and 126 MHz ($^{13}$C). Peaks marked with asterisks are deemed to be associated with impurities in the respective sample.

FIG. 2 are (A) $^1$H and (B) $^{13}$C-NMR spectra of toluene and its triethylsilylation products.

FIG. 3 are (A) $^1$H and (B) $^{13}$C-NMR spectra of mesitylene and its triethylsilylation product.

FIG. 4 are (A) $^1$H and (B) $^{13}$C-NMR spectra of o-triethylsilyldiphenyl ether.

FIG. 5 are the HSQC spectra of (A) 2-methoxynaphthalene and (B) the product of its reaction with triethylsilane, as described in Example 6.7.2; characterized as triethyl-(3-methoxynaphthalen-2-yl)silane.

FIG. 7 are the HSQC spectra of (A) thioanisole (B) the product of its reaction with triethylsilane, as described in Example 6.7.4.

FIG. 8 is the HSQC spectra of the reaction product of N-methylindole with triethylsilane, as described in Example 6.9.1, characterized as 1-methyl-2-(triethylsilyl)-1H-indole FIG. 9 is the HSQC spectra of the reaction product of N-methylindole with triethylsilane, as described in Example 6.9.2, characterized as 1-methyl-3-(triethylsilyl)-1H-indole.

FIG. 10 is the HSQC spectra of the reaction product of 1-methyl-1H-pyrrolo[2,3-b]pyridine with triethylsilane, as described in Example 6.9.6, characterized as 1-methyl-2-(triethylsilyl)-1H-pyrrolo[2,3-b]pyridine.

FIG. 11 is the HSQC spectra of the reaction product of 1,2-dimethylmethylindole with triethylsilane, as described in Example 6.9.8.

FIG. 12 is the HSQC spectra of the reaction product of 1-phenylpyrrole with triethylsilane, as described in Example 6.9.10, characterized as 9,9-diethyl-9H-benzo[d]pyrrolo[1,2-a][1,3]azasilole.

FIG. 13 is the HSQC spectra of the reaction product of benzofuran with triethylsilane, as described in Example 6.9.11, characterized as benzofuran-2-yltriethylsilane.

FIG. 15 is the HSQC spectra of the reaction product of dibenzothiophene with triethylsilane, as described in Example 6.9.14, characterized as 4-(triethylsilyl)dibenzothiophene.

DETAILED DESCRIPTION OF ILLUSTRATIVE EMBODIMENTS

Figure 2A:
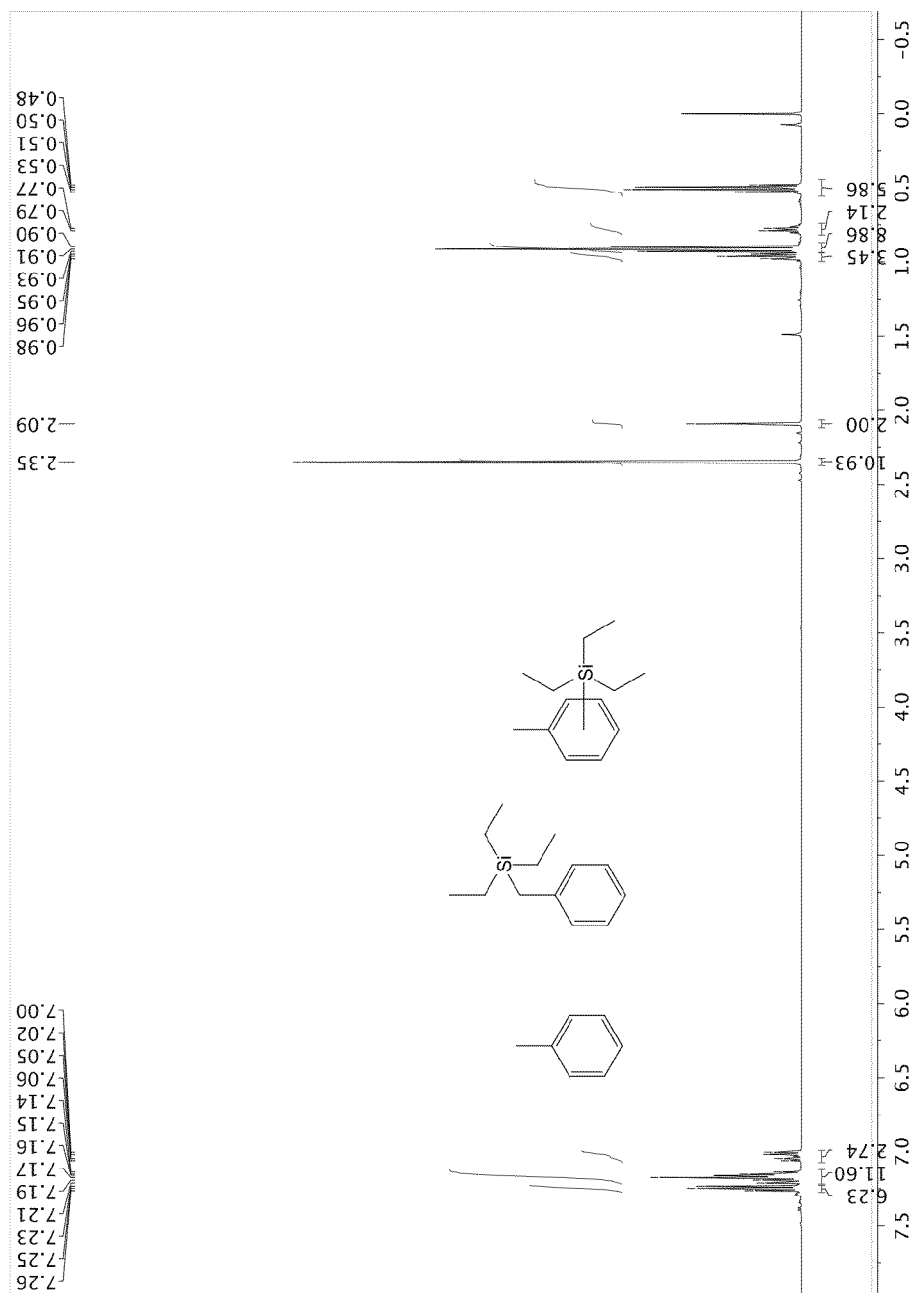

The present invention is founded on a set of reactions, each of which relies on simple mixtures of organosilanes and strong bases, which together form in situ systems (the structure and nature of the active species is yet unknown) able to silylate aromatic molecules in the liquid phase, without the presence of transition metal catalysts, UV radiation or electrical (including plasma) discharges. These reactions are relevant as an important advance in developing practical methods for the preparation of products important for pharmaceutical and electronics applications. Importantly this reaction is of great interest since it produces only environmentally benign silicates as the byproduct and avoids toxic metal waste streams as would be observed with nearly all other approaches proposed in the literature towards this end. The remarkable facility and regiospecificity exhibited by at least some of these systems provides a useful tool in the kit of chemists in these fields.

The present invention may be understood more readily by reference to the following description taken in connection with the accompanying Figures and Examples, all of which form a part of this disclosure. It is to be understood that this invention is not limited to the specific products, methods, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer to compositions and methods of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of." For those embodiments provided in terms of "consisting essentially of," the basic and novel characteristic(s) is the facile operability of the methods (or the systems used in such methods or the compositions derived therefrom) to silylate aromatic organic moieties.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Throughout this specification, words are to be afforded their normal meaning, as would be understood by those skilled in the relevant art. However, so as to avoid misunderstanding, the meanings of certain terms will be specifically defined or clarified.

The term "alkyl" as used herein refers to a linear, branched, or cyclic saturated hydrocarbon group typically although not necessarily containing 1 to about 24 carbon atoms, preferably 1 to about 12 carbon atoms, such as methyl, ethyl, n-propyl, isopropyl, n-butyl, isobutyl, tert-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl groups substituted with one or more substituent groups, and the terms "heteroatom-containing alkyl" and "heteroalkyl" refer to alkyl groups in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl groups, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl groups substituted with one or more substituent groups, and the terms "heteroatom-containing alkenyl" and "heteroalkenyl" refer to alkenyl groups in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl groups, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term "substituted alkynyl" refers to an alkynyl group substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include a linear, branched, unsubstituted, substituted, and/or heteroatom-containing alkynyl and lower alkynyl group, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aromatic" refers to the ring moieties which satisfy the Hückel 4n+2 rule for aromaticity, and includes both aryl (i.e., carbocyclic) and heteroaryl (also called heteroaromatic) structures, including aryl, aralkyl, alkaryl, heteroaryl, heteroaralkyl, or alk-heteroaryl moieties, or oligomeric or polymeric analogs thereof.

The term "aryl" as used herein, and unless otherwise specified, refers to an aromatic substituent or structure containing a single aromatic ring or multiple aromatic rings that are fused together, directly linked, or indirectly linked (such that the different aromatic rings are bound to a common group such as a methylene or ethylene moiety). Unless otherwise modified, the term "aryl" refers to carbocyclic structures. Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)— alkyl, —O(CO)-aryl, or —O(CO)-aralkyl, wherein "alkyl," "aryl, and "aralkyl" are as defined above.

The terms "cyclic" and "ring" refer to alicyclic or aromatic groups that may or may not be substituted and/or heteroatom-containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic. The term "acyclic" refers to a structure in which the double bond is not contained within a ring structure.

The terms "halo," "halide," and "halogen" are used in the conventional sense to refer to a chloro, bromo, fluoro, or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated, and unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms, and the term "hydrocarbylene" intends a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Non-limiting examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

As used herein, the terms "substrate" or "organic substrate" are intended to connote both discrete small molecules (sometimes described as "organic compounds") and oligomers and polymers containing such "aromatic moieties." The term "aromatic moieties" is intended to refer to those portions of the compounds, oligomers, or polymers having an indicated aromatic structures. Where shown as structures, the moieties contain at least that which is shown, as well as containing further functionalization, substituents, or both, including but not limited to the functionalization described as "Fn" herein.

By "substituted" as in "substituted hydrocarbyl," "substituted alkyl," "substituted aryl," and the like, as alluded to in some of the aforementioned definitions, is meant that in the hydrocarbyl, alkyl, aryl, heteroaryl, or other moiety, at least one hydrogen atom bound to a carbon (or other) atom is replaced with one or more non-hydrogen substituents. Examples of such substituents include, without limitation: functional groups referred to herein as "Fn," such as halo (e.g., F, Cl, Br, I), hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_1$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl ((CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO—), carbamoyl (—(CO)—NH_2), mono-($C_1$-$C_{24}$ alkyl)-substituted carbamoyl (—(CO)NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH ($C_1$-$C_{24}$ alkyl)), di-($C_1$-$C_{24}$ haloalkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl, thiocarbamoyl (—(CS)—NH_2), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_5$-$C_{24}$ aryl)substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), di-N—($C_1$-$C_{24}$ alkyl), N—($C_5$-$C_{24}$ aryl)-substituted thiocarbamoyl, carbamido (—NH—(CO)—NH_2), cyano(—C≡N), cyanato (—O—C≡N), thiocyanato (—S—C≡N), formyl (—(CO)—H), thioformyl (—(CS)—H), amino (—NH_2), mono-($C_1$-$C_{24}$ alkyl)-substituted amino, di-($C_1$-$C_{24}$ alkyl)-substituted amino, mono-($C_5$-$C_{24}$ aryl)substituted amino, di-($C_5$-$C_{24}$ aryl)-substituted amino, $C_1$-$C_{24}$ alkylamido (—NH—(CO)-alkyl), $C_6$-$C_{24}$ arylamido (—NH—(CO)-aryl), imino (—CR═NH where R=hydrogen, $C_1$-$C_{24}$ alkyl, C5-C24 aryl, $C_6$-$C_{24}$ alkaryl, $C_6$-$C_{24}$ aralkyl, etc.), $C_2$-$C_{20}$ alkylimino (—CR═N(alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR═N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO_2), nitroso (—NO), sulfo (—SO_2OH), sulfonate(SO_2O—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO_2-alkyl), $C_1$-$C_{24}$ monoalkylaminosulfonyl-SO_2—N(H) alkyl), $C_1$-$C_{24}$ dialkylaminosulfonyl-SO_2—N(alkyl)$_2$, $C_5$-$C_{24}$ arylsulfonyl (—SO_2-aryl), boryl (—BH_2), borono (—B(OH)_2), boronato (—B(OR)_2 where R is alkyl or other hydrocarbyl), phosphono (—P(O)(OH)_2), phosphonato (—P(O)(O)_2), phosphinato (P(O)(O—)), phospho (—PO_2), and phosphine (—PH_2); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably C2-C6 alkynyl), $C_5$-$C_{24}$ aryl (preferably $C_5$-$C_{24}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl). Within these substituent structures, the "alkyl," "alkylene," "alkenyl," "alkenylene," "alkynyl," "alkynylene," "alkoxy," "aromatic," "aryl," "aryloxy," "alkaryl," and "aralkyl" moieties may be optionally fluorinated or perfluorinated. Additionally, reference to alcohols, aldehydes, amines, carboxylic acids, ketones, or other similarly reactive functional groups also includes their protected analogs. For example, reference to hydroxy or alcohol also includes those substituents wherein the hydroxy is protected by acetyl (Ac), benzoyl (Bz), benzyl (Bn, Bnl), β-Methoxyethoxymethyl ether (MEM), dimethoxytrityl, [bis-(4-methoxyphenyl)phenylmethyl] (DMT), methoxymethyl ether (MOM), methoxytrityl[(4-methoxyphenyl) diphenylmethyl, MMT), p-methoxybenzyl ether (PMB), methylthiomethyl ether, pivaloyl (Piv), tetrahydropyranyl (THP), tetrahydrofuran (THF), trityl (triphenylmethyl, Tr), silyl ether (most popular ones include trimethylsilyl (TMS), tert-butyldimethylsilyl (TBDMS), tri-iso-propylsilyloxymethyl (TOM), and triisopropylsilyl (TIPS) ethers), ethoxyethyl ethers (EE). Reference to amines also includes those substituents wherein the amine is protected by a BOC glycine, carbobenzyloxy (Cbz), p-methoxybenzyl carbonyl (Moz or MeOZ), tert-butyloxy carbonyl (BOC), 9-fluorenylmethyloxycarbonyl (FMOC), acetyl (Ac), benzoyl (Bz), benzyl (Bn), carbamate, p-methoxybenzyl (PMB), 3,4-dimethoxybenzyl (DMPM), p-methoxyphenyl (PMP), tosyl (Ts) group, or sulfonamide (Nosyl & Nps) group. Reference to substituent containing a carbonyl group also includes those substituents wherein the carbonyl is protected by an acetal or ketal, acylal, or diathane group. Reference to substituent containing a carboxylic acid or carboxylate group also includes those substituents wherein the carboxylic acid or carboxylate group is protected by its methyl ester, benzyl ester, tert-butyl ester, an ester of 2,6-disubstituted phenol (e.g. 2,6-dimethylphenol, 2,6-diisopropylphenol, 2,6-di-tert-butylphenol), a silyl ester, an orthoester, or an oxazoline.

By "functionalized" as in "functionalized hydrocarbyl," "functionalized alkyl," "functionalized olefin," "functionalized cyclic olefin," and the like, is meant that in the hydrocarbyl, alkyl, aryl, heteroaryl, olefin, cyclic olefin, or other moiety, at least one hydrogen atom bound to a carbon (or other) atom is replaced with one or more functional groups such as those described herein and above. The term "functional group" is meant to include any functional species that is suitable for the uses described herein. In particular, as used herein, a functional group would necessarily possess the ability to react with or bond to corresponding functional groups on a substrate surface.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

As used herein, the term "silylating" refers to the forming of carbon-silicon bonds, generally in a position previously occupied by a carbon-hydrogen bond, generally a non-activated C—H bond. The ability to replace directly a C—H bond with a C—Si bond, under the conditions described herein, is believed to be unprecedented.

The present invention includes embodiments related chemical systems and methods for silylating aromatic compounds and aromatic moieties. Specific embodiments provide chemical systems for silylating aromatic compounds and aromatic moieties, each system comprising a mixture of (a) at least one organosilane and (b) at least one strong base, said system being preferably substantially free of a transition-metal compound.

It is recognized that the systems and reactions which provide for the silylation of aromatic compounds and aromatic moieties, under different conditions (mainly at higher temperatures), are also capable of cleaving C—O, C—N, C—S bonds within aromatic substrates. This latter reductive cleavage feature is the subject of a co-filed and co-pending U.S. patent application Ser. No. 14/043,917, entitled "Transition-Metal-Free Reductive Cleavage of Aromatic C—O, C—N, and C—S Bonds by Activated Silanes" which is also incorporated by reference in its entirety for all purposes. The mechanism by which the system and methods operate is not yet understood, for example, whether the silylation is an intermediate step or a co-product or by-product of the cleavage reactions (certain observations suggest not), but it does appear that the relative contribution of each manifold can be manipulated by the reaction conditions. For example, other factors being similar or equal and with certain exceptions, it appears that higher temperatures and longer reaction times tend favor the cleavage of C—O, C—N, C—S bonds over the silylation reactions (which occur at relatively milder temperatures). Similarly, absence of hydrogen and hydrogen donor molecules (even at the higher temperatures) and use of substoichiometric quantities of the strong base (relative to the organosilane) appear to favor the silylation reactions and disfavor the C—X cleavages.

As used herein, the term "substantially free of a transition-metal compound" is intended to reflect that the system is effective for its intended purpose of silylating aromatic compounds and aromatic moieties under the relatively mild conditions described herein, even in the absence of any exogenous (i.e., deliberately added or otherwise) transition-metal catalyst(s). While certain embodiments provide that transition metals, including those capable of catalyzing silylation reactions, may be present within the systems or methods described herein at levels normally associated with such catalytic activity, the presence of such metals (either as catalysts or spectator compounds) is not required and in many cases is not desirable. As such, in preferred embodiments, the system and methods are "substantially free of transition-metal compounds." Unless otherwise stated, then, the term "substantially free of a transition-metal compound" is defined to reflect that the total level of transition metal within the silylating system, independently or in the presence of organic substrate, is less than about 50 ppm, as measured by ICP-MS as described in Example 2 below. Additional embodiments also provide that the concentration of transition metals is less than about 100 ppm, 50 ppm, 30 ppm, 25 ppm, 20 ppm, 15 ppm, 10 ppm, or 5 ppm to about 1 ppm or 0 ppm. As used herein, the term "transition metal" is defined to include Co, Rh, Ir, Fe, Ru, Os, Ni, Pd, Pt, Cu, or combinations thereof. In further specific independent embodiments, the concentration of Ni, as measured by ICP-MS, is less than 25 ppm, less than 10 ppm, less than 5 ppm, or less than 1 ppm.

These systems typically comprise hydrocarbon or ether-based solvents. As described herein, solvents such as benzene, toluene, mesitylene, and tetrahydrofurans (including 2-methyltetrahydrofuran) have been shown to work well.

While it may not be necessary to limit the system's exposure to water and oxygen, in some embodiments, the chemical system and the methods are done in an environment substantially free of water, oxygen, or both water and oxygen. Unless otherwise specified, the term "substantially free of water" refers to levels of water less than about 500 ppm and "substantially free of oxygen" refers to oxygen levels corresponding to partial pressures less than 1 torr. Where stated, additional independent embodiments may provide that "substantially free of water" refers to levels of water less than 1.5%, 1%, 0.5%, 1000 ppm, 500 ppm, 250 ppm, 100 ppm, 50 ppm, 10 ppm, or 1 ppm and "substantially free of oxygen" refers to oxygen levels corresponding to partial pressures less than 50 torr, 10 torr, 5 torr, 1 torr, 500 millitorr, 250 millitorr, 100 millitorr, 50 millitorr, or 10 millitorr.

As used herein to describe the systems and methods, the term "organosilane" refers to a compound or reagent having at least one silicon-hydrogen (Si—H) bond. The organosilane may further contain a silicon-carbon, a silicon-oxygen, a silicon-nitrogen bond, or a combination thereof, and may be monomeric, or contained within an oligomeric or polymeric framework, including being tethered to a heterogeneous or homogeneous support structure. In certain embodiments, these organosilane may comprise at least one compound of Formula (I) or Formula (II):

$$(R)_{4-m}Si(H)_m \quad (I)$$

$$R\text{—}[\text{—}SiH(R)\text{—}O\text{—}]_nR \quad (II)$$

where:
m is 1, 2, or 3, preferably 1;
n is in a range of from about 5 to about 500, from about 10 to about 100 or from about 25 to about 50; and
each R is independently optionally substituted $C_{1-12}$ alkyl or heteroalkyl, optionally substituted $C_{5-20}$ aryl or heteroaryl, optionally substituted $C_{6-30}$ alkaryl or heteroalkaryl, optionally substituted $C_{6-30}$ aralkyl or heteroaralkyl, optionally substituted —O—$C_{1-12}$ alkyl or heteroalkyl, optionally substituted —O—$C_{5-20}$ aryl or heteroaryl, optionally substituted —O—$C_{6-30}$ alkaryl or heteroalkaryl, or optionally substituted —O—$C_{6-30}$ aralkyl or heteroaralkyl, and, if substituted, the substituents may be phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents may optionally provide a tether to an insoluble or sparingly soluble support media comprising alumina, silica, or carbon. Exemplary, non-limiting organosilanes include $(R)_3SiH$, where R is $C_{1-6}$ alkyl, particularly triethylsilane and tributylsilane, mixed aryl alkyl silanes, such as $PhMe_2SiH$, and polymeric materials, such as polymethylhydrosiloxane (PMHS).

As used herein, the term "strong base" refers to a compound having a strong affinity for hydrogen atoms especially, but not only, in non-aqueous media. In specific independent embodiments, the at least one strong base comprises an alkali or alkaline earth metal hydride or alkoxide. It should be appreciated, then, that this definition is not strictly limited to the classic conjugate acid-base model—since the conjugate acid of hydride would be dihydrogen. One measure of this "strong affinity" may be that the strong base, if reacted with water, would react to the practically complete formation of hydroxide therefrom. Other "strong bases" may be considered as including alkyl lithium compounds or amide ions, for example potassium bis(trimethylsilyl)amide.

There appears to be a hierarchy of activity related to the counterion of the strong base, such that the use of cesium and potassium hydrides and alkoxides are preferred. Exemplary hydrides useful in the present invention include calcium hydride and potassium hydride. Similarly, the effect of temperature on the effectiveness of reaction with hydrides may be seen in Example 6.5, Table 2, entries 13 and 24, where the reaction of dibenzofuran with KH conducted at 100° C. results in relatively high silylation rates, and low levels of formation of the mono-cleaved product, biphenyl-2-ol, whereas conducting a similar experiment at 165° C. resulted in essentially quantitative conversion to predominantly the biphenyl-2-ol product.

Useful alkoxides include those comprising a $C_{1-12}$ linear or branched alkyl moietird or a $C_{5-10}$ aromatic or heteroaromatic moieties, for examples methoxide, ethoxide, propoxide, butoxide, 2-ethyl-hexyloxide, or benzyloxide. Each of these appears to give comparable reactivity (see, e.g., Example 6.5, Table 2, compare Entries 17, 25-26, and 28). Further, the choice of the counter cation also impacts the effectiveness of the activity of the chemical system, such that potassium or cesium alkoxides are preferred. More specifically, potassium methoxide, ethoxide, and tert-butoxide and cesium 2-ethyl-hexyl alkoxide have been shown to be particularly effective in this role. By comparison, the reaction of $Et_3SiH$ with lithium or sodium tert-butoxide provides no silylation of dibenzofuran (see, e.g., Example 6.5, Table 2, Entries 29-31) suggesting that the counter ion plays a critical role in the generation of the active silylating species and, possibly, in activation of the substrate ether, or both. Similarly, conducting reactions with potassium tert-butoxide in the presence of sufficient 18-crown-6 to act as a potassium chelator resulted in nearly complete inhibition of the reaction.

While the relative amounts of organosilane and strong base is not believed to be particularly important, so long as both are present in sufficient quantities, in certain embodiments, the organosilane and the at least one strong base are present together at a molar ratio, with respect to one another, in a range of from about 20:1 to about 1:1. In other embodiments, these ratios may be on the order of about 5:1 to about 1:1, from about 3:1 to about 1:1, or from about 3:2 to about 1:1. The silylation reactions appear also to favor those conditions where the base is sub-stoichiometric, 0.01:1 to 0.9:1, with respect to the substrate, especially for more active systems. Further embodiments provide that the base is present with respect to the substrate at a ratio of from about 0.01:1 to about 0.6, or from about 0.1:1 to about 0.6.

Further embodiments provide systems further comprising N-based compounds (preferably N-based chelants) including, for example, optionally substituted tetraalkylethylenediamine (e.g., tetramethylethylenediamine), optionally substituted 1,10-phenanthroline derivatives, optionally substituted 2,2'-bipyridine derivatives, and optionally substituted 4-dimethylaminopyridine derivatives. See, e.g., Example 6.9.6 and Table 4.

To this point, the invention has been described in terms of the chemical system capable of silylating aromatic compounds or moieties, but it should also be apparent that the invention also includes the methods of carrying out these transformations. That is, various additional embodiments include those methods where an organic substrate comprising an aromatic moiety is contacted with any of the chemical systems described above under conditions sufficient to silylate at least a portion of the substrate. That is, certain embodiments provide methods, each method comprising contacting an organic substrate comprising an aromatic moiety with a mixture of (a) at least one organosilane and (b) at least one strong base, under conditions sufficient to silylate the substrate; wherein said mixture and substrate are substantially free of a transition-metal compound. These embodiments are generally done in the liquid phase, without UV irradiation or electric or plasma discharge conditions.

In some embodiments, the conditions sufficient to silylate the organic substrate comprise heating the substrate with a mixture of (a) the at least one organosilane and (b) the at least one strong base at a temperature in a range of about 10° C. to about 165° C. In some cases, the temperatures may be applied in a range of from about 20° C., about 30° C., about 40° C., about 50° C., about 60° C., or about 80° C. to about 165° C., about 150° C., about 125° C., about 100° C., or to about 80° C. Any of the temperatures described in the Examples may be considered independent embodiments. Typical operating reaction times may range from about 2 hours, from about 4 hours, from about 6 hours, or from about 10 hours to about 28 days, to about 14 days, to about 7 days, to about 4 days, to about 3 days, to about 48 hours, to about 24 hours, to about 12 hours, or to about 6 hours.

As described above, those features described as relevant for the chemical systems for silylating aromatic compounds and aromatic moieties are also relevant for the methods of silylating these aromatic compounds and aromatic moieties. For example, in various embodiments, the methods provide that the system is substantially free of water, oxygen, or both water and oxygen.

In other embodiments, at least one organosilane comprises an organosilane of Formula (I) or Formula (II):

$$(R)_{4-m}Si(H)_m \qquad (I)$$

$$R-[-SiH(R)-O-]_n R \qquad (II)$$

where
m is 1, 2, or 3 (preferably 1);
n is 10 to 100; and each R is independently optionally substituted $C_{1-12}$ alkyl or heteroalkyl, optionally substituted $C_{5-20}$ aryl or heteroaryl, optionally substituted $C_{6-30}$ alkaryl or heteroalkaryl, optionally substituted $C_{6-30}$ aralkyl or heteroaralkyl, optionally substituted —O—$C_{1-12}$ alkyl or heteroalkyl, optionally substituted —O—$C_{5-20}$ aryl or heteroaryl, optionally substituted —O—$C_{6-30}$ alkaryl or heteroalkaryl, or optionally substituted —O—$C_{6-30}$ aralkyl or heteroaralkyl, and, if substituted, the substituents may be phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents may optionally provide a tether to an insoluble or sparingly soluble support media comprising alumina, silica, or carbon.

In still other embodiments, the organosilane is $(R)_3SiH$, where R is independently $C_{1-6}$ alkyl, preferably $Et_3SiH$ or $Et_2MeSiH$. The at least one strong base may comprise an alkali or alkaline earth metal hydride, as described above, for example, calcium hydride or potassium hydride. The at least one strong base may comprise an alkali or alkaline earth metal alkoxide, as described above, for example, where the at least one alkoxide comprises a $C_{1-12}$ linear or branched alkyl moiety or a $C_{5-10}$ aryl or heteroaryl moiety, preferably methoxide, ethoxide, propoxide, butoxide, or 2-ethyl-hexyl alkoxide. The alkali metal cation is preferably potassium or cesium. In most preferred embodiments, the organosilane is triethylsilane, trimethyl silane, diethylmethylsilane, diethylsilane, dimethylsilane, dimethylethylsilane, ethyldimethylsilane, dimethylphenylsilane, diethylphenylsilane and the strong base is potassium tert-butoxide. Other combinations or exemplified reactants provide additional embodiments in this regard.

In certain embodiments, the organosilane (or monomer equivalent) and the at least one strong base are present together at a molar ratio, with respect to one another, in a range of from about 20:1 to about 1:1. In certain embodiments the at least one strong base and organic substrate are present together at a molar ratio, with respect to one another, in a range of from about 0.01:1 to about 5:1 But preferably the base is sub-stoichiometric—i.e., in a ratio of 0.01:1 to 0.9:1—with respect to the organic substrate. That is, the methods may be considered to be catalytic with respect to the strong base.

Additionally, in the context of the methods, the term "substantially free of a transition-metal compound" carries the same connotations and related embodiments as described supra for the chemical system; i.e., reflecting that the methods are effectively conducted in the absence of any deliberately added transition-metal catalyst(s). Unless otherwise stated, when describing a method or system, the term is defined to reflect that the total level of transition metal, as measured by ICP-MS as described in Example 2 below, is less than about 50 ppm. Additional embodiments also provide that the concentration of transition metals is less than about 100 ppm, 50 ppm, 30 ppm, 25 ppm, 20 ppm, 15 ppm, 10 ppm, or 5 ppm to about 1 ppm or 0 ppm, relative to the weight of the total system (i.e., both respect to the silylation system and the silylation system and the organic substrate). As used herein, the term "transition metal" is defined to mean Co, Rh, Ir, Fe, Ru, Os, Ni, Pd, Pt, Cu, or combinations thereof. In further independent embodiments, the concentration of Ni, as measured by ICP-MS, is less than 25 ppm, less than 10 ppm, less than 5 ppm, or less than 1 ppm. Noting here that certain embodiments of the chemical system may comprise the at least one organosilane, and strong base, it should be appreciated that independent embodiments provide that the levels of transition metals are maintained below the levels just described, when considering each of these mixture combinations.

Further embodiments provide that the methods further comprise using sub-stoichiometric amounts (relative to the substrate) of N-based compounds including (preferably N-based chelants), for example, optionally substituted tetraalkylethylenediamine (e.g., tetramethylethylenediamine), optionally substituted 1,7-phenanthroline derivatives, optionally substituted 1,10-phenanthroline derivatives, optionally substituted 2,2'-bipyridine derivatives, and optionally substituted 4-dimethylaminopyridine derivatives. See, e.g., Example 6.9.6.

The methods are fairly flexible with respect to substrates, and accommodate both those containing both aryl and heteroaryl moieties. Exemplary substrates comprising aryl moieties include those comprising optionally substituted benzene (including mesitylene and toluene), biphenyl, naphthalene, anthracene, or higher polyaromatic ring structures. These pure hydrocarbon substrates generally require more forcing conditions to silylate the ring carbons than do heteroaryl systems. See Example 6.4. Nevertheless, the ability to functionalize these hydrocarbon ring structures is an important feature of these methods and systems.

Where the aryl or heteroaryl moiety comprises an alpha-methyl or methylene C—H bond, as in an optionally substituted $C_{1-6}$ alkyl group (as exemplified by methyl groups of toluene, mesitylene, 1,2 dimethylindole, or 2,5-dimethylthiophene in the Examples), it appears that the reaction proceeds to form alpha silanes at temperatures lowered than required to silylate the ring carbons. As used herein, the term "alpha carbon" refers to the first carbon positioned exocyclic to the aromatic moeity, and "alpha" as in "alpha methyl or methylene" is intended to refer to the methyl or methylene on the first exocyckic carbon directly attached to the aromatic ring. The term "alpha silane" refers a silane bonded to the alpha carbon. The term "alpha" is considered to encompass benzylic carbons for 6 membered aryl aromatics. Methods resulting in such silylations are within the scope of the present invention.

Other exocyclic ring substituents, including those having an exocyclic aromatic C—X bond, generally react according to the methods described herein. The term "exocyclic" refers to the position of the O, N, or S with respect to the aromatic ring system. For example, the term "exocyclic" refers to a bond in which the carbon is contained within the aromatic rings system, but the respective oxygen, nitrogen, or sulfur atoms are not and, (in the case of nitrogen), vice versa. For example, phenol, dimethylaniline, 1-methyl-1H-pyrrole, and benzenethiol contain exocyclic aromatic C—O, C—N, and C—S bonds, respectively. Exemplary organic substrates comprise, but are not limited to, optionally substituted phenyl ethers, phenyl amines, phenyl sulfides, naphthyl ethers, naphthyl amines, or naphthyl sulfides moiety, N-alkyl or N-aryl pyrroles, or combinations thereof.

Where X is O or N, the reaction favors silylation of the ring ortho or at the carbon adjacent to the carbon containing the exocyclic C—X bond. Electron-rich systems or electron-donating groups or substituents appear to be generally more reactive than electron-poor systems or electron-withdrawing groups or substituents; the latter may require more forcing conditions than the former, but note that more forcing conditions derived from higher temperatures may result in driving the C—X cleavage manifold—see, for example co-filed U.S. patent application Ser. No. 14/043,917, filed Oct. 2, 2013, entitled "Transition-Metal-Free Reductive Cleavage of Aromatic C—O, C—N, and C—S Bonds by Activated Silanes." Anisole and 2-methoxynaphthalene show a particular preference to the ortho position, and this selectivity provides the basis for embodiments comprising the selective ortho silylation of such substrates. See, e.g., Examples 6.4 and 6.7. Interesting, and by contrast, those substrates having an exocyclic aromatic C—X bond, where X is S-alkyl provides a different reactivity, showing a proclivity to silylate the alkyl group rather than the aromatic ring system. See, e.g., Example 6.7.4. This reactivity pattern provides a basis for those embodiments comprising the β-silylation of such substrates.

In certain embodiments, the methods are applied to an organic substrate comprising a heteroaryl moiety. Non-limiting heteroaryl moieties include those comprising an optionally substituted furan, pyrrole, thiophene, pyrazole, imidazole, triazole, isoxazole, oxazole, thiazole, isothiazole, oxadiazole, pyridine, pyridazine, pyrimidine, pyrazine, triazone, benzofuran, benzopyrrole, benzothiophene, isobenzofuran, isobenzopyrrole, isobenzothiophene, indole, isoindole, indolizine, indazole, azaindole, benzisoxazole, benzoxazole, quinoline, isoquinoline, cinnoline, quinazoline, naphthyridine, 2,3-dihydrobenzofuran, 2,3-dihydrobenzopyrrole, 2,3-dihydrobenzothiophene, dibenzofuran, xanthene, dibenzopyrol, dibenzothiophene. In more preferred embodiments, the substrate comprises a moiety comprising an optionally substituted furan, pyrrole, thiophene, pyrazole, imidazole, benzofuran, benzopyrrole, benzothiophene, indole, azaindole dibenzofuran, xanthene, dibenzopyrrole, or dibenzothiophene moiety. Independent embodiments provide that the methods yield silylated products substituted as described herein.

In other specific embodiments, the methods are operable on substrates comprising the following moieties:

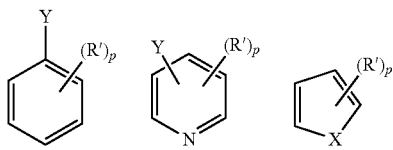

where

X is N—R", O, or S;

Y is H, N(R")$_2$, O—R", or S—R"

p is 0 to 4, 0 to 3, 0 to 2, or 0 to 1;

R' is a functional group "Fn," as described above, or (R')$_p$ is a fused alicyclic, heteroalicyclic, aryl or heteroaryl moiety; and R" is an amine protecting group or an optionally substituted alkyl, aryl, heteroaryl, alkaryl or alk-heteroaryl, preferably optionally substituted $C_1$-$C_6$ alkyl, phenyl, tolyl, benzyl, or phenethyl.

In certain more specific embodiments, the methods are operable on organic substrates comprising the following moieties:

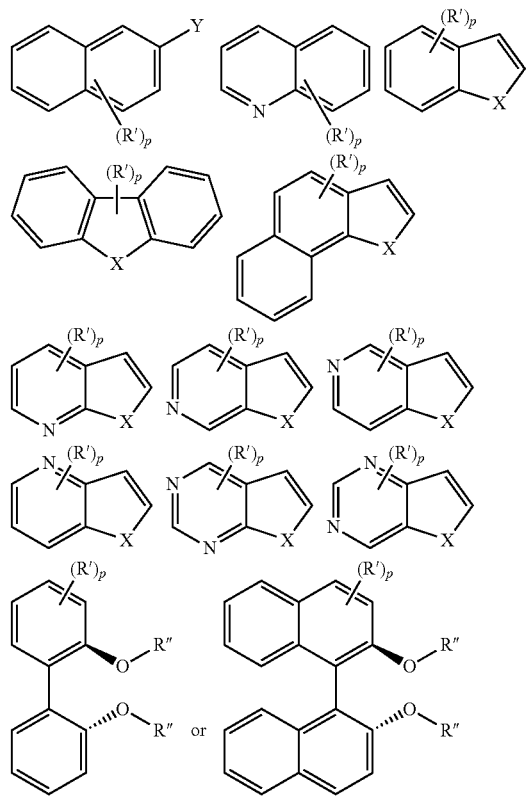

where X, Y, R', R" and p are as defined above. Note that the designation in each case, is intended to allow for substitution on either aromatic ring.

Heteroaryl moieties appear to react according to the inventive methods under conditions that are milder than their aryl cogeners, such that, in mixed aryl-heteroaryl systems, reactions generally proceed to silylate the heteroaryl ring preferentially. For example, as shown in Examples 6.9.1 to 6.9.7 and 6.9.11 to 6.9.13, silylation is shown to occur preferentially in the heterocylic portion of the molecule. However, and as shown in Example 6.9.9, where an aryl moiety is proximately positioned to a (presumed first) silylated heteroaryl, the silylation of that aryl moiety occurs at much milder conditions than those required for the aryl-only system (cf. Examples 6.7.3 and 6.9.10). This ability to form silylated ring structures from heteroaryl precursors, is another useful feature and embodiment of the present inventions.

Also, 5-membered heteroaryl moieties appear to react according to the inventive methods under conditions that are milder than even 6-membered heteroaryl moieties. For example, as shown in Example 6.9.6, N-methyazalindole is shown to silylate preferentially in the 5-membered heterocylic portion of the molecule. And both rings silylate under conditions much milder than found for pyridine.

The silylation reactions with substrates comprising 5-membered heteroaryl moieties also provide remarkably clean and apparently tunable regioselectivities. Substrates comprising 5-membered heteroaryl rings containing O or N can silylate at the C-2 or C-3 position, depending on time and temperature. While not intending to be bound by the correctness or incorrectness of any particular theory, it appears that silylation at the C-2 position represents the kinetic result of the reaction, whereas silylation at the C-3 position is thermodynamically favored. Interesting, substrates comprising 5-membered heteroaryl rings containing S appears to proceed directly and preferentially to the C-3 position. While described in terms of "kinetic" and "thermodynamic" pathways, it is not clear that silylation at a C-3 position necessarily proceeds through a C-2 intermediate. Indeed, experiments using 1,2 dimethyl indole and 2,5-dimethyl thiophene, where the C-2 positions are blocked by methyl groups, reaction proceeded to silylate the alpha-methyl group preferentially, with no evidence for silylation in the C-3 position.

Unless otherwise stated, reference to silylation at a specific position is intended to connote a regioselectivity or regiospecificity of a product at that position of greater than about 80%. But other embodiments provide that the regiospecificity at that position is greater than about 50%, greater than about 75%, greater than about 90%, or greater than about 95%.

The products of the inventive methods are useful in a range of agrichemical, pharmaceutical, and electronics applications, as described infra. They also provide useful intermediates for subsequent syntheses. The use of aromatic silanes, such as those described herein, are useful synthons for the preparation of biaryl/biaromatic compounds, for example, using the Hiyama coupling methods generally recognized in the art. The skilled artisan would be well able to combine the teachings of these Hiyama coupling methods with those presented here, without undue experimentation, to prepare biaryl/biaromatic compounds, and such preparations are considered within the scope of the present invention. Also, Ball and colleagues (Ball et al., Science 28 Sep. 2012: Vol. 337 no. 6102 pp. 1644-1648, which is incorporated by reference herein for its teaching of the catalysts, methods, and substrates) have more recently described another method, using gold catalysts, to couple trialkyl silanes, such as those described herein, to form biaryl/biaromatic compounds. Again, the skilled artisan would be well able to combine the teachings of the Ball coupling, including at least the second aryl compounds taught or suggested in the Ball reference, again without undue experimentation, to prepare biaryl compounds, and such methods and preparations are considered within the scope of the present invention. In such embodiments, a silylated product of the present invention, whether isolated or generated in situ, is further reacted under conditions (including the presence of a suitable transition metal catalyst) sufficient to couple the silylated product with a second aromatic compound to prepare the biaryl product. As intended herein, the second aromatic compound comprises an optionally substituted aromatic moiety, including optionally substituted aryl and heteroaryl moieties, where the terms "optionally substituted," "aromatic," "aryl," and "heteroaryl" carry the same definitions as already described herein.

The conversion of aromatic silanes, such as those described herein, are also known to be convertible to aromatic hydroxy compounds, using the well-known Fleming-Tamao oxidation methods. The skilled artisan would be well able to combine the teachings of these Fleming-Tamao oxidations with those presented here, again without undue experimentation, to prepare hydroxylated aromatic compounds, and such methods and preparations are considered within the scope of the present invention. In such embodiments, the aromatic silylated products of the present invention, whether isolated or generated in situ, are further reacted under conditions (including the presence of a suitable transition metal catalyst) sufficient to convert the silylated product to hydroxylated aromatic products.

Also, the ability of the present invention to silylate alpha-carbon substituents (or β-silyl groups in the case of exocyclic sulfur) also provides that those products may be used as synthons for the Peterson olefination reaction. The known ease of deprotonating the alpha-methylene proton, when adjacent to the silane silicon (the "alpha silicon effect") to yield an alpha-silyl carbanion can form a convenient precursor for this olefination reaction. The skilled artisan would be well able to combine the teachings of these Peterson olefination reaction with those presented here, again without undue experimentation, to replace the alpha silyl groups with alpha olefins, and such methods and preparations are considered within the scope of the present invention. In such embodiments, the aromatic silylated products of the present invention, whether isolated or generated in situ, are further reacted under conditions sufficient (including the presence of a suitable transition metal catalyst) to convert the silylated product to aromatic alpha-olefin products.

The following listing of embodiments is intended to complement, rather than displace or supersede, the previous descriptions.

Embodiment 1

A chemical system for silylating an organic substrate comprising an aromatic moiety, said system comprising a mixture of (a) at least one organosilane and (b) at least one strong base, said system preferably being substantially free of transition-metal compounds.

Embodiment 2

The system of Embodiment 1, wherein the transition-metal compound is present at less than 10 ppm, relative to the weight of the total system.

Embodiment 3

The chemical system of Embodiment 1 or 2, further comprising an optionally substituted tetraalkylethylenediamine (e.g., tetramethylethylenediamine), an optionally substituted 1,7-phenanthroline derivative, an optionally substituted 1,10-phenanthroline derivative, an optionally substituted 2,2'-bipyridine derivatives, or an optionally substituted 4-dimethylaminopyridine derivative.

Embodiment 4

The system of any one of Embodiments 1 to 3, that is substantially free of water, oxygen, or both water and oxygen.

Embodiment 5

The system of any one of Embodiments 1 to 4, wherein at least one organosilane comprises an organosilane of Formula (I) or Formula (II):

$$(R)_{4-m}Si(H)_m \quad (I)$$

$$R-[-SiH(R)-O-]_nR \quad (II)$$

where: m is 1, 2, or 3; n is 10 to 100; and each R is independently optionally substituted $C_{1-12}$ alkyl or heteroalkyl, optionally substituted $C_{5-20}$ aryl or heteroaryl, optionally substituted $C_{6-30}$ alkaryl or heteroalkaryl, optionally substituted $C_{6-30}$ aralkyl or heteroaralkyl, optionally substituted —O—$C_{1-12}$ alkyl or heteroalkyl, optionally substituted —O—$C_{5-20}$ aryl or heteroaryl, optionally substituted —O—$C_{6-30}$ alkaryl or heteroalkaryl, or optionally substituted —O—$C_{6-30}$ aralkyl or heteroaralkyl, and, if substituted, the substituents may be phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents may optionally provide a tether to an insoluble or sparingly soluble support media comprising alumina, silica, or carbon.

Embodiment 6

The system of Embodiment 5, wherein the organosilane is $(R)_3SiH$, where R is $C_{1-6}$ alkyl.

Embodiment 7

The system of any one of Embodiments 1 to 6, wherein the at least one strong base comprises an alkali or alkaline earth metal hydride or alkoxide.

Embodiment 8

The system of any one of Embodiments 1 to 7, wherein the at least one strong base comprises an alkali or alkaline earth metal hydride.

Embodiment 9

The system of Embodiment 8, wherein the at least one strong base comprises calcium hydride or potassium hydride.

Embodiment 10

The system of any one of Embodiments 1 to 7, wherein the at least one strong base comprises an alkali or alkaline earth metal alkoxide.

Embodiment 11

The system of Embodiment 10, wherein the at least one alkoxide comprises a $C_{1-12}$ linear or branched alkyl moiety or a $C_{5-10}$ aromatic or heteroaromatic moiety.

Embodiment 12

The system of Embodiment 11, wherein the at least one alkoxide comprises methoxide, ethoxide, propoxide, butoxide, or 2-ethyl-hexyl alkoxide.

Embodiment 13

The system of any one of Embodiments 7 to 12, wherein the alkali or alkaline earth metal hydride or alkoxide base is a potassium or cesium alkoxide.

Embodiment 14

The system of any one of Embodiments 1 to 13, where the organosilane is triethylsilane and the strong base is potassium tert-butoxide.

Embodiment 15

The system of any one of Embodiments 1 to 14, wherein the organosilane and the at least one strong base are present together at a molar ratio, with respect to one another, in a range of from about 20:1 to about 1:1.

Embodiment 16

The system of any one of Embodiments 1 to 15, further comprising an organic aromatic compound, said compound being a solvent, a substrate, or both a solvent and a substrate.

Embodiment 17

The system of Embodiment 16, wherein the organic compound comprises an optionally substituted benzene, biphenyl, naphthalene, or anthracene ring structure.

Embodiment 18

The system of Embodiment 16 or 17, wherein the organic aromatic compound comprises a heteroaryl moiety.

Embodiment 19

The system of Embodiment 18, wherein the organic aromatic compound comprises an optionally substituted furan, pyrrole, thiophene, pyrazole, imidazole, triazole, isoxazole, oxazole, thiazole, isothiazole, oxadiazole, pyridine, pyridazine, pyrimidine, pyrazine, triazone, benzofuran, benzopyrrole, benzothiophene, isobenzofuran, isobenzopyrrole, isobenzothiophene, indole, isoindole, indolizine, indazole, azaindole, benzisoxazole, benzoxazole, quinoline, isoquinoline, cinnoline, quinazoline, naphthyridine, 2,3-dihydrobenzofuran, 2,3-dihydrobenzopyrrole, 2,3-dihydrobenzothiophene, dibenzofuran, xanthene, dibenzopyrol, or dibenzothiophene moiety.

Embodiment 20

The system of Embodiment 18 or 19, wherein the organic aromatic compound comprises an optionally substituted furan, pyrrole, thiophene, pyrazole, imidazole, benzofuran, benzopyrrole, benzothiophene, indole, azaindole, dibenzofuran, xanthene, dibenzopyrrole, dibenzothiophene, or a hindered dibenzofuran, dibenzopyrrole, or dibenzothiophene moiety.

Embodiment 21

The system of any one of Embodiments 16 to 20, wherein the organic aromatic compound comprises at least one of the following moieties:

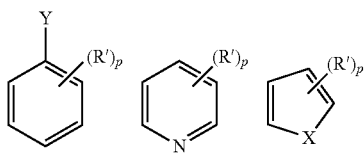

where
X is N—R", O, or S;
Y is H, N(R")$_2$, O—R", or S—R"
p is 0 to 4, 0 to 3, 0 to 2, or 0 to 1;
R' is a functional group "Fn," as described above, or (R')$_p$ is an optionally substituted fused alicyclic, heteroalicyclic, aryl or heteroaryl moiety; and
R" is an amine protecting group or an optionally substituted alkyl, aryl, heteroaryl, alkaryl or alk-heteroaryl, preferably optionally substituted $C_1$-$C_6$ alkyl, phenyl, tolyl, benzyl, or phenethyl.

Embodiment 22

The system of any one of Embodiments 16 to 21, wherein the substrate comprises at least one of the following moieties:

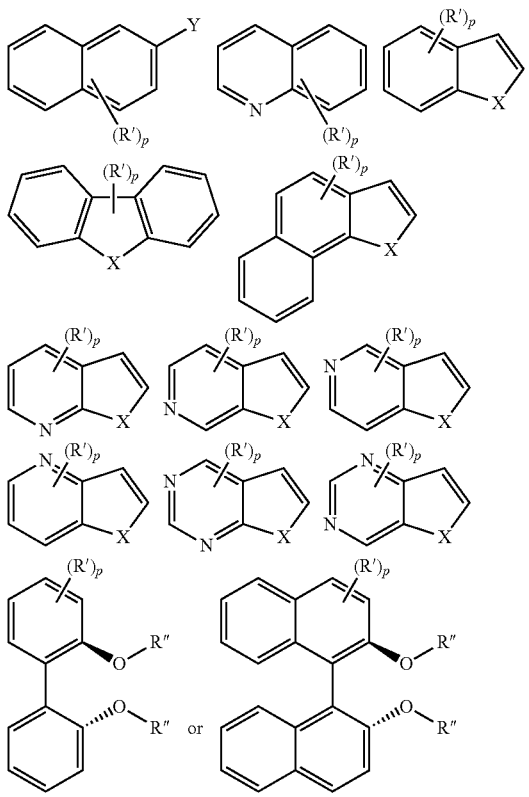

where X, Y, R', R" and p are as defined above. Note that the designation

in each case, is intended to allow for substitution on either aromatic ring.

Embodiment 23

The system of method of any one of Embodiments 16 to 21, wherein the aromatic organic compound comprises at least one alpha-methyl or methylene C—H bond, said method resulting in the formation of an alpha silane.

Embodiment 24

A method of silylating a substrate comprising an aromatic moiety, said method comprising contacting a quantity of the organic substrate with a system of any one of Embodiments 1 to 23.

Embodiment 25

A method comprising contacting an organic substrate comprising an aromatic moiety with a mixture of (a) at least one organosilane and (b) at least one strong base, under conditions sufficient to silylate the substrate; wherein said mixture and substrate are preferably substantially free of transition-metal compounds.

Embodiment 26

The method of Embodiment 25, wherein the transition-metal compound is present at less than 10 ppm, relative to the weight of the total system.

Embodiment 27

The method of Embodiments 25 or 26, wherein the mixture further comprises an optionally substituted tetraalkylethylenediamine (e.g., tetramethylethylenediamine), an optionally substituted 1,7-phenanthroline derivative, an optionally substituted 1,10-phenanthroline derivative, an optionally substituted 2,2'-bipyridine derivatives, or an optionally substituted 4-dimethylaminopyridine derivative.

Embodiment 28

The method of any one of Embodiments 25 to 27, that is substantially free of water, oxygen, or both water and oxygen.

Embodiment 29

The method of any one of Embodiments 25 to 28, wherein at least one organosilane comprises an organosilane of Formula (I) or Formula (II):

$$(R)_{4-m}Si(H)_m \quad (I)$$

$$R\text{—}[\text{—}SiH(R)\text{—}O\text{—}]_n R \quad (II)$$

where
m is 1, 2, or 3 (preferably 1);
n is 10 to 100; and
and each R is independently optionally substituted $C_{1-12}$ alkyl or heteroalkyl, optionally substituted $C_{5-20}$ aryl or heteroaryl, optionally substituted $C_{6-30}$ alkaryl or heteroalkaryl, optionally substituted $C_{6-30}$ aralkyl or heteroaralkyl, optionally substituted —O—$C_{1-12}$ alkyl or heteroalkyl, optionally substituted —O—$C_{5-20}$ aryl or heteroaryl, optionally substituted —O—$C_{6-30}$ alkaryl or heteroalkaryl, or optionally substituted —O—$C_{6-30}$ aralkyl or heteroaralkyl, and, if substituted, the substituents may be phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents may optionally provide a tether to an insoluble or sparingly soluble support media comprising alumina, silica, or carbon.

Embodiment 30

The method of any one of Embodiments 25 to 29, wherein the organosilane is $(R)_3SiH$, where R is independently $C_{1-6}$ alkyl.

Embodiment 31

The method of any one of embodiments 25 to 30, wherein the at least one strong base comprises an alkali or alkaline earth metal hydride or alkoxide.

Embodiment 32

The method of any one of Embodiments 25 to 31, wherein the at least one strong base comprises an alkali or alkaline earth metal hydride.

Embodiment 33

The method of Embodiment 32, wherein the at least one strong base comprises calcium hydride or potassium hydride.

Embodiment 34

The method of any one of Embodiments 25 to 33, wherein the at least one strong base comprises an alkali or alkaline earth metal alkoxide.

Embodiment 35

The method of Embodiment 34, wherein the at least one alkoxide comprises a $C_{1-12}$ linear or branched alkyl moiety or a $C_{5-10}$ aryl or heteroaryl moiety.

Embodiment 36

The method of Embodiment 35, wherein the at least one alkoxide comprises methoxide, ethoxide, propoxide, butoxide, or 2-ethyl-hexyl alkoxide.

Embodiment 37

The method of any one of Embodiments 31 to 36, wherein the alkali or alkaline earth metal hydride or alkoxide is a potassium or cesium alkoxide.

Embodiment 38

The method of any one of Embodiments 25 to 37, where the organosilane is triethylsilane and the strong base is potassium tert-butoxide.

Embodiment 39

The method of any one of Embodiments 25 to 28, wherein the organosilane and the at least one strong base are present together at a molar ratio, with respect to one another, in a range of from about 20:1 to about 1:1.

Embodiment 40

The method of any one of Embodiments 25 to 39, wherein the at least one strong base and substrate are present together at a molar ratio, with respect to one another, in a range of from about 0.01:1 to about 5:1, preferably in a range of from about 0.01:1 to about 0.9:1.

Embodiment 41

The method of any one of Embodiments 25 to 40, wherein the organic substrate comprises an optionally substituted benzene, biphenyl, naphthalene, or anthracene ring structure.

Embodiment 42

The method of any one of Embodiments 25 to 41, wherein the organic substrate comprises an exocyclic aromatic C—X bond, where X is N, O, or S.

Embodiment 43

The method of any one of Embodiments 25 to 42, wherein the organic substrate comprises an exocyclic aromatic C—X bond and the silylation occurs ortho to the exocyclic C—X bond, where X is N, O, or S.

Embodiment 44

The method of any one of Embodiments 25 to 43, wherein the organic substrate comprises a heteroaryl moiety.

Embodiment 45

The method of any one of Embodiments 25 to 44, wherein the substrate comprises an optionally substituted furan, pyrrole, thiophene, pyrazole, imidazole, triazole, isoxazole, oxazole, thiazole, isothiazole, oxadiazole, pyridine, pyridazine, pyrimidine, pyrazine, triazone, benzofuran, benzopyrrole, benzothiophene, isobenzofuran, isobenzopyrrole, isobenzothiophene, indole, isoindole, indolizine, indazole, azaindole, benzisoxazole, benzoxazole, quinoline, isoquinoline, cinnoline, quinazoline, naphthyridine, 2,3-dihydrobenzofuran, 2,3-dihydrobenzopyrrole, 2,3-dihydrobenzothiophene, dibenzofuran, xanthene, dibenzopyrol, or dibenzothiophene moiety.

Embodiment 46

The method of any one of Embodiments 25 to 45, wherein the substrate comprises an optionally substituted furan, pyrrole, thiophene, pyrazole, imidazole, benzofuran, benzopyrrole, benzothiophene, indole, azaindole, dibenzofuran, xanthene, dibenzopyrrole, or a dibenzothiophene.

Embodiment 47

The method of any one of Embodiments 25 to 46, wherein the organic aromatic substrate comprises at least one of the following moieties:

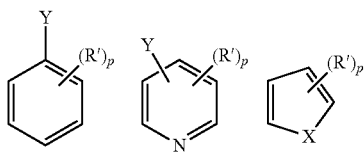

where
X is N—R", O, or S;
Y is H, N(R")$_2$, O—R", or S—R"
p is 0 to 4, 0 to 3, 0 to 2, or 0 to 1;
R' is a functional group "Fn," as described above, or (R')$_p$ is an optionally substituted fused alicyclic, heteroalicyclic, aryl or heteroaryl moiety; and
R" is an amine protecting group or an optionally substituted alkyl, aryl, heteroaryl, alkaryl or alk-heteroaryl, preferably optionally substituted C$_1$-C$_6$ alkyl, phenyl, tolyl, benzyl, or phenethyl.

Embodiment 48

The method of any one of Embodiments 25 to 47, wherein the substrate comprises at least one of the following moieties:

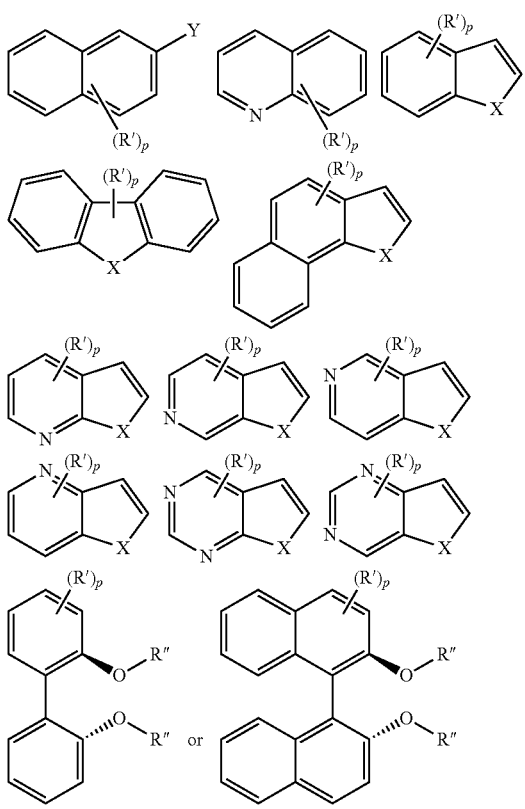

where X, Y, R', R" and p are as defined above. Note that the designation

in each case, is intended to allow for substitution on either aromatic ring.

Embodiment 49

The method of any one of Embodiments 25 to 48, wherein the organic substrate comprises a heteroaryl moiety of structure:

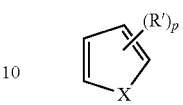

and the silylation occurs at the C-2 position of the heteroaryl ring.

Embodiment 50

The method of any one of Embodiments 25 to 49, wherein the organic substrate comprises a heteroaryl moiety of structure:

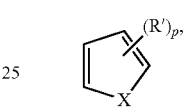

and the silylation occurs at the C-3 position of the heteroaryl ring.

Embodiment 51

The method of any one of Embodiments 25 to 50, wherein the aromatic substrate comprises at least one alpha-methyl or methylene C—H bond, said method resulting in the formation of a alpha silane.

Embodiment 52

The method of any one of Embodiments 25 to 51, wherein the aromatic substrate is polymeric.

Embodiment 53

The method of any one of Embodiments 25 to 52, wherein the aromatic silylated product is further reacted under conditions sufficient to couple the silylated product with a second aromatic compound to prepare a biaryl product.

Embodiment 54

The method of any one of Embodiments 25 to 52, wherein the aromatic silylated product is further reacted under conditions sufficient to convert the silylated product to an aromatic hydroxylated product.

Embodiment 55

The method of any one of Embodiments 25 to 52, wherein the aromatic silylated product is further reacted under conditions sufficient to convert the silylated product to an aromatic alpha-olefin product.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

Example 1

General Information

All reactions were carried out in dry glassware under an argon atmosphere using standard Schlenk line techniques or in a Vacuum Atmospheres Glovebox under a nitrogen atmosphere unless specified otherwise. Mesitylene (puriss., ≥99.0% (GC)) was refluxed over sodium/benzophenone, then distilled. Tetrahydrofuran was purified by passage through a solvent purification column then further distilled over sodium-potassium alloy and degassed with argon. All other solvents were purified by passage through solvent purification columns and further degassed with argon. NMR solvents for air-sensitive experiments were dried over $CaH_2$ and vacuum transferred or distilled into a dry Schlenk flask and subsequently degassed with argon. Triethylsilane (99%) was purchased from Sigma-Aldrich, refluxed over molecular sieves, and then distilled. It was then degassed by three freeze-pump-thaw cycles prior to use and subsequently passed through neutral alumina. Deuterotriethylsilane (97 atom % D) was purchased from Sigma-Aldrich and degassed by three freeze-pump-thaw cycles prior to use and other commercially available liquid reagents were treated analogously. Phenyldimethylsilane (≥98%), ethyldimethylsilane (98%) and diethylsilane (99%) were purchased from Sigma-Aldrich and distilled over $CaH_2$ and degassed by three freeze-pump-thaw cycles prior to use. Other commercially available liquid reagents were treated analogously. 1-methylindole (≥97%), benzofuran (99%), thianaphthene (98%), 1-methoxynaphthalene (≥98%), anisole (99%) and thioanisole (99%) were purchased from Sigma-Aldrich and were distilled prior to use. 2-methoxynaphthalene was recrystallized twice from boiling $Et_2O$. 1-phenylpyrrole (99%) was dissolved in $Et_2O$ and passed through activated alumina. The ether was removed in vacuo and the solid residue was recrystallized twice from a 3:1 mixture of absolute EtOH/water. 1-phenyl pyrrole (99%), diphenyl ether (≥99%), dibenzothiophene (≥99%) were purchased from Sigma-Aldrich and used as received. 4-methoxypyridine (97%) and 2,6-dimethoxypyridine (98%) were purchased from Sigma-Aldrich, passed several times through neutral, activated alumina and subjected to 3 freeze-pump-thaw cycles prior to use. 1-methyl-7-azaindole was prepared following the procedure of Cheve, G. et al., *Med chem comm* 2012, 3, 788. Sublimed grade KOt-Bu (99.99%) was purchased from Sigma-Aldrich and subjected to vacuum sublimation (30 mTorr, 160° C.) prior to use. Di-4-(methyl)phenyl ether, 1-naphthol, 2-naphthol, 4-tert-butylanisole, 4-methylanisole, 1,3-diphenoxybenzene, 2-methoxynaphthalene, and 1.0M tetrabutylammonium fluoride THF solution were purchased from Sigma-Aldrich and used as received. 4-(Methoxy)dibenzofuran, di-4-(tert-butyl)phenyl ether, naphthyl ethers, 4-(phenyl)phenyl phenyl ether, 2-ethoxynaphthalene, 2-Neopentyloxynaphthalene, 2-tert-butyloxynaphthalene were synthesized according to the literature procedures. Standard NMR spectroscopy experiments were conducted on a Varian Mercury ($^1$H, 300 MHz) spectrometer, a Varian Inova 400 MHz spectrometer, a Varian 500 MHz spectrometer equipped with an AutoX probe, or a Varian 600 MHz spectrometer equipped with a Triax Probe. Chemical shifts are reported in ppm downfield from $Me_4Si$ by using the residual solvent peak as an internal standard. Spectra were analyzed and processed using MestReNova Ver. 7. GC-FID analyses were obtained on an Agilent 6890N gas chromatograph equipped with a HP-5 (5%-phenyl)-methylpolysiloxane capillary column (Agilent). GC-MS analyses were obtained on an Agilent 6850 gas chromatograph equipped with a HP-5 (5%-phenyl)-methylpolysiloxane capillary column (Agilent). High-resolution mass spectra (EI and FAB) were acquired by the California Institute of Technology Mass Spectrometry Facility. EPR spectra were recorded on a Bruker EMS spectrometer.

Example 2

ICP-MS Analysis

ICP-MS analysis was conducted using the California Institute of Technology MS facility with 100 mg samples of dibenzofuran, triethylsilane, mesitylene and potassium tert-butoxide, which were added to 50 mL DigiTUBE digestion tubes (SCP Science) followed by addition of 3.0 mL of Plasma Pure nitric acid (SCP Science) to each digestion tube and heating to 75° C. for 36 hours. After digestion, each sample was diluted using Nanopure/Milli Q water to 50 mL and sample analysis performed on an HP 4500 ICPMS spectrometer. Semiquantitative analysis was performed using a 10 ppm solution of lithium, yttrium, cerium and thallium for calibration. Each sample was analyzed twice and the average measurements are given. (Table 1).

TABLE 1

ICP-MS Analysis of Various Metals in Reagents and Reaction Mixture

| Element | Reagent (unit: ppm) | | | | Reaction Mixture |
|---|---|---|---|---|---|
| | Dibenzofuran | KOt-Bu | $Et_3SiH$ | Mesitylene | |
| Fe | 0.15 | 4.92 | 0.67 | 0.11 | 5.80 |
| Ru | 0.00 | 0.07 | 0.00 | 0.01 | 3.13 |
| Os | 0.01 | 0.01 | 0.01 | 0.00 | 0.20 |
| Co | 0.00 | 0.01 | 0.00 | 0.00 | 0.26 |
| Rh | 0.00 | 0.00 | 0.00 | 0.00 | 1.07 |
| Ir | 0.00 | 0.01 | 0.00 | 0.09 | 0.40 |
| Ni | 0.12 | 0.06 | 0.06 | 0.38 | 0.79 |
| Pd | 0.00 | 0.04 | 0.00 | 0.01 | 0.88 |
| Pt | 0.00 | 0.07 | 0.00 | 0.01 | 1.74 |
| Cu | 0.03 | 10.42 | 0.04 | 0.09 | 7.59 |

Example 3

General Procedure

In a glovebox, a 4 mL screw cap vial was loaded with the corresponding substrate (0.1-0.5 mmol, 1 equiv.), base (0.1-5 equiv.) and a magnetic stirring bar, followed by syringe addition of the solvent (1 mL) and triethylsilane (1-5 equiv.). The reaction vial was sealed with a Teflon-lined screw cap and heated at a given temperature and time inside the glovebox. After cooling to room temperature, dark red to black reaction mixture was diluted with diethyl ether (3 mL) and carefully quenched with 1 ml of 1 N aqueous HCl. Tridecane (internal standard for GC) was added, the organic layer was separated and the aqueous layer was extracted with ether (3 mL) until TLC controls show no UV-active compounds present in the extracts. The combined organic layers were passed through a short pad of Celite and subjected to GC/FID, GC/MS and $^1$H-NMR analyses. Unless stated otherwise, in preparative experiments only products with the overall yield exceeding 2% were isolated and characterized. In the case of naphthyl alkyl ethers, a different workup procedure was used. After cooling, the reaction was diluted with dichloromethane (5 mL) and carefully quenched with 2 mL of 1 N aqueous HCl. Tridecane was added, and the mixture was transferred to a separatory funnel. The organic phase was separated, and the aqueous layer was extracted with dichloromethane (3 mL). The combined organic layers were dried over anhydrous $MgSO_4$ and filtered. For all reactions, the products were identified using GC/MS and GC/FID and NMR by comparison with the authentic samples. Trace soluble side products observed in naphthyl alkyl ether reductions included naphthalene, 1,2,3,4-tetrahydronaphthalene, and 5,6,7,8-tetrahydro-2-naphthol.

In most cases, the products were isolated and purified before characterization by NMR and/or GC-MS, either by independent spectral analysis or comparison with authentic samples, or both. In those cases where the product was not isolated and purified, characterization was made on the basis of GC-MS and/or GC-FID analyses.

Example 4

Synthesis and Characterization of Selected Compounds

Example 4.1

4-(Triethylsilyl)dibenzofuran (3)

The title compound was prepared by analogy to the protocol for the synthesis of 4-(trimethylsilyl)dibenzofuran by Kelly and co-workers; Bekele, H., et al., *J. Org. Chem.*, 1997, 62, 2259. Data for (3): Colorless oil. $^1$H-NMR (500 MHz, $CDCl_3$): δ 7.99-7.96 (m, 2H$_{ar}$), 7.59 (d-like, J=10 Hz, 1H$_{ar}$), 7.54 (dd, J=2, 5 Hz, 1H$_{ar}$), 7.48-7.44 (m, 1H$_{ar}$), 7.37-7.33 (m, 2H$_{ar}$), 1.03 (m, 15H, 3$CH_2CH_3$). $^{13}$C-NMR (126 MHz, $CDCl_3$) δ 161.30, 156.05, 133.57, 126.92, 122.52, 122.48, 121.58, 120.68, 111.75, 7.63, 3.59. HRMS: [$C_{18}H_{22}OSi$] calculated 282.1440; measured 282.1444.

Example 4.2

4,6-Bis(triethylsilyl)dibenzofuran (4)

To a solution of dibenzofuran (2.00 g, 11.9 mmol, 1 equiv.) and tetramethylethylenediamine (11.1 mL, 29.7 mmol, 2.5 equiv.) in tetrahydrofuran (50 ml) tert-butyllithium (17.5 mL of 1.7 M solution in pentane, 29.8 mmol, 2.5 equiv.) was slowly added at −78° C. under argon. The mixture was allowed to reach ambient temperature and stirring was continued for 4 h prior to addition of chlorotriethylsilane (10.1 mL, 60 mmol, 5 equiv.). The resulting mixture was stirred at ambient temperature for another 16 h. After quenching the reaction with the saturated ammonium chloride solution (40 mL) and extraction with diethyl ether (3×30 mL), the combined organic layers were dried over anhydrous sodium sulfate, filtered and the filtrate concentrated in vacuo. Crude reaction mixture was purified by chromatography on silica (hexanes) and product obtained was recrystallized from a mixture of methanol and isopropanol (1:1) to afford 4,6-bis(triethylsilyl)dibenzofuran (1.28 g, 2.45 mmol, 28%) as colorless needles. Data for (4): Colorless needles. M.p.=59-61° C. $^1$H-NMR (300 MHz, $CDCl_3$) δ 7.97 (dd, J=3, 9 Hz, 2H$_{ar}$), 7.54 (dd, J=3, 9 Hz, 2H$_{ar}$), 7.33 (t, J=9 Hz, 2H$_{ar}$), 1.07-0.95 (m, 30H, 6 $CH_2CH_3$). $^{13}$C-NMR (126 MHz, CDCl3) δ 160.90, 133.48, 122.87, 122.34, 121.57, 120.03, 7.66, 3.52. HRMS: [$C_{24}H_{36}OSi_2$] calculated 396.2305; measured 396.2321.

Example 4.3

3-(Triethylsilyl)biphenyl-2-ol (5)

The title compound was prepared via cleavage of 3 (vide infra). Data for (5): White solid. M.p.=44-46° C. $^1$H-NMR (300 MHz, $CDCl_3$) δ 7.52-7.40 (m, 5H$_{ar}$), 7.36 (dd, J=3, 9 Hz, 1H$_{ar}$), 7.23 (dd, J=3, 6 Hz, 1H$_{ar}$), 6.98 (t, J=9 Hz, 1H$_{ar}$), 5.41 (s, 1H, OH), 1.02-0.96 (m, 9H, $CH_3$), 0.91-0.83 (m, 6H, $CH_2$). $^{13}$C-NMR (75 MHz, $CDCl_3$) δ 157.25, 137.51, 135.97, 131.30, 129.58, 129.39, 128.01, 127.17, 123.04, 120.40, 7.79, 3.69. HRMS: [$C_{18}H_{24}OSi$] calculated 284.1596; measured 284.1583.

Example 4.4

(3'-Triethylsilyl)biphenyl-2-ol (6)

The title compound was prepared via cleavage of 3 (vide infra). Data for (6): Colorless oil. $^1$H-NMR (500 MHz, $CDCl_3$): δ 7.57-7.56 (m, 1H$_{ar}$), 7.54-7.52 (m, 1H$_{ar}$), 7.49-7.44 (m, 2H$_{ar}$), 7.28-7.24 (m, 2H$_{ar}$), 7.02-6.99 (m, 2H$_{ar}$), 5.24 (s, 1H, OH), 0.98 (t, J=10 Hz, 9H, $CH_3$), 0.82 (q, J=15 Hz, 6H, $CH_2$). $^{13}$C NMR (126 MHz, $CDCl_3$): δ 153.44, 139.07, 136.12, 134.71, 133.76, 130.23, 129.36, 129.08, 128.53, 128.44, 120.80, 115.72, 7.43, 3.31. HRMS: [$C_{18}H_{24}OSi$] calculated 284.1596; measured 284.1585.

Example 4.5

3,3'-Bis(triethylsilyl)biphenyl-2-ol (7)

The title compound was prepared according to General Procedure by heating dibenzofuran (1, 840 mg, 5.0 mmol, 1 equiv.) with KOt-Bu (1.12 g, 10 mmol, 2 equiv.) and Et$_3$SiH (4.0 ml, 25 mmol, 5 equiv.) in 20 ml of toluene for 20 hours at 100° C. After acidic aqueous work up, the crude reaction mixture was purified by chromatography on silica using hexanes and hexanes-ether (10:1) to give, among other isolated products, 20 mg (0.05 mmol, 1%) of 7. Data for (7): oily solid $^1$H-NMR (300 MHz, CDCl$_3$): δ 7.53-7.44 (m, 2H$_{ar}$), 7.46-7.44 (m, 2H$_{ar}$), 7.36 (dd, J=1.5, 7.5 Hz, 1H$_{ar}$), 7.23 (dd, J=1.5, 7.5 Hz, 1H$_{ar}$), 6.98 (t, J=7 Hz, 1H$_{ar}$), 5.42 (s, 1H, OH), 1.01-0.96 (m, 18H, 6CH$_3$) 0.91-0.77 (m, 15H, 6CH$_2$). $^{13}$C NMR (75 MHz, CDCl$_3$): δ 157.37, 139.45, 136.61, 135.87, 135.09, 133.86, 131.38, 129.57, 128.71, 127.55, 122.97, 120.36, 7.80, 7.57, 3.69, 3.46. HRMS: [C$_{24}$H$_{38}$OSi$_2$] calculated 398.2461; measured 396.2470.

Example 4.6 o-Triethylsilyldiphenyl ether o-Triethylsilyldiphenyl ether was prepared using the modified procedure by Fink on a 30 mmol scale based on diphenyl ether. After addition of Et$_3$SiCl, the reaction mixture was stirred at 40° C. for 4 hours followed by aqueous work up and vacuum distillation to obtain the title compound as colorless oil in 88% yield. $^1$H-NMR (500 MHz, CDCl$_3$: δ 7.47 (dd, J=7.0, 1.5 Hz, 1H$_{ar}$), 7.35-7.31 (m, 2H$_{ar}$), 7.30-7.25 (m, 1H$_{ar}$), 7.10-7.06 (m, 1H$_{ar}$), 7.02-6.97 (m, 2H$_{ar}$), 6.79 (d, J=8.0, 1H$_{ar}$), 0.95 (t-like, J=8.5 Hz, 9H), 0.83 (qlike, J=8.0 Hz, 6H). $^{13}$C-NMR (126 MHz, CDCl$_3$: δ 162.33, 157.39, 136.57, 130.58, 129.86, 129.82, 127.76, 123.34, 123.08, 122.86, 119.04, 117.22, 7.71, 3.55. HRMS: [C$_{18}$H$_{24}$SiO] calculated 284.1596, measured 284.1587.

Example 5

EPR Experiments

Figure 2B:
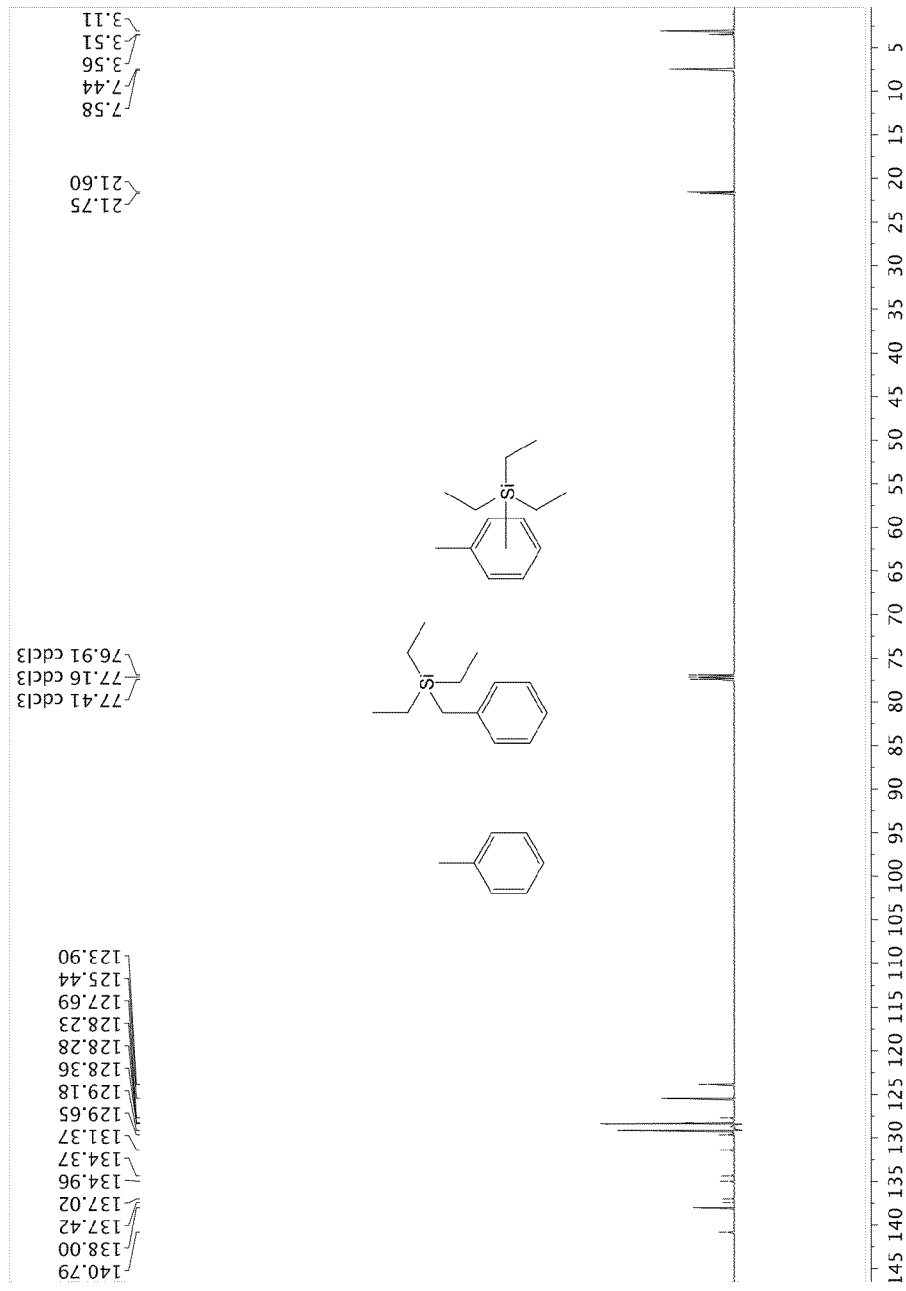
Figure 3A:
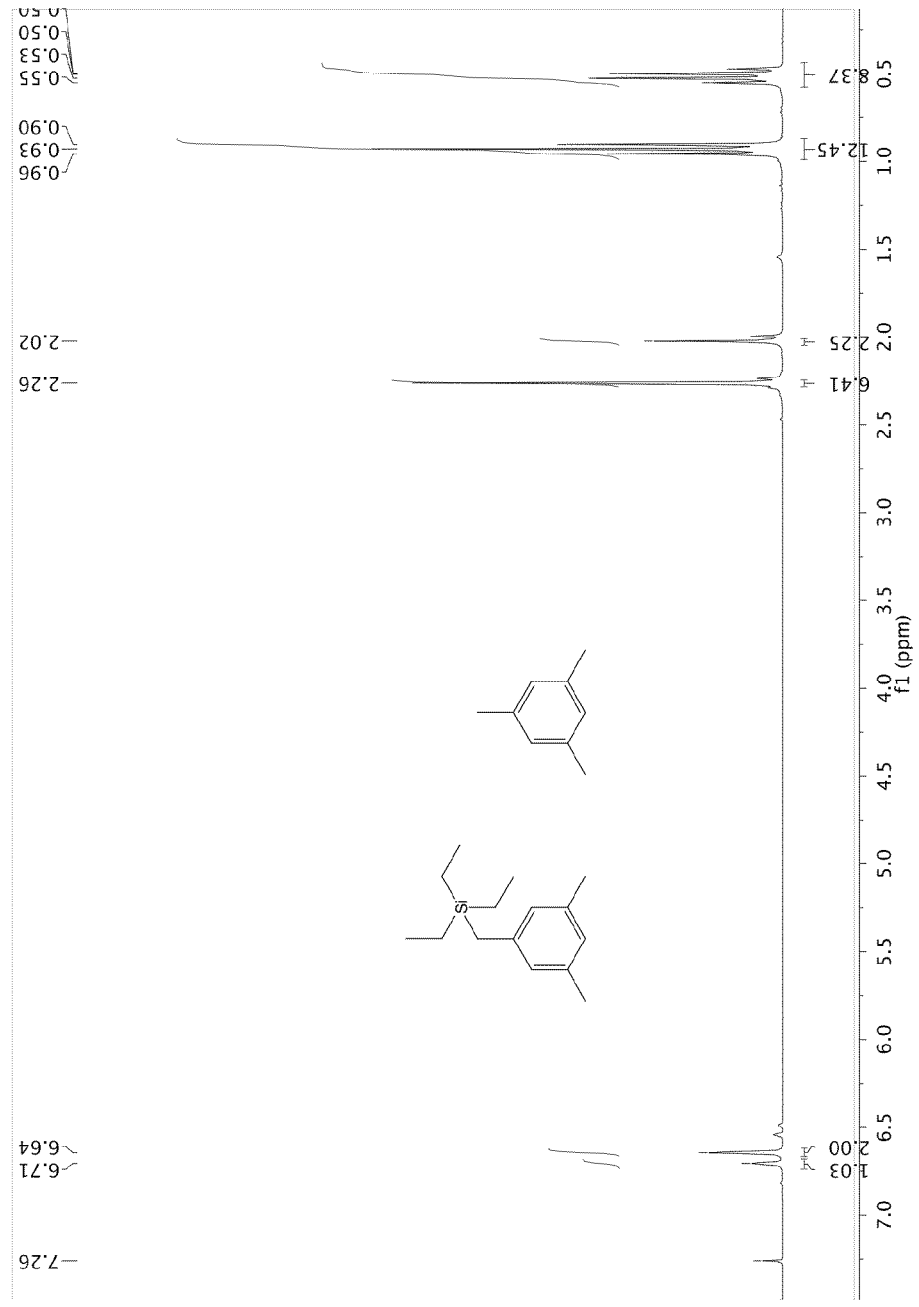
Figure 3B:
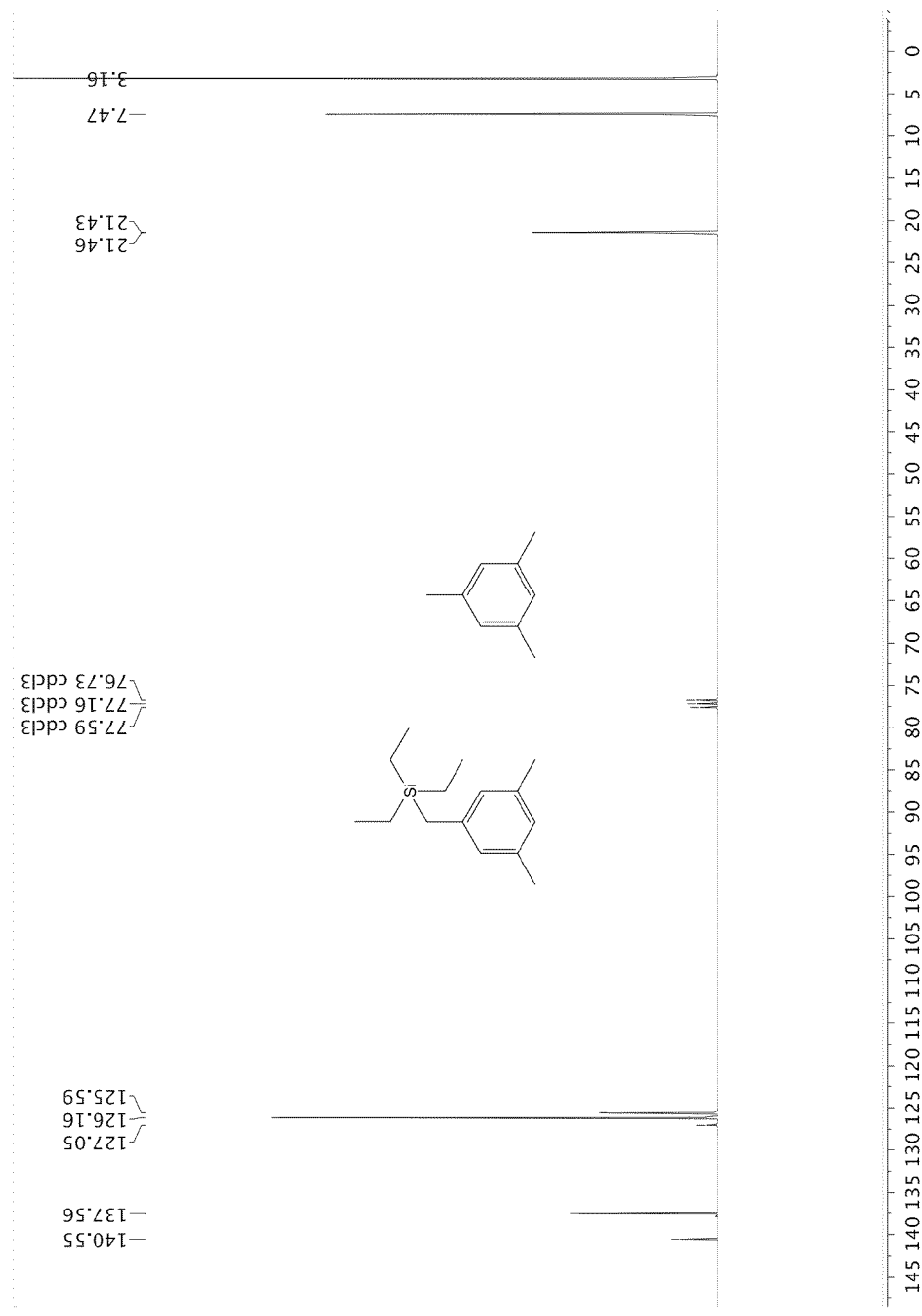
Figure 4A:
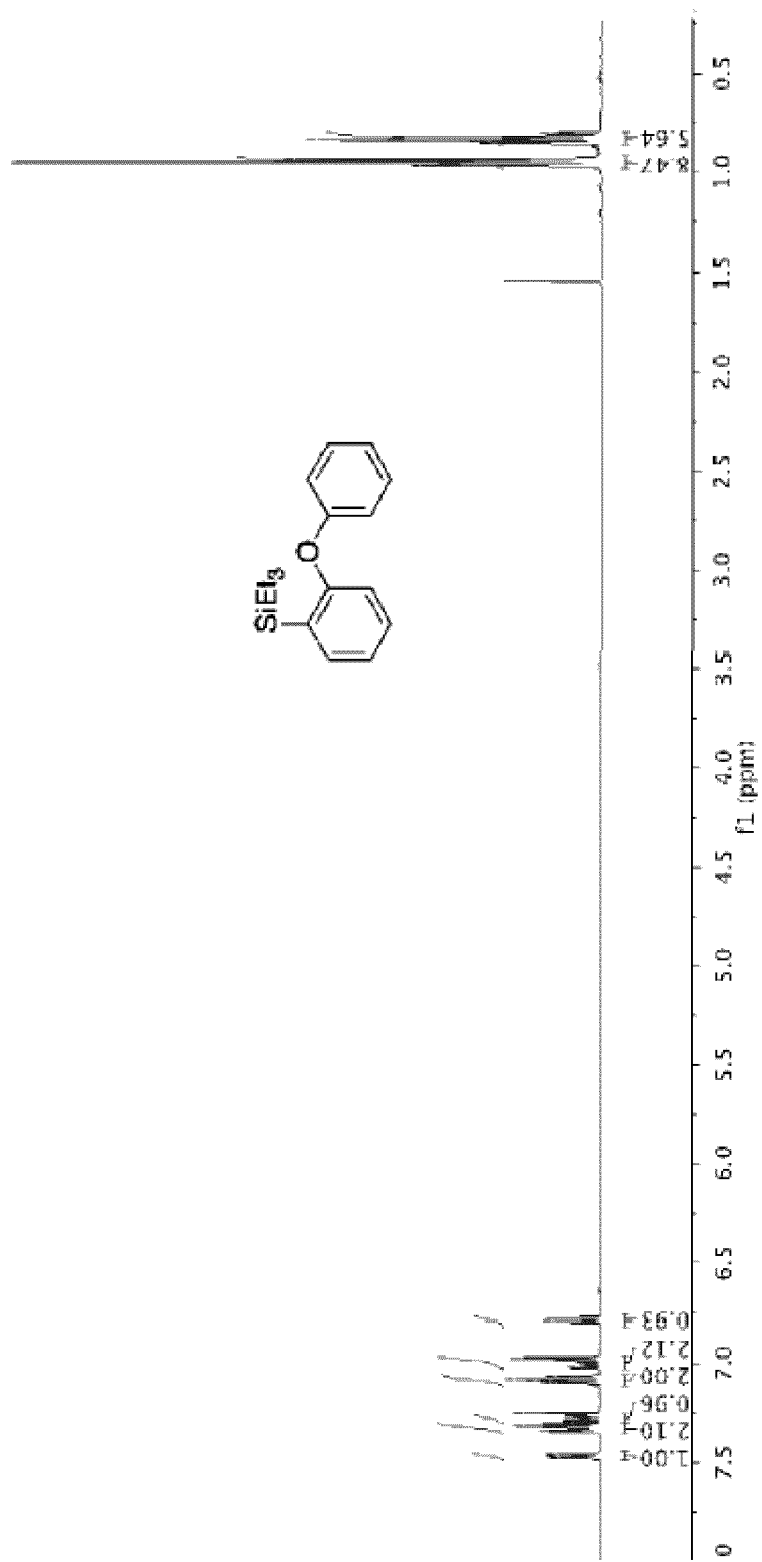
Figure 4B:
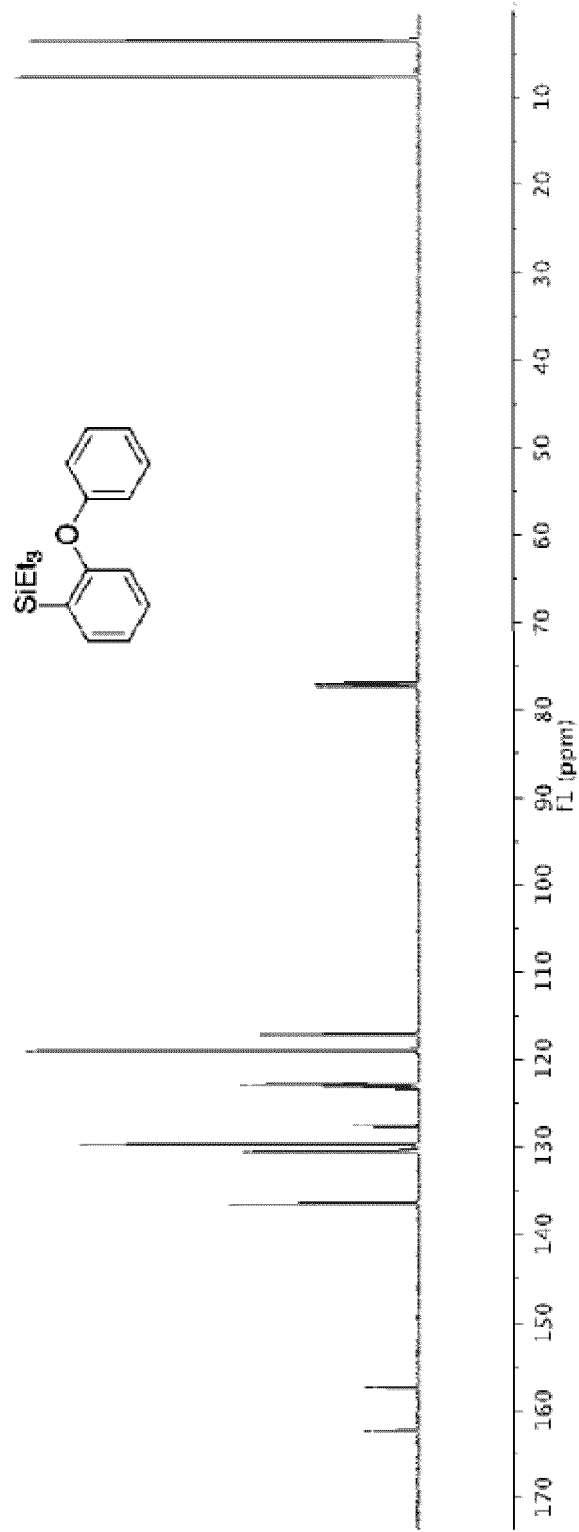

Dibenzofuran (1, 16.8 mg, 0.1 mmol, 1 equiv.), KOt-Bu (22.5 mg, 0.2 mmol, 2 equiv.) and Et$_3$SiH (80 microliters, 0.5 mmol, 5 equiv.) were heated in 0.4 ml of toluene for 1 hour at 100° C. inside the glovebox. After this time reaction mixture was diluted with 0.8 ml of toluene and filtered into an EPR tube. The reaction mixture was found to be EPR active and the spectrum was recorded within 20 min after filtration (FIG. 2). In a control experiment recorded without dibenzofuran, the same signal was observed albeit with lower intensity. These results are consistent with reactive radicals that have been documented for homolytic aromatic substitution reactions. The addition of 1,10-phenanthroline in conjunction with KOt-Bu was found to be detrimental since no conversion of 1 was observed.

Example 6

Selected Reactions

Example 6.1

Reactions of 4-(Triethylsilyl)dibenzofuran

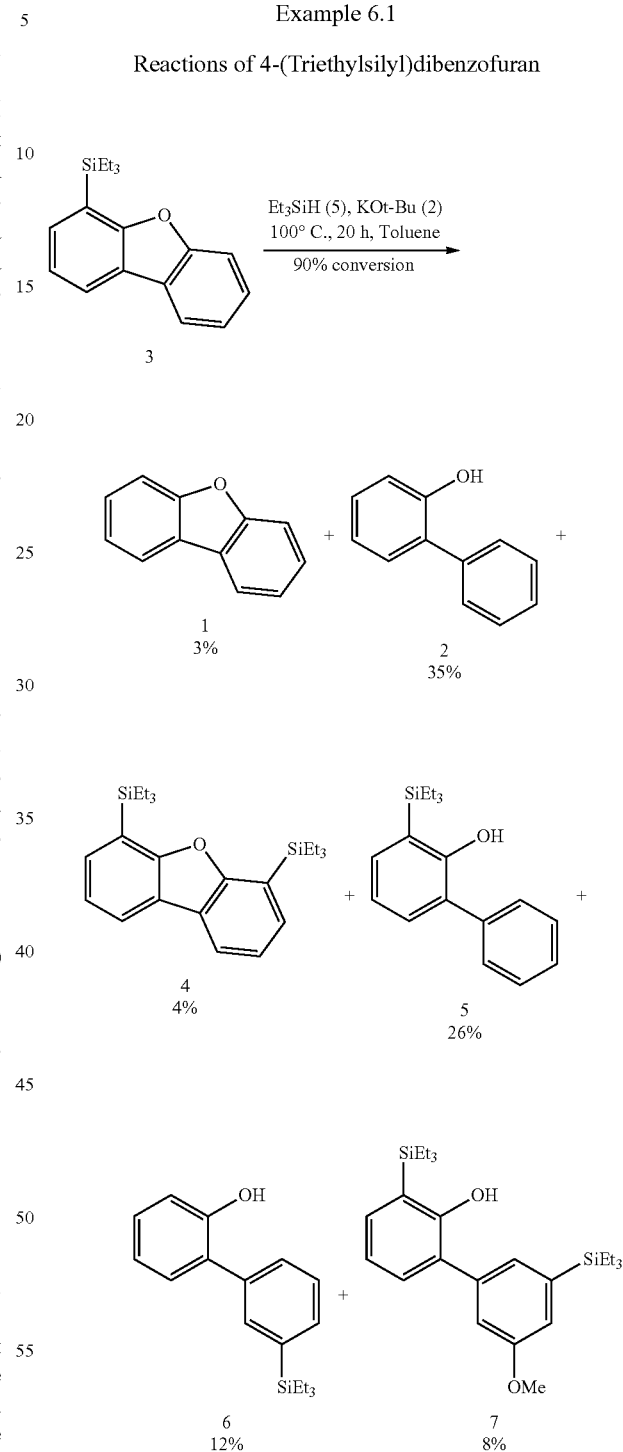

The reaction was conducted according to the General Procedure by heating 4-Et3Si-dibenzofuran (3, 141 mg, 0.5 mmol, 1 equiv.), KOt-Bu (112 mg, 1 mmol, 2 equiv.) and Et3SiH (401 microliters, 2.5 mmol, 5 equiv.) in 2 ml of toluene for 20 hours at 100° C. After acidic aqueous work up, the crude reaction mixture was purified by chromatography on silica using hexanes and hexanes-ether (10:1) to isolate 2-phenylphenol (2, 30 mg, 0.177 mmol, 35%), 2-triethylsilyl-6-phenylphenol (5, 37 mg, 0.134 mmol, 26%), 2-(3-triethyl-silylphenyl)phenol (6, 17 mg, 0.063 mmol, 12%). Quantities of unconsumed 3 as well as products 1, 4 and 7 were obtained using post-chromatography GC-FID analysis of the corresponding mixed fractions.

Example 6.2

Investigation of Silylated Dibenzofurans as Intermediates Towards C—O Bond Cleavage: Cleavage Attempts with KOt-Bu

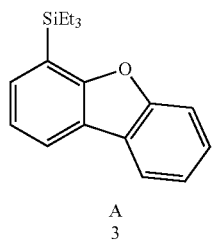

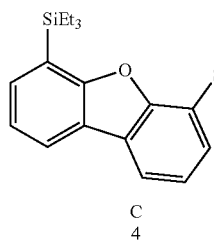

Starting material 3 (14.1 mg, 0.05 mmol, 1 equiv.) was heated with KOt-Bu (5.6 mg or 11.2 mg, 1 or 2 equiv., respectively) in 0.8 ml d-toluene at 100° C. for 20 hours in a J. Young tube under nitrogen. Monitoring the reaction progress by $^1$H NMR showed no conversion of 3 in both cases. Likewise, starting materials 3 (28.2 mg, 0.1 mmol, 1 equiv.) or 4 (39.6 mg 0.1 mmol, 1 equiv.) were heated with KOt-Bu (36.6 mg) in 0.3 mL of mesitylene at 160° C. for 20 hours. Subsequent analysis of the crude reaction mixtures by GC-FID or 1H NMR revealed 3% conversion to 1 in case of 3 and 5% conversion to 3 from 4.

Example 6.3

Reactions of 4-(Methoxy)dibenzofuran at Elevated Temperature

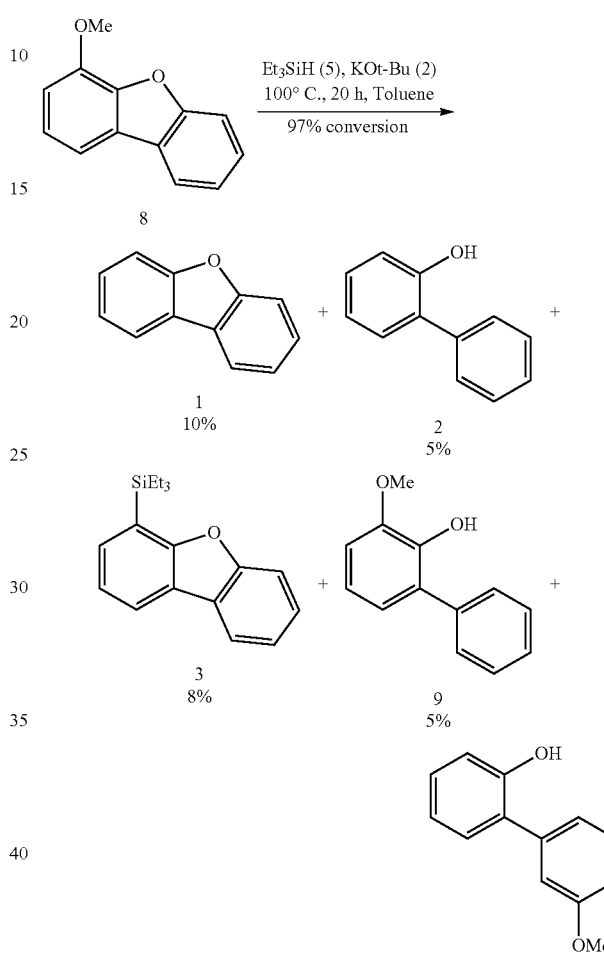

The reaction was conducted according to the General Procedure by heating 4-MeO-dibenzofuran (8, 89 mg, 0.5 mmol, 1 equiv.), KOt-Bu (112 mg, 1 mmol, 2 equiv.) and Et3SiH (401 microliters, 2.5 mmol, 5 equiv.) in 2 ml of toluene for 20 hours at 100° C. After aqueous work up, the crude reaction mixture was purified by chromatography on silica using hexanes and hexanes-ether to recover unconsumed starting material 8 (3 mg, 0.015 mmol, 3%) and isolate dibenzofuran (1, 8.4 mg, 0.05 mmol, 10%; since fractions of 1 contained small amounts of starting 8, quantification was done by $^1$H-NMR with $CH_2Br_2$ as an internal standard), 1,1'-biphenyl-2-ol (2, 4.3 mg, 0.025 mmol, 5%), 4-Et$_3$Si-dibenzofuran (3, 11 mg, 0.039 mmol, 8%), 2-methoxy-6-phenyl-phenol (9, mg, 0.025 mmol, 5%), 2-(3'-methoxyphenyl)phenol (10, 47 mg, 0.235 mmol, 47%). Note: only compounds with the yield exceeding 2% were characterized. $^1$H and $^{13}$C NMR spectral assignments of 9 and 10 were consistent with literature reports.

Example 6.4

Triethylsilylation of Arenes at Elevated Temperatures

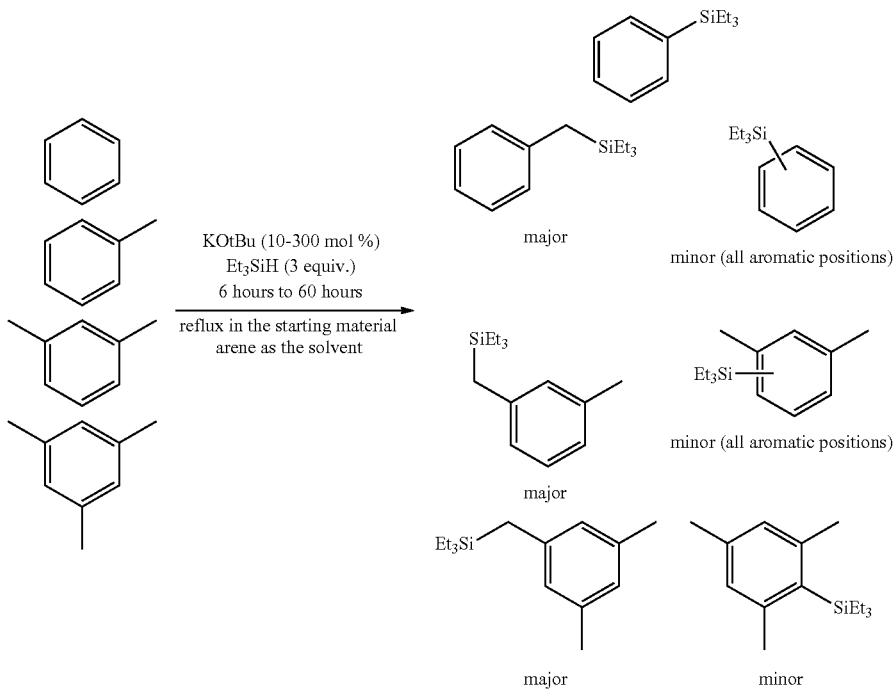

In many instances the formation of the solvent-derived silylated products was observed at elevated temperatures during experiments aimed at C—O, C—N, or C—S bond cleavage when using toluene or mesitylene as solvents at the elevated temperatures used in the reductive cleavage reactions. Since it was not possible to separate the resulting products from their respective parent solvents by column chromatography or distillation, at this point it was difficult to assess their yields, but they are tentatively estimated to be in 5-10% range based on Et$_3$SiH. In case of toluene, the identity of products was confirmed by comparison of the NMR spectra obtained with the literature data (Rychnovsky, et al. *J. Org. Chem.* 2003, 68, 10135.) Thus, it was concluded that the major product is benzyl triethylsilane (17), which is also consistent with the GC-MS analysis of fragmentation patterns of isomeric products. Likewise, it appeared that silylation of mesitylene proceeds predominantly into the benzylic (or alpha) position. HRMS [C$_{15}$H$_{26}$Si] calculated 234.1804, measured 234.1804).

Aromatic amines are also amenable to silylation. In the following case, GC-MS identified the following scheme was operable under the conditions provided:

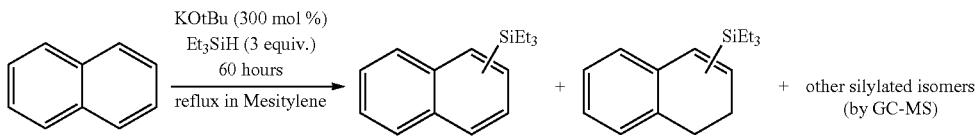

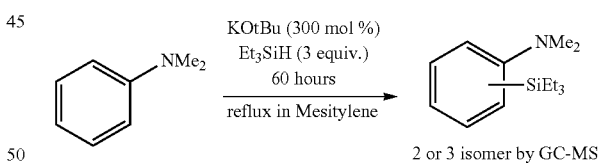

At lower temperatures, this reaction appeared to provide a mixture of product, with no single product identifiable. It is possible, though not confirmed, that the apparent normal proclivity to silylate ortho to the exocyclic amine was inhibited by the steric bulk associated with the two methyl groups.

Example 6.5

Silylation of Dibenzofuran at Elevated Temperatures

Experiments were conducted using the General Methods described in Examples 1 and 3, unless otherwise indicated. Yields were reproducible within ±2%. It is noteworthy here that low levels of base, especially substoichiometric amounts of base relative to the substrate, even at these elevated temperatures, resulted in the highest yields of silylated products, relative to cleavage products.

TABLE 2

Results of silylation of dibenzofuran at elevated temperatures

| Entry | Et₃SiH (equiv) | Base (equiv) | Solvent | T, °C. | Conv (%)$^a$ | 2 | 3 | 4 | 5 | 6 | 7 |
|---|---|---|---|---|---|---|---|---|---|---|---|
| 1 | 0 | KOt-Bu (2) | Toluene | 100 | 0 | — | — | — | — | — | — |
| 2 | 5 | None | Toluene | 100 | 0 | — | — | — | — | — | — |
| 3$^a$ | 5 | KOt-Bu (2) | Toluene | 100 | 70 | 34 | 28 | 4 | — | — | — |
| 4$^b$ | 5 | KOt-Bu (2) | Toluene | 100 | 98 | 38 | 16 | 10 | 21 | 2 | 7 |
| 5$^c$ | 5 | KOt-Bu (2) | Toluene | 100 | 98 | 5 | 28 | 46 | — | — | — |
| 6 | 4 | KOt-Bu (2) | Toluene | 100 | 100 | 41 | 17 | 15 | 12 | 1 | 9 |
| 7 | 3 | KOt-Bu (2) | Toluene | 100 | 96 | 42 | 20 | 9 | 13 | 1 | 4 |
| 8 | 2 | KOt-Bu (2) | Toluene | 100 | 87 | 34 | 30 | 10 | 6 | 1 | 3 |
| 9 | 1 | KOt-Bu (2) | Toluene | 100 | 56 | 19 | 29 | 1 | 2 | — | 1 |
| 10 | 5 | KOt-Bu (0.5) | Toluene | 100 | 89 | 12 | 48 | 20 | 9 | — | 1 |
| 11 | 2 | KOt-Bu (5) | Toluene | 100 | 66 | 9 | 43 | 8 | 2 | — | — |
| 12 | 3 | KOt-Bu (2) | Toluene | 100 | 97 | 63 | 10 | 1 | 22 | — | 2 |
| 13 | 5 | KH (1) | Dioxane | 100 | 49 | 1 | 43 | 5 | — | — | — |
| 14 | 5 | KOt-Bu (2) | Dioxane | 100 | 70 | 25 | 28 | 10 | 4 | 1 | 1 |
| 15$^d$ | — | KOt-Bu (2) | Et₃SiH | 100 | 99 | 26 | 13 | 25 | 11 | 1 | 21 |
| 16 | 5 | KOt-Bu (2) | Toluene | 80 | 98 | 29 | 18 | 26 | 9 | — | 7 |
| 17 | 3 | KOt-Bu (3) | Mesitylene | 165 | 100 | 85 | 3 | — | 5 | 2 | — |
| 18$^e$ | 3 | KOt-Bu (3) | Mesitylene | 165 | 100 | 95 | — | — | — | — | — |
| 19 | 2 | KOt-Bu (2) | Mesitylene | 165 | 100 | 62 | 8 | 1 | 12 | 1 | — |
| 20 | 3 | KOt-Bu (2) | Mesitylene | 165 | 97 | 52 | 17 | 5 | 16 | 1 | 2 |
| 21 | 1 | KOt-Bu (1) | Mesitylene | 165 | 57 | 30 | 21 | — | — | — | — |
| 22 | 3 | KOt-Bu (0.5) | Mesitylene | 165 | 85 | 29 | 35 | 15 | 4 | — | 2 |
| 23 | 5 | KOt-Bu (5) | Mesitylene | 165 | 100 | 77 | 3 | 0 | 3 | 8 | — |
| 24 | 3 | KH (3) | Mesitylene | 165 | 100 | 66 | 3 | 0 | 5 | 11 | — |
| 25 | 3 | KOEt (3) | Mesitylene | 165 | 100 | 85 | 4 | 0 | 1 | 8 | — |
| 26 | 3 | KOEt (3) | Mesitylene | 165 | 95 | 77 | 10 | 11 | — | — | — |
| 27 | 3 | KOEt (3) | Toluene | 100 | 40 | 19 | 19 | 2 | — | — | — |

TABLE 2-continued

Results of silylation of dibenzofuran at elevated temperatures

| Entry | Et₃SiH (equiv) | Base (equiv) | Solvent | T, °C. | Conv (%)$^a$ | 2 | 3 | 4 | 5 | 6 | 7 |
|---|---|---|---|---|---|---|---|---|---|---|---|
| 28 | 3 | KOMe (3) | Mesitylene | 165 | 64 | 31 | 27 | 2 | 3 | 1 | — |
| 29 | 3 | NaOt-Bu (3) | Mesitylene | 165 | 0 | — | — | — | — | — | — |
| 30 | 3 | LiOt-Bu (3) | Mesitylene | 165 | 0 | — | — | — | — | — | — |
| 31 | 3 | NaOEt (3) | Mesitylene | 165 | 0 | — | — | — | — | — | — |
| 32$^f$ | 3 | CsOR (2) | Toluene | 100 | 89 | 75 | 3 | 11 | — | — | — |
| 33 | 3 | KOt-Bu (3) | Benzene | 85 | 96 | 37 | 20 | 13 | 12 | — | 9 |
| 34 | 5 | KOt-Bu (2) | DMF | 100 | 0 | — | — | — | — | — | — |
| 35 | 5 | KOt-Bu (2) | DMA | 100 | 0 | — | — | — | — | — | — |
| 36 | 5 | KOt-Bu (2) | Diglyme | 100 | 0 | — | — | — | — | — | — |
| 37 | 5 | KOt-Bu (2) | t-BuOH | 100 | 0 | — | — | — | — | — | — |
| 38 | 5 | KOt-Bu (2) | Diisopropyl carbonol | 100 | 0 | — | — | — | — | — | — |
| 39 | 3 | KOt-Bu (3) | Methyl cyclohexane | 160 | 100 | 82 | — | — | — | 13 | — |
| 40$^g$ | PMHS (10) | KOt-Bu (3) | Methyl cyclohexane | 85 | 5-7 | — | — | — | — | — | — |

$^a$GC yields and conversions are reported using tridecane as the standard
$^b$the reaction was performed in 0.05M solution.
$^c$reaction conducted open to an Ar line
$^d$the reaction was performed in neat Et₃SiH.
$^e$with 1,4-cyclohexadiene (100 equivalent) co-solvent
$^f$R = 2-ethylhexyl.
$^g$using polymethylhydrosiloxane (PMHS) instead of Et₃SiH as organosilane

Example 6.6

Silylation of Aryl Alkyl Ethers at Elevated Temperatures

Silylations of aryl alkyl ethers at elevated temperatures were conducted under the conditions applied to diaryl ethers to probe the cleavage selectivity of sp$^2$ versus sp$^3$ C—O bond. At the elevated temperatures of these experiments, the reaction of 2-methoxynaphthalene gave 2-naphthol as the major product in moderate yield (Scheme 1). GC-MS analysis of the crude reaction mixture indicated the presence of trace amounts of naphthalene along with 2-methylnaphthalene and further reduced species, including products of partial aromatic reduction. Compounds presumably derived from 2-naphthol silylation were also detected. Likewise, cleavage of 2-ethoxynaphthalene under the same conditions gave 2-naphthol in slightly higher yield, but with the same or analogous side products. Sterically bulkier ethers were investigated to probe the versatility and possible mechanism of the C—O bond cleavage. Despite the large alkyl substituent adjacent to the ether oxygen, reaction of 2-neopentyloxynaphthalene provided 2-naphthol in approximately the same yield as with the less bulky substrates. Even 2-tert-butyloxynapthalene was cleaved to give the expected naphthol in 55% yield (Scheme 1). Control experiments performed at identical conditions but without triethylsilane provided 2-naphthol in cases of 2-ethoxy- and 2-tert-butyloxynapthalene albeit with substantially diminished yields. Since 2-methoxy- and 2-neopentyloxy-substrates remained intact in such silane-free cleavages, a b elimination mechanism is likely to be operative. When attempting to reduce 4-tert-butyl and 4-methyl anisoles under the standard conditions, the yields of the corresponding phenols were high, likely because of more challenging silylation of the substituted phenyl ring for the steric reasons (Scheme 2).

gomeric ether 14 that contains six $C_{ar}$—O bonds (Scheme 2, inset D). Remarkably, at 165° C. in mesitylene quantitative conversion of 14 was achieved and gave phenol, benzene, resorcinol and other unidentified products with merely 0.5 equivalent of silane per aryl oxygen bond.

In Scheme 2, compounds 1 to 7 refer to the corresponding compounds described in Example 5.9.

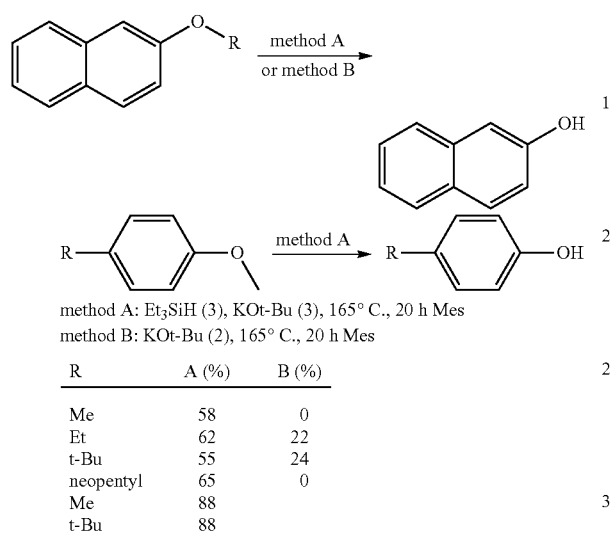

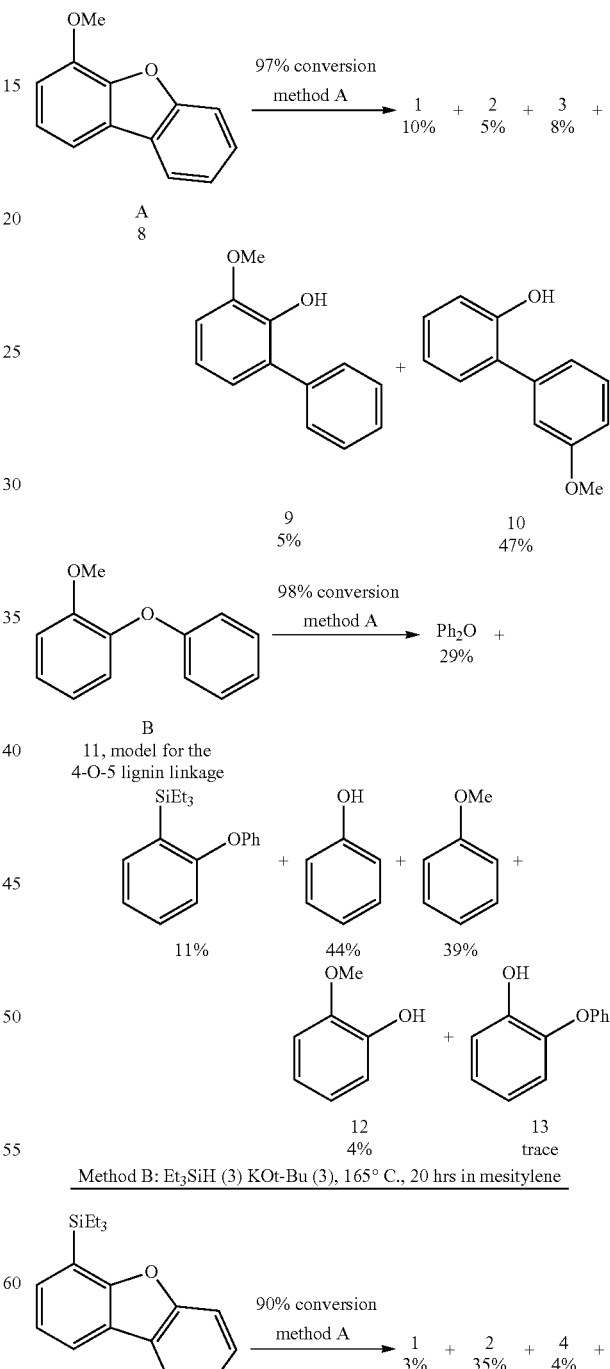

Overall, the selectivity for alkyl C—O bond scission contrasts with that observed in Ni- and borane catalyzed C—O cleavage reactions where aryl C—O reduction occurs. It is also notable that under these conditions only trace amounts of naphthalene ring hydrogenation products were observed, which contrasts with the results of silane-based ionic hydrogenations reported in the literature.

It is instructive to compare the cleavages of methoxysubstituted diaryl ethers 8 and 11 (Scheme 2) with the results presented above. While aryl alkyl ethers show strong preference for the reduction of alkyl oxygen over aryl oxygen bonds, both methoxy substrates in Scheme 2 demonstrate a reversal of regioselectivity, furnishing almost exclusively aryl oxygen bond rupture products. While not intending to be bound by the correctness of this theory, this effect may be attributed to the presence of a donor oxygen atom ortho to the C—O bond undergoing rupture. Supporting this inference is the high selectivity of the reductive ring-opening of dibenzofuran derivative 8 that mainly leads to 10. Likewise, preferred formation of phenol and anisole is observed with similar selectivity over phenols 12 and 13 in the cleavage of lignin model 11. One may speculate that such an effect can be rationalized by the oxygen atom resonance stabilization of the positive charge build up during electrophilic activation of the C—O bond that is being broken. In order to test this hypothesis, compound 3 was subject to the reaction conditions and isolated the ring opened phenols 5 and 6 along with the desilylated products 1 and 2 (Scheme 2, inset C). In the absence of resonance stabilization, the selectivity of cleavage was reversed in favour of isomer 5. It is also worth noting that, as formation of 1 and 2 demonstrates, the silylation reaction is thus reversible under the typical reaction conditions. After having illustrated the potential for the challenging 4-O-5 lignin models 8 and 11, this method was tested with an oli- 0.87-0.74 (m, 6H). $^{13}$C NMR (126 MHz, THF-d8) δ 164.58, 135.52, 130.42, 123.92, 120.08, 109.23, 54.09, 6.93, 3.22.

Example 6.7.2

Triethyl(3-methoxynaphthalen-2-yl)silane

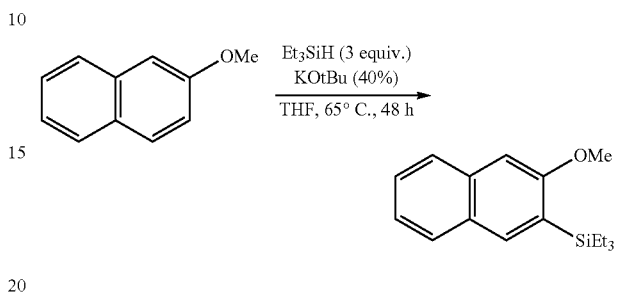

Figure 5A:
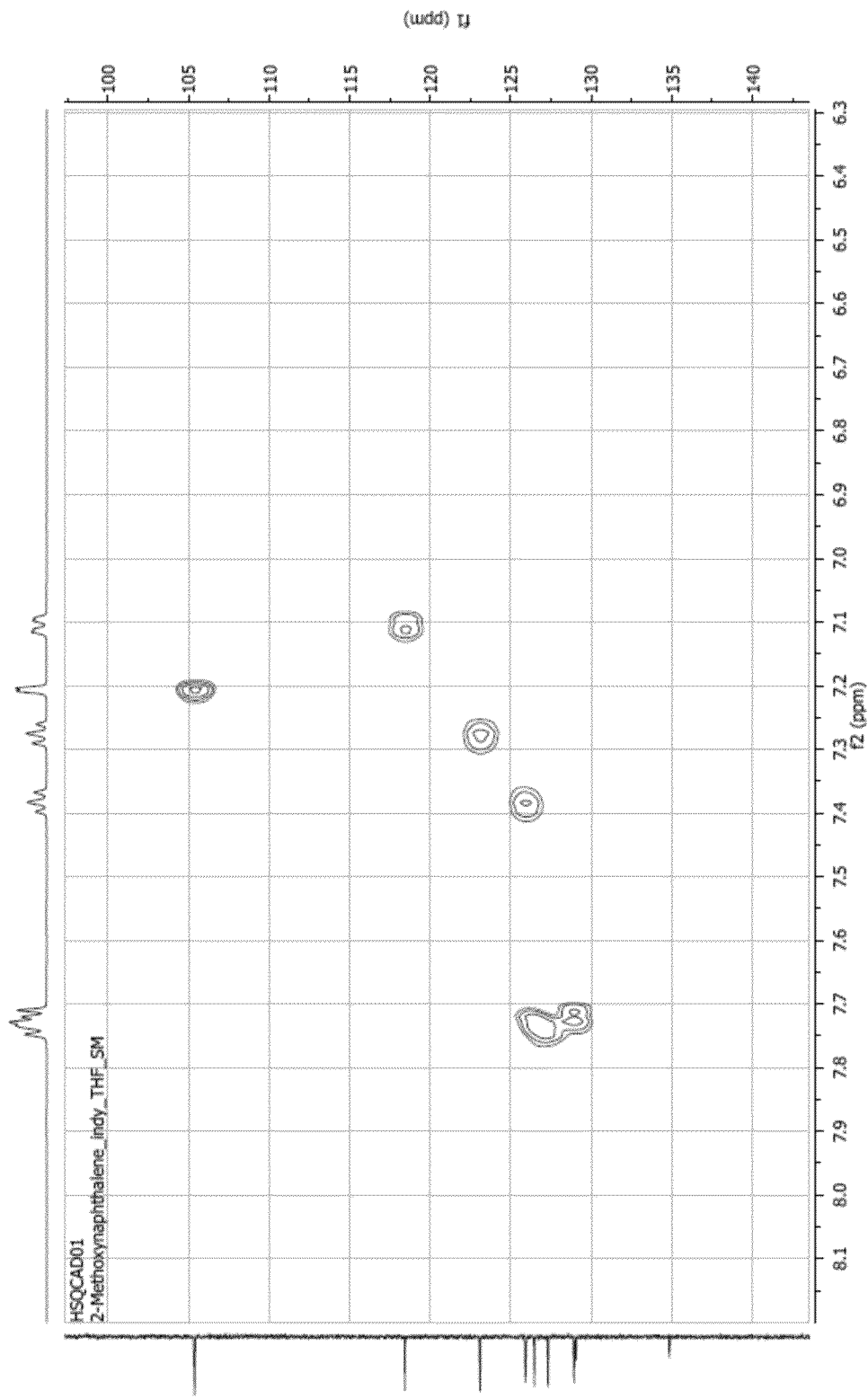
Figure 5B:
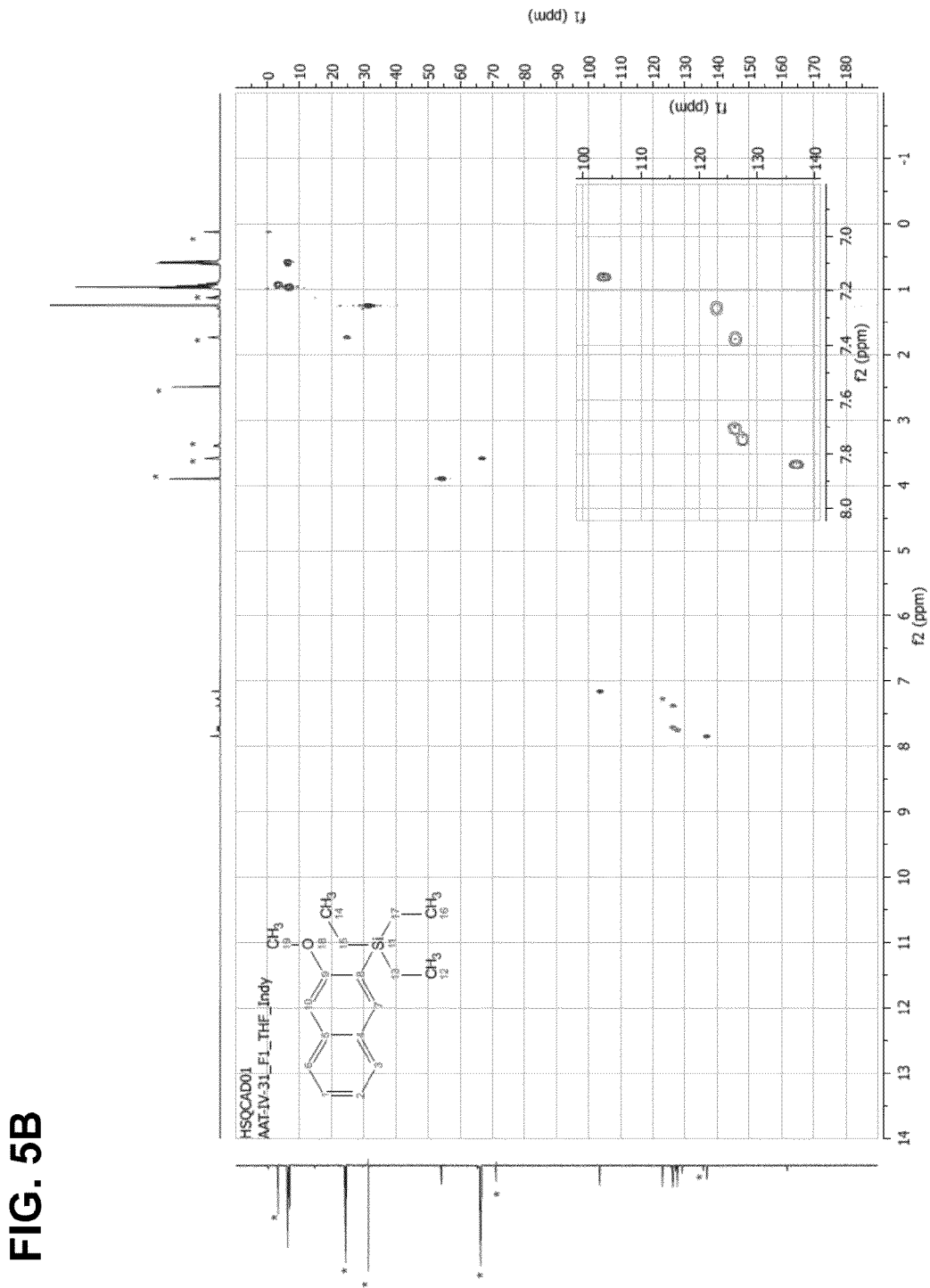

The reaction was conducted according to the General Procedure by heating 2-methoxynaphthalene (79 mg, 0.5 mmol, 1 equiv.), KOt-Bu (19.6 mg, 0.18 mmol, 0.35 equiv.) and Et$_3$SiH (319 microliters, 2.0 mmol, 4 equiv.) in 1 mL of tetrahydrofuran for 48 hours at 65° C. After aqueous work up, the crude reaction mixture was purified by chromatography on silica eluting with hexanes (isochratic) to obtain 79 mg (58%) of the title compound as colourless oil. $^1$H NMR (500 MHz, THF-d8) δ 7.84 (s, 1H), 7.78-7.73 (d, 1H), 7.73-7.68 (d, 1H), 7.38 (ddd, J=8.2, 6.8, 1.3 Hz, 1H), 7.27 (ddd, J=8.1, 6.8, 1.2 Hz, 1H), 7.15 (s, 1H), 3.90 (s, 3H), 1.01-0.90 (m, 9H), 0.68-0.53 (m, 6H). $^{13}$C NMR (126 MHz, THF-d$_8$) δ 163.03, 137.88, 136.83, 130.10, 128.58, 128.09, 127.29, 127.21, 124.03, 104.57, 55.25, 8.02, 7.48. HRMS: [C$_{17}$H$_{24}$OSi] calculated 272.1608, measured 272.1596. The HSQC spectra of the 2-methoxynaphthalene and its reaction product are provided in FIG. 5.

Interestingly, the reaction starting with 1-methoxynaphthalene did not result in silylated product:

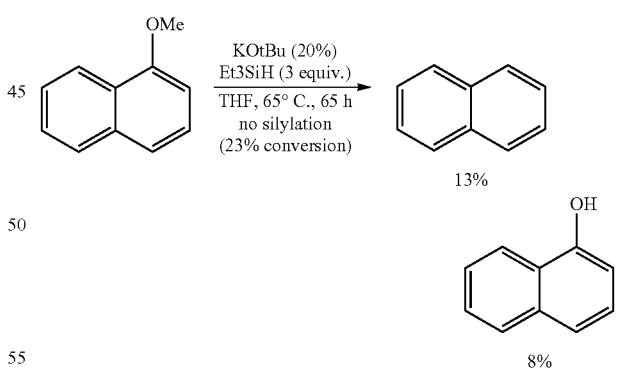

The reaction was conducted according to the General Procedure by heating 1-methoxynaphthalene (79 mg, 0.5 mmol, 1 equiv.), KOt-Bu (11.2 mg, 0.1 mmol, 0.1 equiv) and Et$_3$SiH (240 microliters, 1.5 mmol, 3 equiv.) in 1 mL of tetrahydrofuran for 65 hours at 65° C. The reaction was diluted with diethyl ether (1 mL), quenched with water (0.5 mL) and the organic phase was analyzed by GC-MS, GC-FID and 1H NMR analysis. Analysis by GC-MS and GC-FID (tridecane standard) revealed the formation of aryl C—O cleavage product naphthalene and alkyl C—O bond cleavage product naph-

---

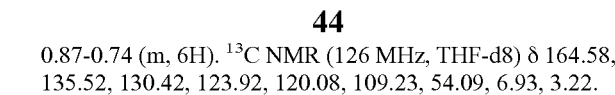

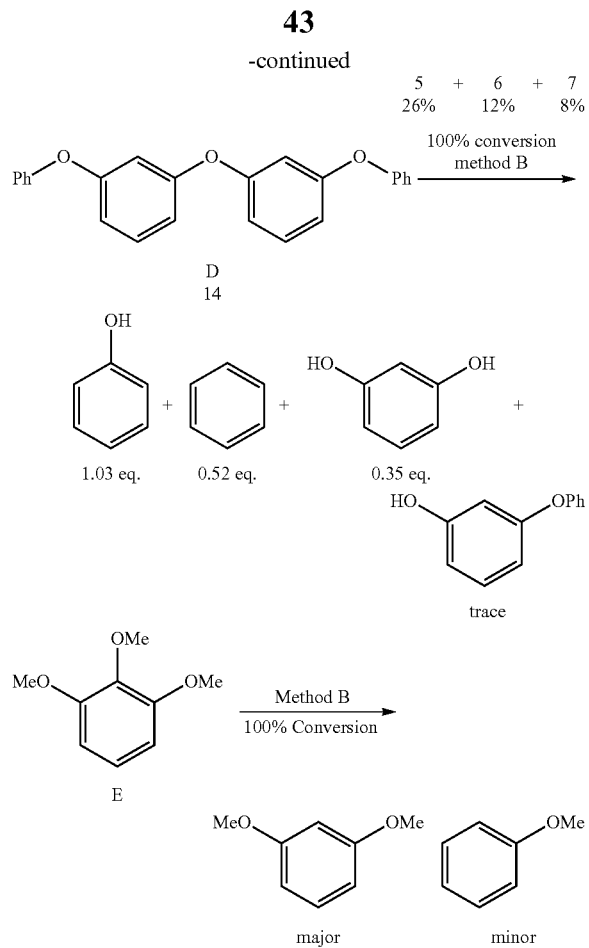

Example 6.7

Silylation of Aryl Alkyl Ethers and Thioethers at Ambient Temperatures

Example 6.7.1

Triethyl(2-methoxyphenyl)silane

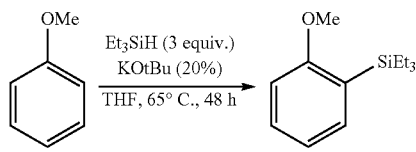

The reaction was conducted according to the General Procedure by heating anisole (54 mg, 0.5 mmol, 1 equiv.), KOt-Bu (11 mg, 0.1 mmol, 0.2 equiv) and Et$_3$SiH (239 microliters, 1.5 mmol, 3 equiv.) in 1 mL of tetrahydrofuran for 65 hours at 65° C. After aqueous work up, the crude reaction mixture was purified by chromatography on silica using hexanes (isochratic) to obtain 59 mg (54%) of the title compound as a colourless oil. $^1$H NMR (500 MHz, THF-d8) δ 7.40-7.17 (m, 2H), 7.01-6.81 (m, 2H), 3.77 (s, 3H), 1.02-0.85 (m, 9H), thiol in 13 and 8 percent yield respectively, notably to the complete exclusion of any silylated species.

Example 6.7.3

Silylation of Diphenyl Ether

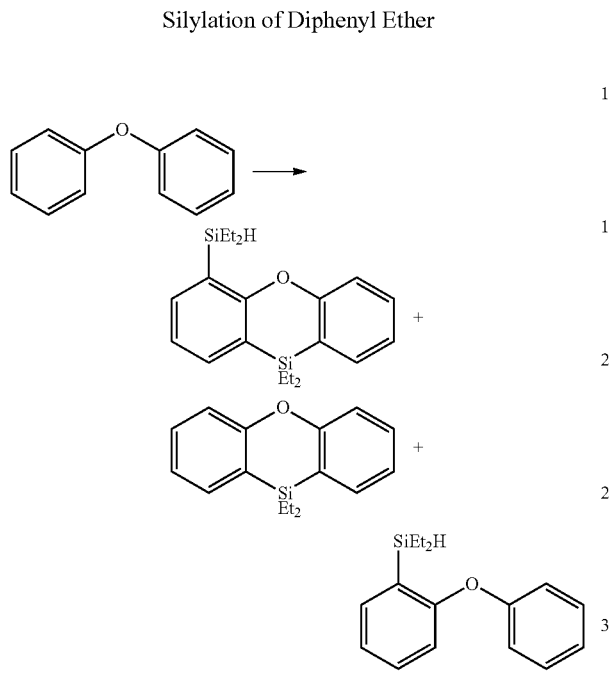

The reaction was conducted according to the General Procedure by heating phenyl ether (85 mg, 0.5 mmol, 1 equiv.), KOt-Bu (11 mg, 0.10 mmol, 0.2 equiv) and $Et_2SiH_2$ (194 microliters, 1.5 mmol, 3 equiv.) in 1 mL of tetrahydrofuran for 65 hours at 65° C. After aqueous work up, the crude reaction mixture was purified by chromatography on silica using an 80:2 mixture of hexanes:triethylamine to obtain 68 mg (20%) of the title compound as a colourless oily solid. $^1$H NMR (500 MHz, THF-$d_8$) δ 7.64-7.57 (m, 2H), 7.55 (dd, J=7.3, 1.8 Hz, 1H), 7.41 (ddd, J=8.3, 7.2, 1.8 Hz, 1H), 7.15 (dd, J=8.3, 1.0 Hz, 1H), 7.14-7.09 (m, 2H), 4.34 (Si—H) (p-like, J=1.2 Hz, 1H), 1.06-0.95 (m, 12H), 0.92-0.82 (m, 8H). $^{13}$C NMR (126 MHz, THF-$d_8$) δ 166.04, 161.43, 139.74, 137.00, 135.55, 135.05, 132.12, 130.19, 128.79, 123.56, 123.37, 118.41, 9.06, 7.93, 6.70, 4.83. HRMS: [$C_{20}H_{27}OSi_2$] calculated 339.1601, measured 339.1607

Figure 6A:
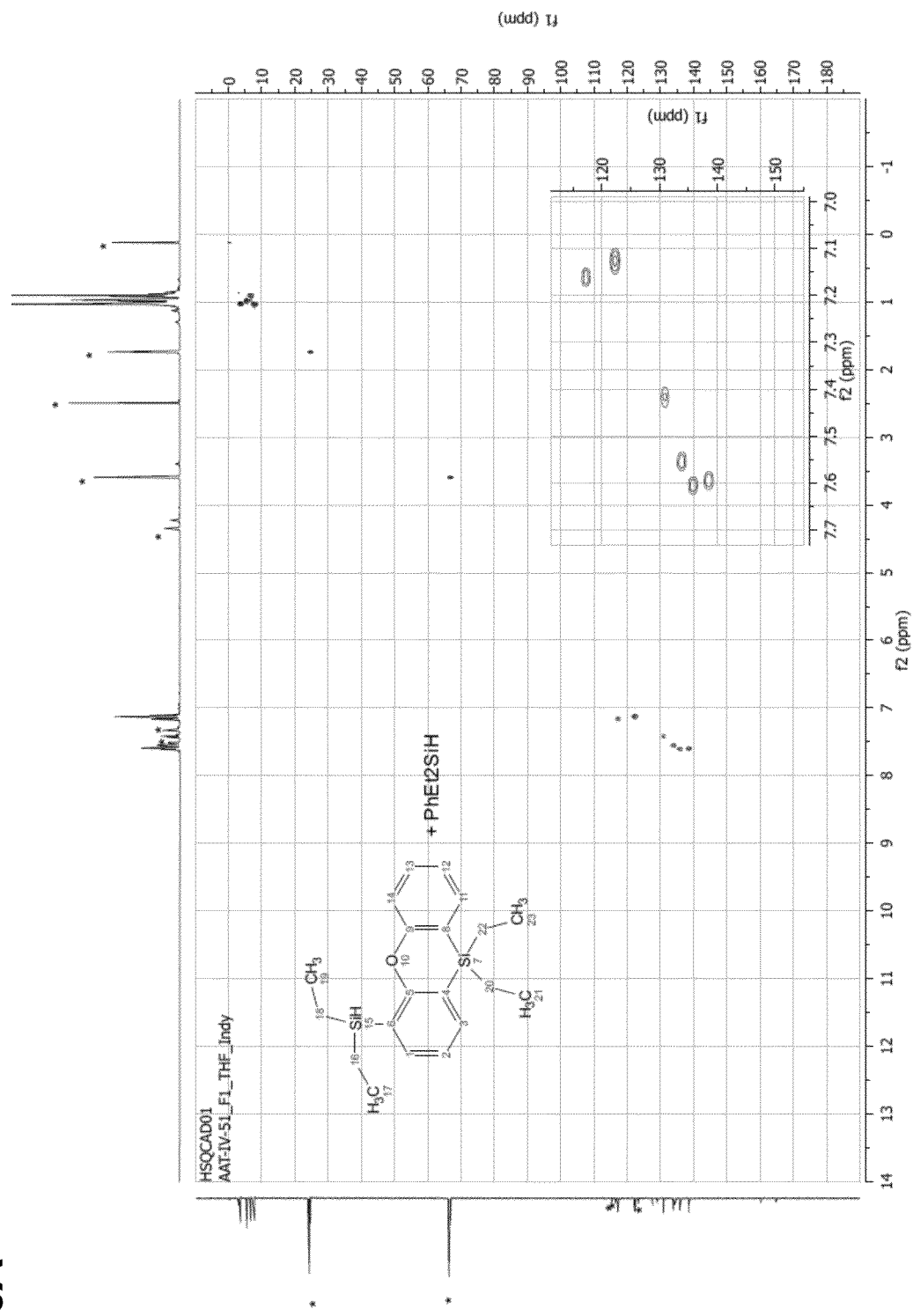
FIGS. 6A and B are the HSQC spectra of two of the products of the reaction between diphenyl ether and diethyl silane, as described in Example 6.7.3.
Figure 6B:
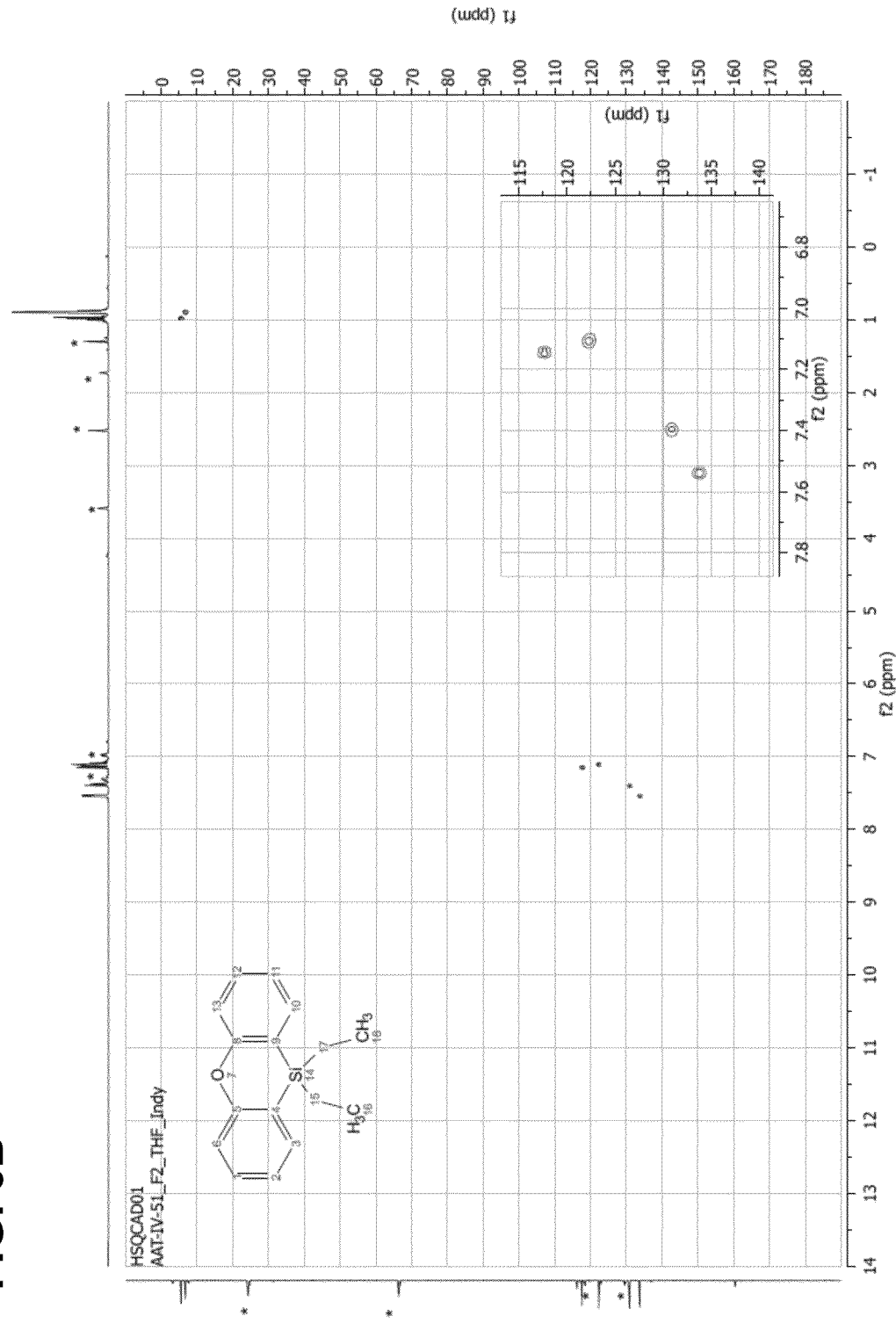

A second fraction of the reaction mixture yielded 34 mg (39%) of the cyclized derivative. $^1$H NMR (500 MHz, THF-$d_8$) δ 7.57-7.50 (m, 2H), 7.40 (ddd, J=8.3, 7.2, 1.8 Hz, 2H), 7.15 (dd, J=8.6, 0.7 Hz, 2H), 7.11 (td, J=7.2, 1.0 Hz, 2H), 0.99-0.95 (m, 4H), 0.92-0.86 (m, 6H). $^{13}$C NMR (126 MHz, THF-$d_8$) δ 161.54, 134.96, 132.07, 123.41, 118.80, 117.39, 7.95, 6.72. HRMS: [$C_{16}H_{19}OSi$] calculated 255.1205, measured 255.1206. The HSQC spectra of these reaction products are provided in FIGS. 6A and 6B.

A third fraction was obtained, containing a product in low yield (ca. 7%) whose spectral characteristics appear to be consistent with the structure of the monosilylated product shown above.

Example 6.7.4

Triethyl((phenylthio)methyl)silane

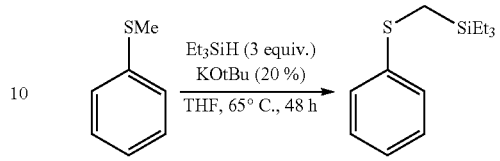

Figure 7A:
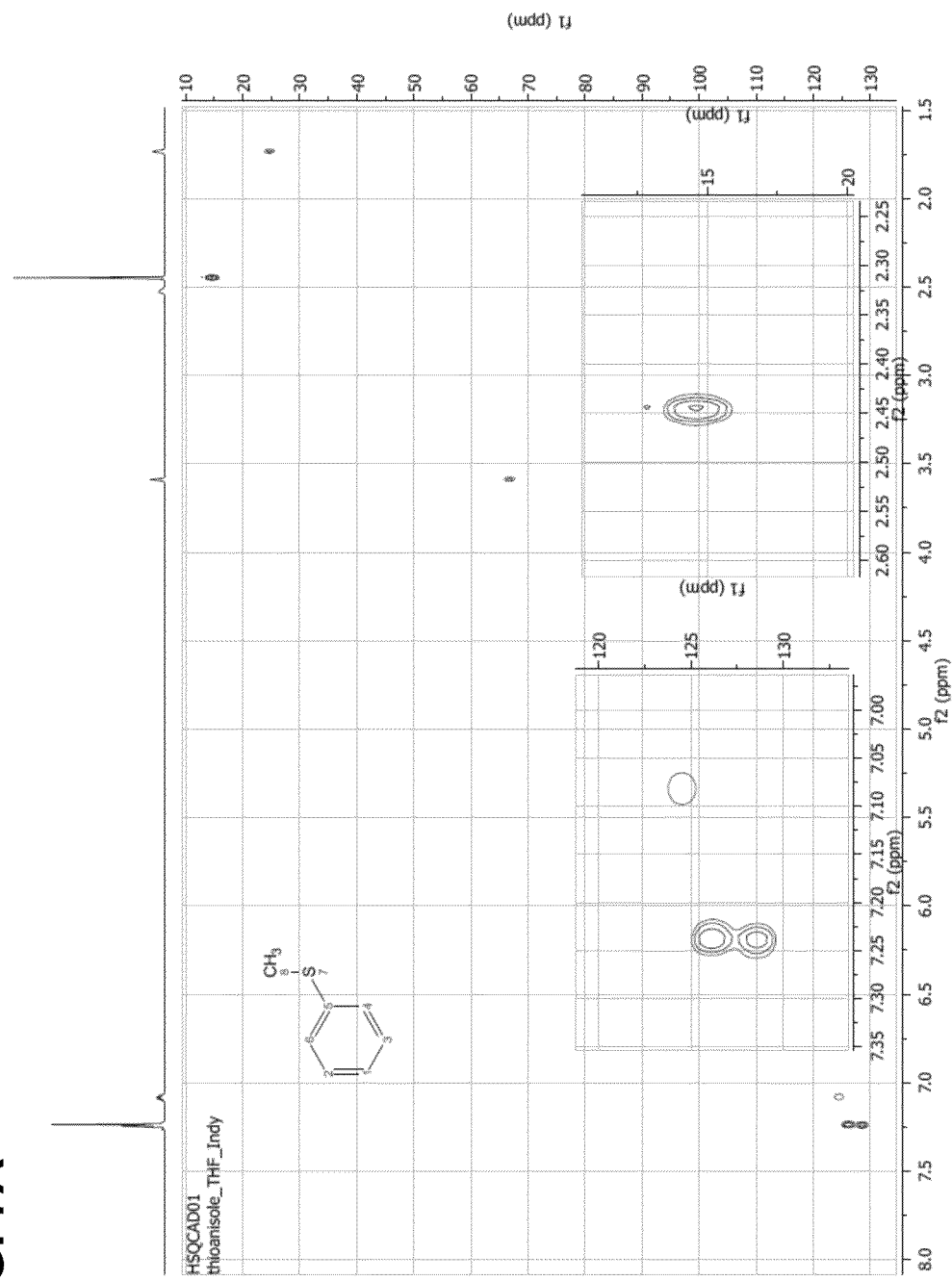
Figure 7B:
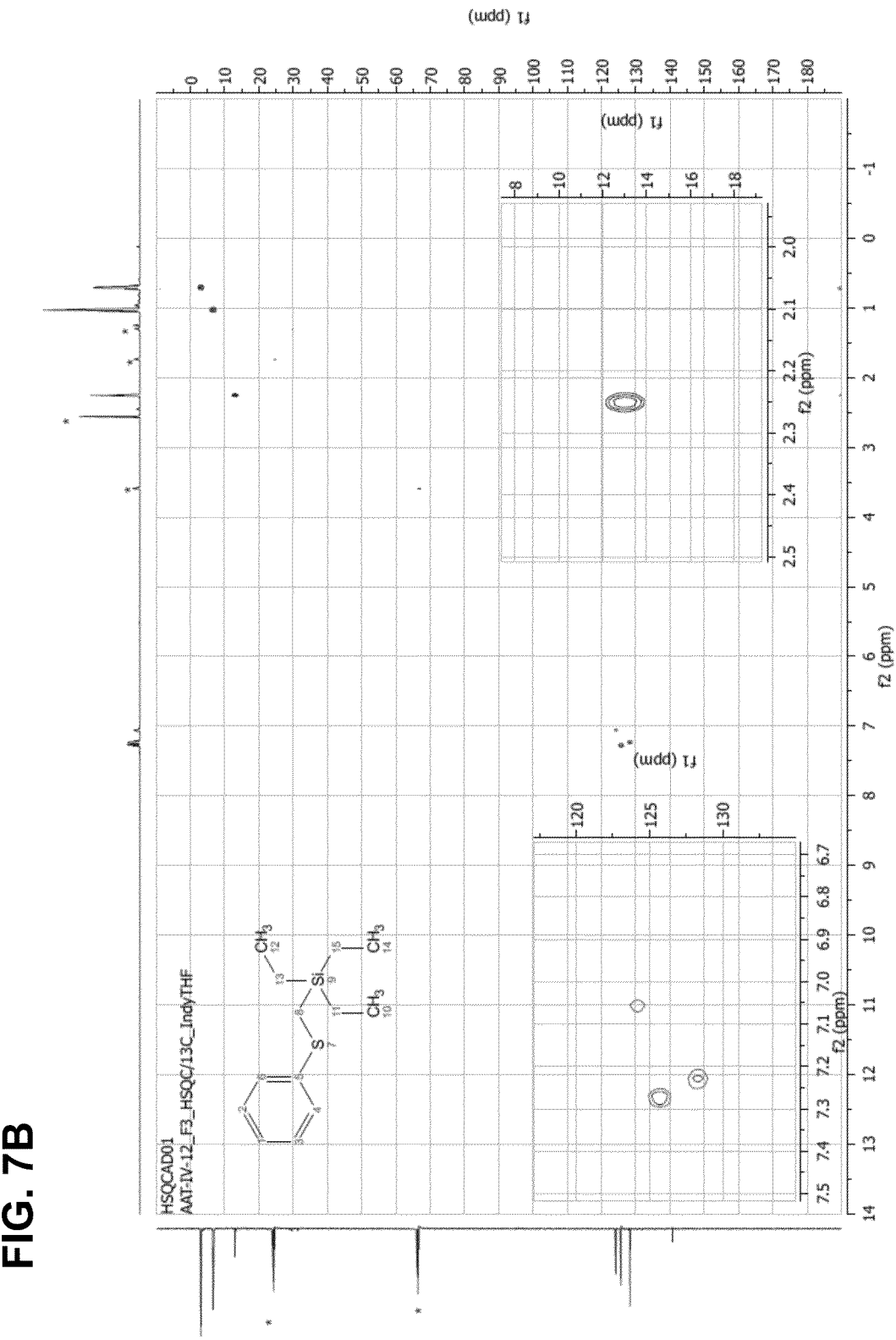

The reaction was conducted according to the General Procedure by heating thioanisole (62 mg, 0.5 mmol, 1 equiv.), KOt-Bu (11 mg, 0.1 mmol, 0.2 equiv) and $Et_3SiH$ (239 microliters, 1.5 mmol, 3 equiv.) in 1 mL of tetrahydrofuran for 65 hours at 65° C. After aqueous work up, the crude reaction mixture was purified by chromatography on silica using hexanes (isochratic) to obtain 81 mg (68%) of the title compound as a colourless oil. $^1$H NMR (500 MHz, THF-d8) δ 7.31-7.26 (m, 2H), 7.25-7.19 (m, 2H), 7.11-7.01 (m, 1H), 1.03 (t, J=7.9 Hz, 9H), 0.78-0.60 (m, 6H). $^{13}$C NMR (126 MHz, THF-d8) δ 140.73, 128.31, 125.69, 124.19, 13.01, 6.62, 3.06. HRMS: [$C_{13}H_{21}SSi$] calculated 237.1140, measured 237.1133. The HSQC spectra of the thioanisole and its reaction product as provided in FIGS. 7A and 7B.

Example 6.8

Experiments with C—N and C—S Heteroaryl Compounds at Elevated Temperatures

Experiments were also conducted with C—N and C—S heteroaryl compounds. In the case of compounds comprising C—N bonds, reactivity appeared to be similar to that seen for C—O bonds, and it is reasonably expected that the wide ranging methods used for the latter will result in results in similar reactivity in the former:

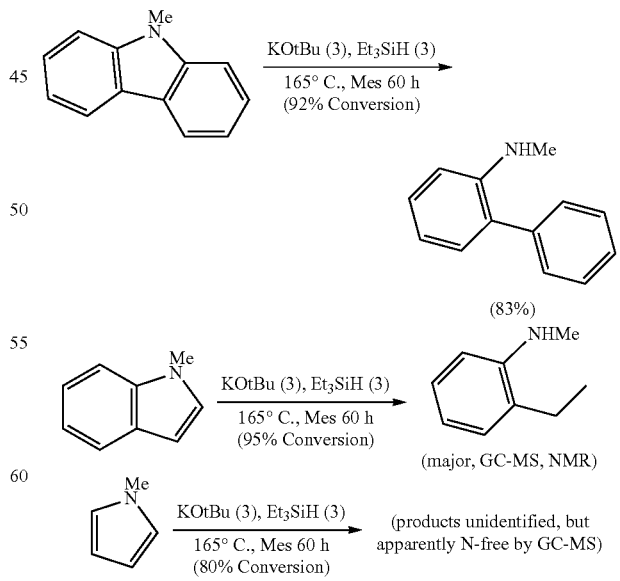

In the case of compounds comprising C—S compounds, the methods appear to generally result in complete desulfurization of the molecules. This difference in reactivities may reflect the differences in bond energies between the C—O, C—N, and C—S bonds (compare C—X bond dissociation energies in phenol (111), aniline (104), and thiophenol (85, all in kcal/mol). Of particular interest is the desulfurization of even hindered dibenzothiophenes under relatively mild conditions. In none of these conversions were single C—S products detected:

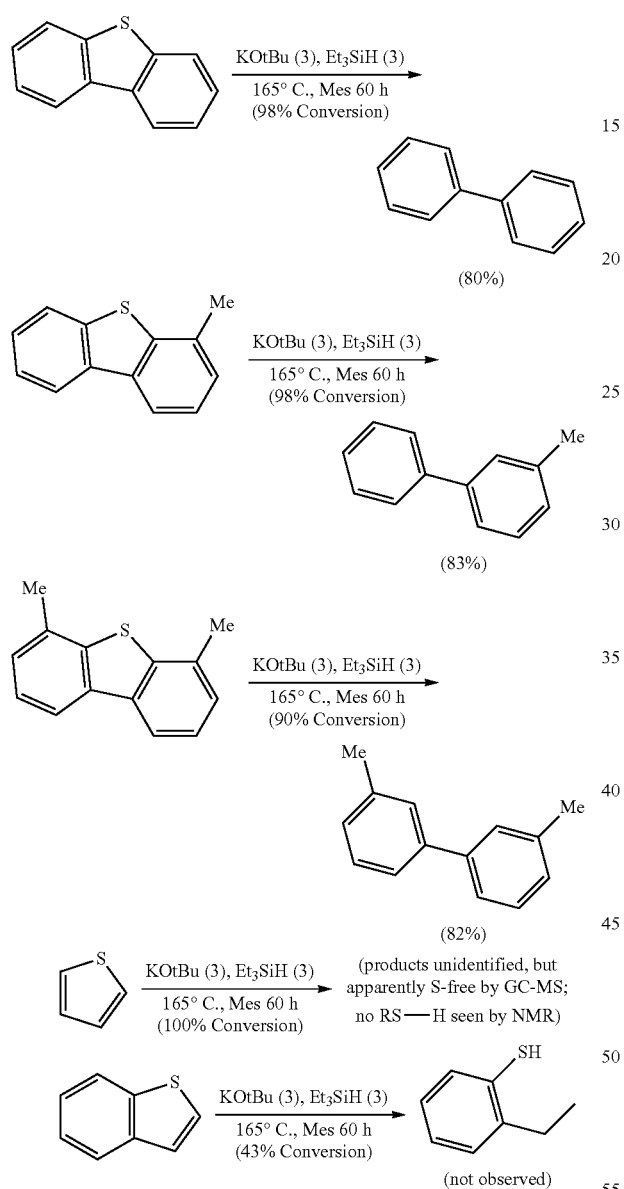

Example 6.9

Experiments with Heteroaryl Compounds at Ambient Temperatures

A series of experiments were done at ambient (65° C. or below) to test the regioselectivity of several of the more reactive heteroaryl compounds. The test conditions and results are shown below. Yields for all reactions are either by isolation (chromatography on silica gel, or bulb-to-bulb distillation) or by GC-FID or NMR analysis using internal standard for quantification. Note that C-3 silylated heteroarenes were found in some cases to be prone to protodelilylation on silica gel. In these cases, bulb-to-bulb distillation was used or, alternatively, silica gel chromatography with ca. 3% triethyl amine added to the eluent, or a combination of both methods. Products were identified as indicated by $^1$H, $^{13}$C NMR, and Heteronuclear Single Quantum Coherence (HSQC) spectroscopy, or GC-MS, or a combination of both, where possible using comparisons with authentic samples.

Example 6.9.1

1-methyl-2-(triethylsilyl)-1H-indole

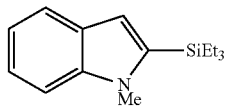

Figure 8:
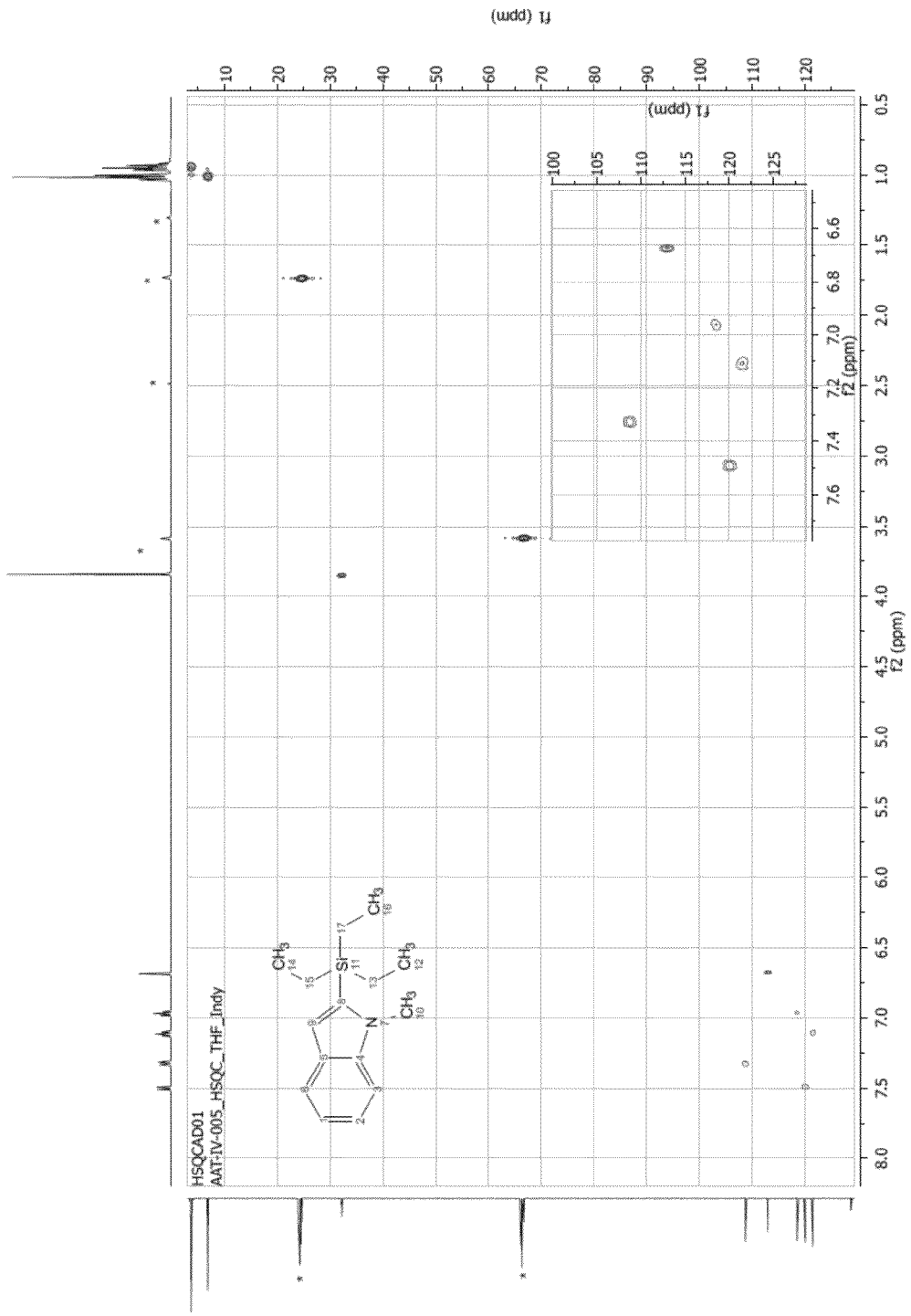

The reaction was conducted according to the General Procedure by heating N-methylindole (66 mg, 0.5 mmol, 1 equiv.), KOt-Bu (8.4 mg, 0.08 mmol, 0.15 equiv.) and Et$_3$SiH (239 microliters, 1.5 mmol, 3 equiv.) in 1 mL of tetrahydrofuran for 48 hours at 23° C. After aqueous work up, the crude reaction mixture was purified by chromatography on silica eluting with hexanes (isochratic) to obtain 88 mg (72%) of the title compound as a colourless oil. $^1$H NMR (500 MHz, THF-d8) δ 7.50 (dt, J=7.9, 1.0 Hz, 1H), 7.32 (dq, J=8.3, 0.9 Hz, 1H), 7.11 (ddd, J=8.2, 6.9, 1.2 Hz, 1H), 6.97 (ddd, J=7.9, 7.0, 0.9 Hz, 1H), 6.68 (d, J=0.9 Hz, 1H), 3.84 (s, 3H), 1.06-0.98 (m, 9H), 0.98-0.92 (m, 6H). $^{13}$C NMR (126 MHz, THF-d8) δ 140.48, 136.86, 128.70, 121.44, 120.05, 118.51, 112.96, 108.71, 32.18, 6.83, 3.63. The HSQC spectrum of this reaction product as provided in FIG. 8.

Example 6.9.2

1-methyl-3-(triethylsilyl)-1H-indole

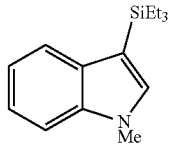

Figure 9:
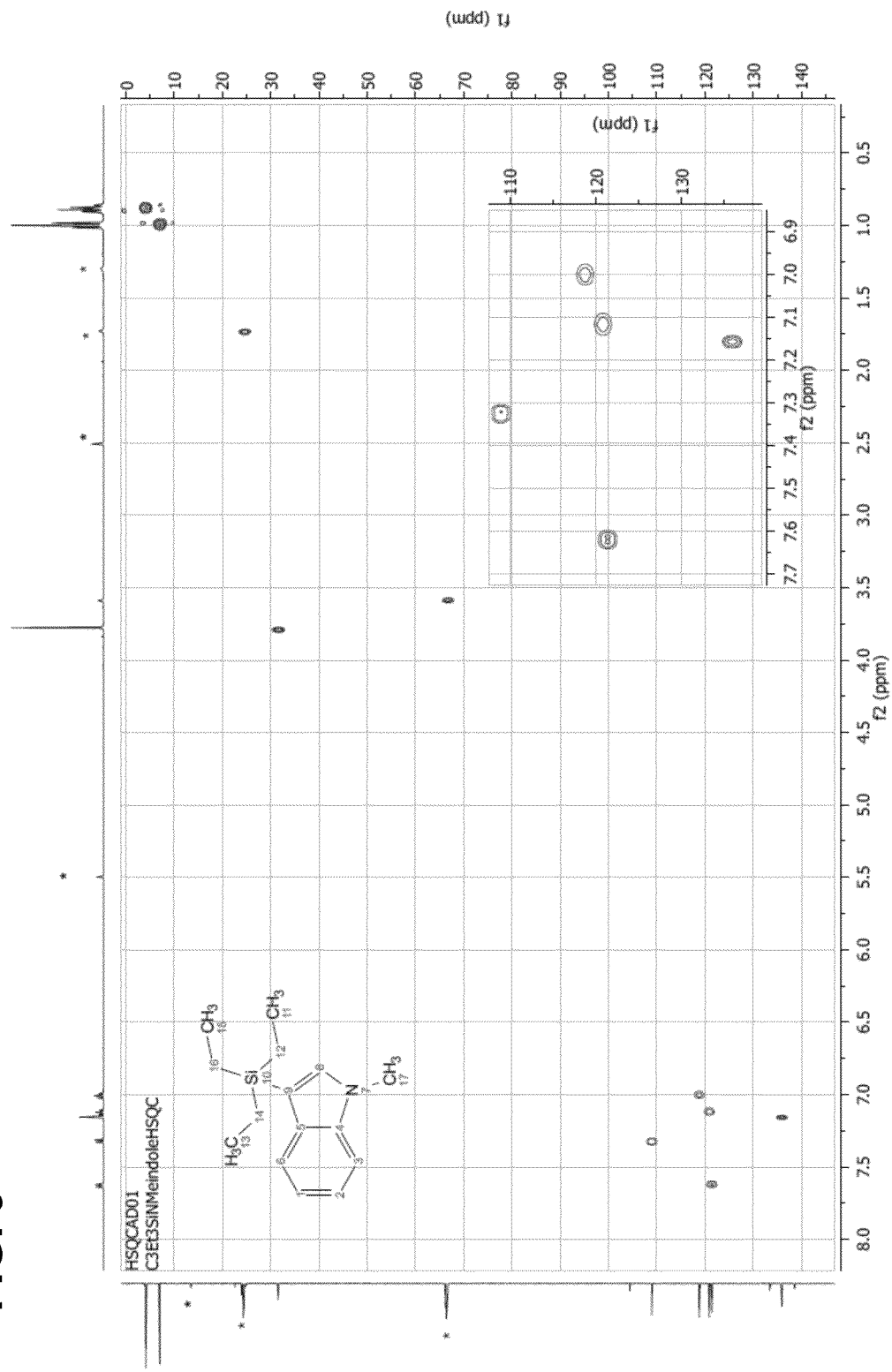

The reaction was conducted according to the General Procedure by heating N-methylindole (66 mg, 0.5 mmol, 1 equiv.), KOt-Bu (56 mg, 0.5 mmol, 1 equiv.) and Et$_3$SiH (88 microliters, 0.55 mmol, 1.1 equiv.) in 1 mL of tetrahydrofuran for 312 hours at 23° C. After aqueous work up, the crude reaction mixture was purified by chromatography on silica eluting with 95:5 hexanes:NEt$_3$ (isochratic) to obtain 103 mg (84%) of the title compound as a colourless oil. $^1$H NMR (500 MHz, THF-d8) δ 7.63 (dt, J=7.9, 1.0 Hz, 1H), 7.32 (dt, J=8.2, 0.9 Hz, 1H), 7.15 (s, 1H), 7.12 (ddd, J=8.2, 7.0, 1.1 Hz, 1H), 7.01 (ddd, J=8.0, 7.0, 1.1 Hz, 1H), 3.78 (s, 3H), 1.06-0.95 (m, 9H), 0.95-0.83 (m, 6H). $^{13}$C NMR (126 MHz, THF-d8) δ 138.63, 135.94, 133.37, 121.44, 120.88, 118.79, 108.96, 104.39, 31.61, 7.04, 4.11. The HSQC spectrum of this reaction product as provided in FIG. 9.

Example 6.9.3

2-(ethyldimethylsilyl)-1-methyl-1H-indole

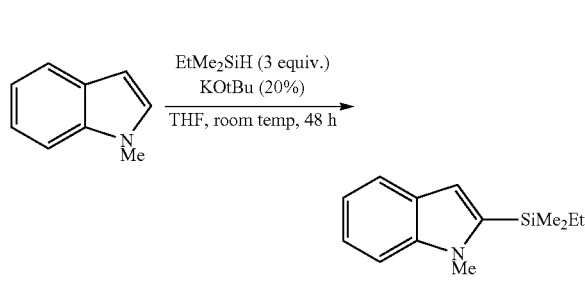

The reaction was conducted according to the General Procedure by heating N-methylindole (62 mg, 0.5 mmol, 1 equiv.), KOt-Bu (11 mg, 0.1 mmol, 0.2 equiv) and EtMe$_2$SiH (198 microliters, 1.5 mmol, 3 equiv.) in 1 mL of tetrahydrofuran for 48 hours at 23° C. After aqueous work up, the crude reaction mixture was purified by chromatography on silica using hexanes (isochratic) to obtain 80 mg (74%) of the title compound as a colourless oil. $^1$H NMR (500 MHz, THF-d8) δ 7.48 (d, J=7.9 Hz, 1H), 7.31 (dd, J=8.4, 1.0 Hz, 1H), 7.10 (ddd, J=8.2, 6.9, 1.2 Hz, 1H), 6.95 (ddd, J=7.9, 6.9, 0.9 Hz, 1H), 6.64 (d, J=0.9 Hz, 1H), 3.84 (s, 3H), 1.05-0.95 (m, 3H), 0.89 (d, J=7.9 Hz, 2H), 0.38 (s, 6H). $^{13}$C NMR (126 MHz, THF-d8) δ 140.45, 138.94, 128.58, 121.45, 120.10, 118.51, 113.53, 111.90, 108.67, 32.17, 7.37, 6.77, −3.67. HRMS: [C$_{13}$H$_{19}$NSi] calculated 217.1280; measured 217.1287.

Example 6.9.4

1-benzyl-2-(triethylsilyl)-1H-indole

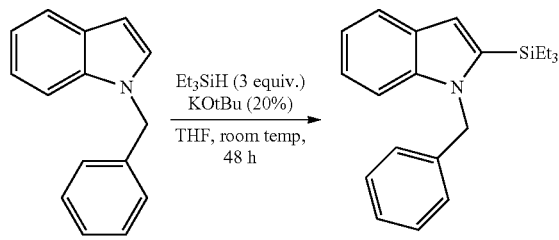

The reaction was conducted according to the General Procedure by heating 1-benzylindole (62 mg, 0.5 mmol, 1 equiv.), KOt-Bu (11 mg, 0.1 mmol, 0.2 equiv) and Et$_3$SiH (239 microliters, 1.5 mmol, 3 equiv.) in 1 mL of tetrahydrofuran for 48 hours at 23° C. After aqueous work up, the crude reaction mixture was purified by chromatography on silica using hexanes (isochratic) to obtain 50 mg (31%) of the title compound as a colourless oily solid. $^1$H NMR (500 MHz, THF-d8) δ 7.56 (ddd, J=7.7, 1.3, 0.7 Hz, 1H), 7.25-7.07 (m, 4H), 7.02 (ddd, J=8.2, 6.9, 1.3 Hz, 1H), 6.98 (ddd, J=7.9, 6.9, 1.1 Hz, 1H), 6.92-6.86 (m, 2H), 6.80 (d, J=0.9 Hz, 1H), 5.52 (s, 2H), 1.06-0.88 (m, 9H), 0.85-0.69 (m, 6H).

Example 6.9.5

1-benzyl-2-(ethyldimethylsilyl)-1H-indole

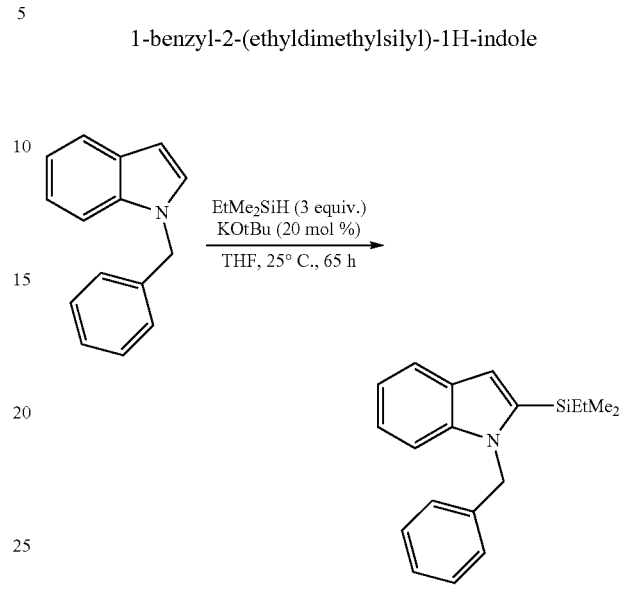

The reaction was conducted according to the General Procedure by heating 1-benzylindole (104 mg, 0.5 mmol, 1 equiv.), KOt-Bu (17 mg, 0.15 mmol, 0.3 equiv) and EtMe$_2$SiH (198 microliters, 1.5 mmol, 3 equiv.) in 1 mL of tetrahydrofuran for 65 hours at 25° C. After aqueous work up, the crude reaction mixture was purified by chromatography on silica using an 80:1:4 mixture of hexanes:diethyl ether:triethylamine respectively to obtain 107 mg (73%) of the title compound as a colourless oil. $^1$H NMR (500 MHz, THF-d$_8$) δ 7.55 (ddd, J=7.7, 1.4, 0.8 Hz, 1H), 7.22-7.16 (m, 2H), 7.16-7.09 (m, 2H), 7.02 (ddd, J=8.2, 6.9, 1.4 Hz, 1H), 6.97 (ddd, J=8.0, 6.9, 1.2 Hz, 1H), 6.86 (ddd, J=7.2, 1.3, 0.7 Hz, 2H), 6.78 (d, J=0.9 Hz, 1H), 5.51 (d, J=1.1 Hz, 2H), 0.95-0.90 (m, 3H), 0.24 (s, 6H). $^{13}$C NMR (126 MHz, THF-d8) δ 141.31, 140.50, 139.94, 130.09, 129.39, 127.90, 126.71, 122.96, 121.45, 120.10, 113.93, 110.81, 50.62, 8.50, 7.93, −2.40. HRMS: [C$_{19}$H$_{23}$NSi] calculated 293.1600, measured 293.1590.

Example 6.9.6

1-methyl-2-(triethylsilyl)-1H-pyrrolo[2,3-b]pyridine

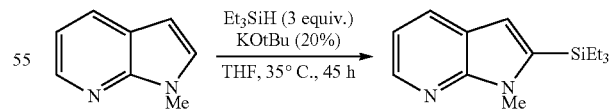

Figure 10:
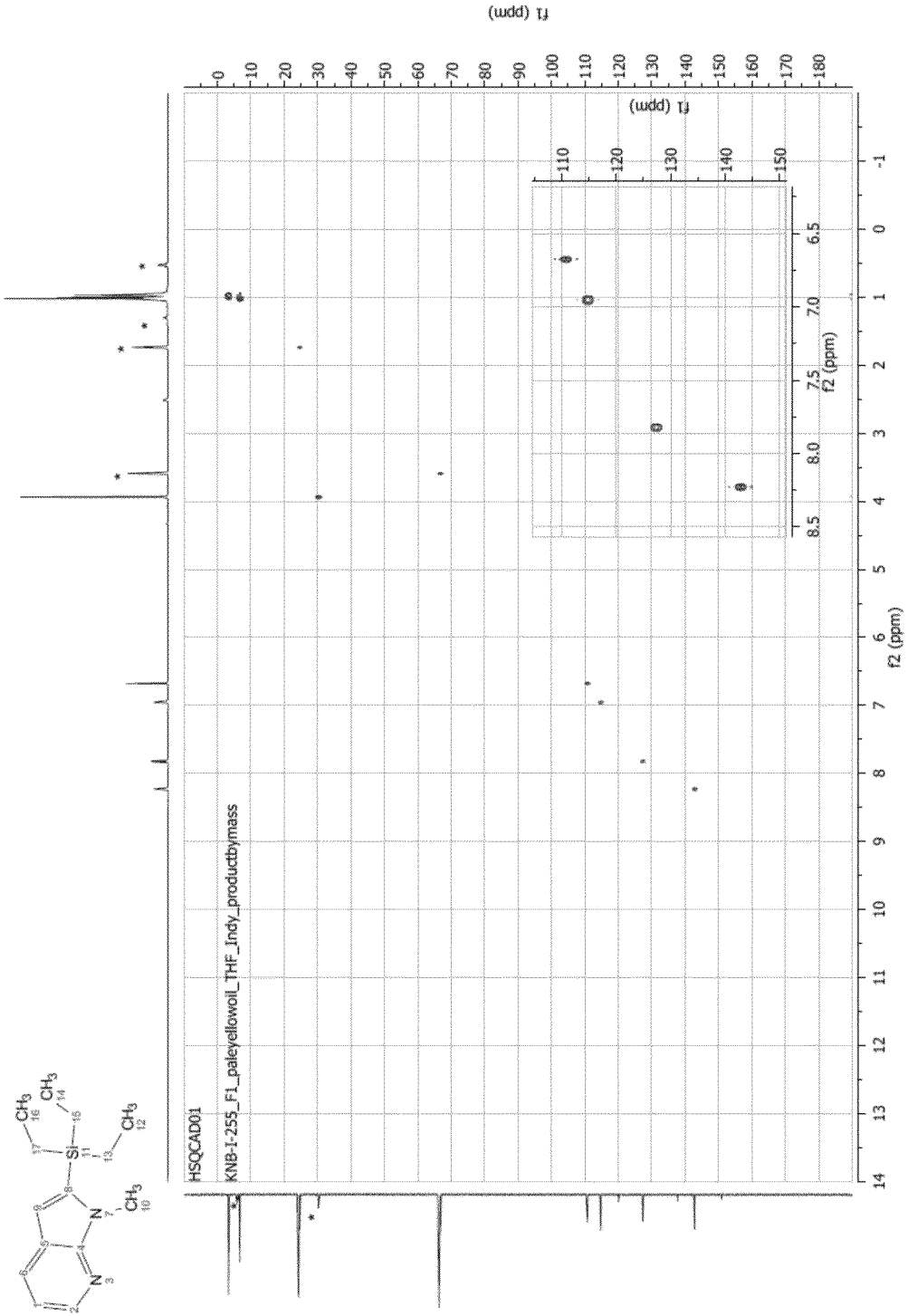

The reaction was conducted according to the General Procedure by heating N-methyl-1H-pyrrolo[2,3-b]pyridine (66 mg, 0.5 mmol, 1 equiv.), KOt-Bu (11 mg, 0.1 mmol, 0.2 equiv.) and Et$_3$SiH (239 microliters, 1.5 mmol, 3 equiv.) in 1 mL of tetrahydrofuran for 45 hours at 35° C. After aqueous work up, the crude reaction mixture was purified by chromatography on silica using step gradient elution (starting with 100% hexanes and increasing the polarity of the eluent stepwise to 30% EtOAc in Hexanes) to obtain 89 mg (73%) of the title compound as a pale yellow oil. $^1$H NMR (500 MHz, THF-d8) δ 8.45-7.95 (m, 1H), 7.97-7.66 (m, 1H), 6.95 (dd, J=7.7, 4.6 Hz, 1H), 6.68 (s, 1H), 3.94 (s, 2H), 1.05-1.00 (m, 9H), 0.97 (td, J=7.1, 1.7 Hz, 6H). $^{13}$C NMR (126 MHz, THF-d8) δ 150.95, 142.87, 137.82, 127.38, 120.13, 114.79, 110.76, 30.27, 6.74, 3.31. HRMS: [$C_{14}H_{23}N_2Si$] calculated 247.1642, measured 247.1631. The HSQC spectrum of this reaction product as provided in FIG. 10.

Example 6.9.7

Effect of Tetramethylethylenediamine (TMEDA)

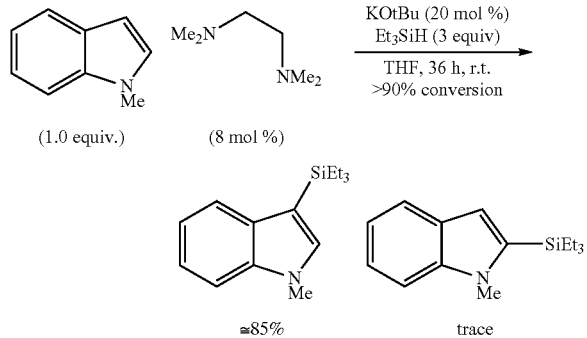

Example 6.9.8

Silylation of N-methyl-2-methylindole

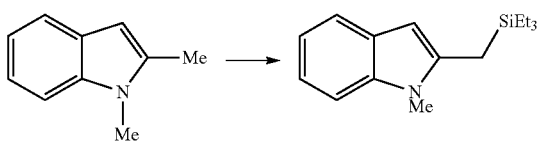

Figure 11:
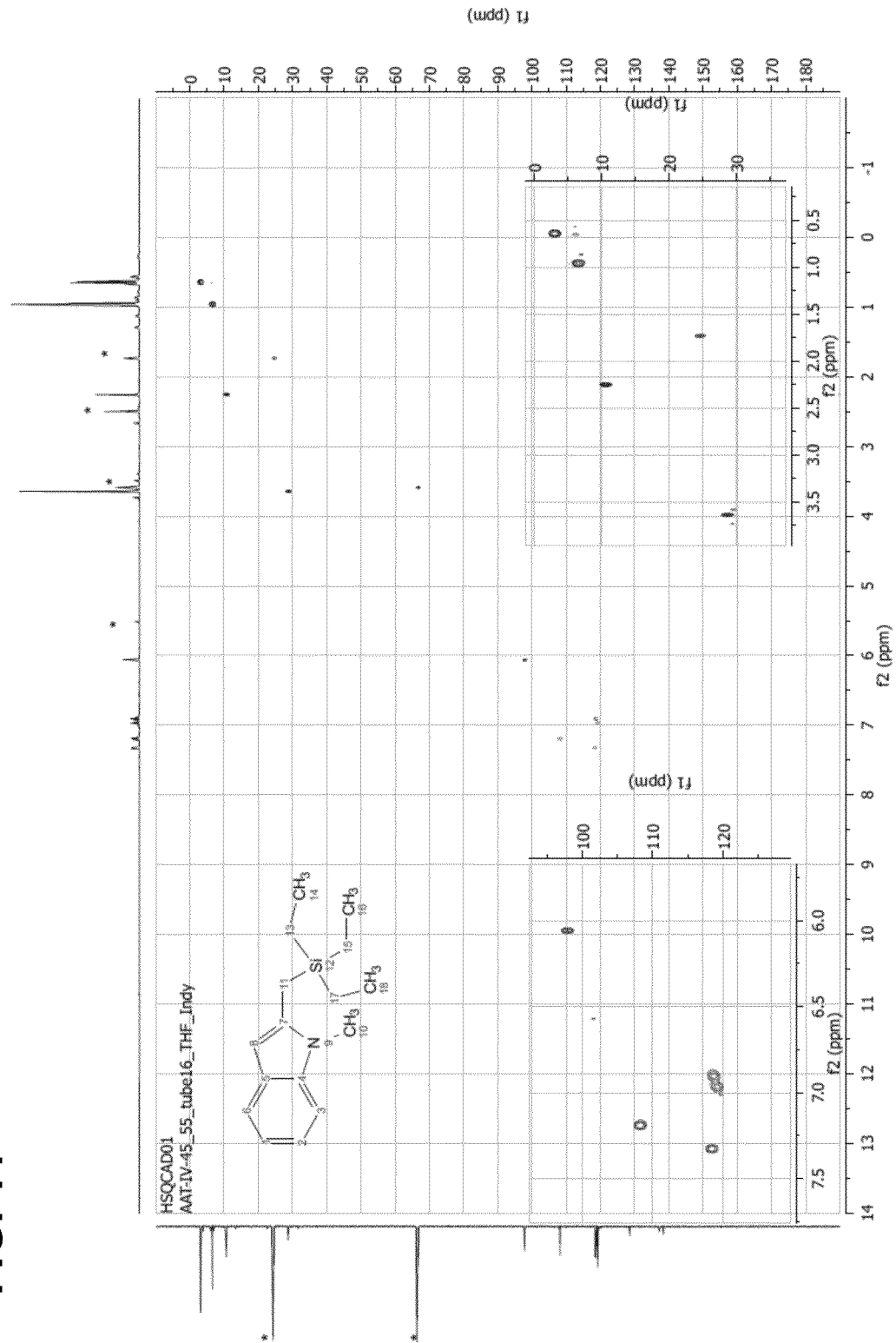

The reaction was conducted according to the General Procedure by heating 1,2-dimethylindole (73 mg, 0.5 mmol, 1 equiv.), KOt-Bu (17 mg, 0.15 mmol, 0.3 equiv) and Et$_3$SiH (319 microliters, 2.0 mmol, 4 equiv.) in 1 mL of tetrahydrofuran for 65 hours at 65° C. After aqueous work up, the crude reaction mixture was purified by chromatography on silica using an 80:1:4 mixture of hexanes:diethyl ether:triethylamine respectively to obtain 74 mg (57%) of the title compound as a colourless oil. $^1$H NMR (500 MHz, THF-d$_8$) δ 7.35-7.29 (m, 1H), 7.19 (dd, J=8.1, 0.9 Hz, 1H), 6.97 (ddd, J=8.2, 7.1, 1.2 Hz, 1H), 6.90 (ddd, J=8.0, 7.1, 1.1 Hz, 1H), 6.06 (d, J=0.8 Hz, 1H), 3.64 (s, 3H), 2.25 (d, J=0.7 Hz, 2H), 0.96 (t, J=7.9 Hz, 9H), 0.71-0.58 (m, 6H). $^{13}$C NMR (126 MHz, THF-d$_8$) δ 139.50, 138.30, 129.69, 120.24, 119.70, 119.47, 109.27, 98.96, 29.75, 11.73, 7.62, 4.16. HRMS: [$C_{16}H_{25}NSi$] calculated 259.1756, measured 259.1754. The HSQC spectrum of this reaction product as provided in FIG. 11.

Example 6.9.9

Silylation of N-methyl pyrrole

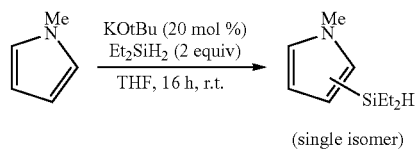

(single isomer)

Example 6.9.10

9,9-diethyl-9H-benzo[d]pyrrolo[1,2-a][1,3]azasilole

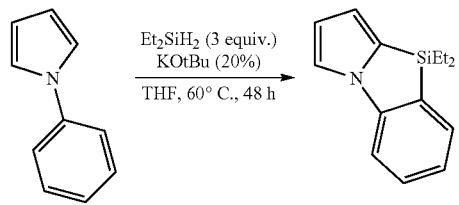

Figure 12:
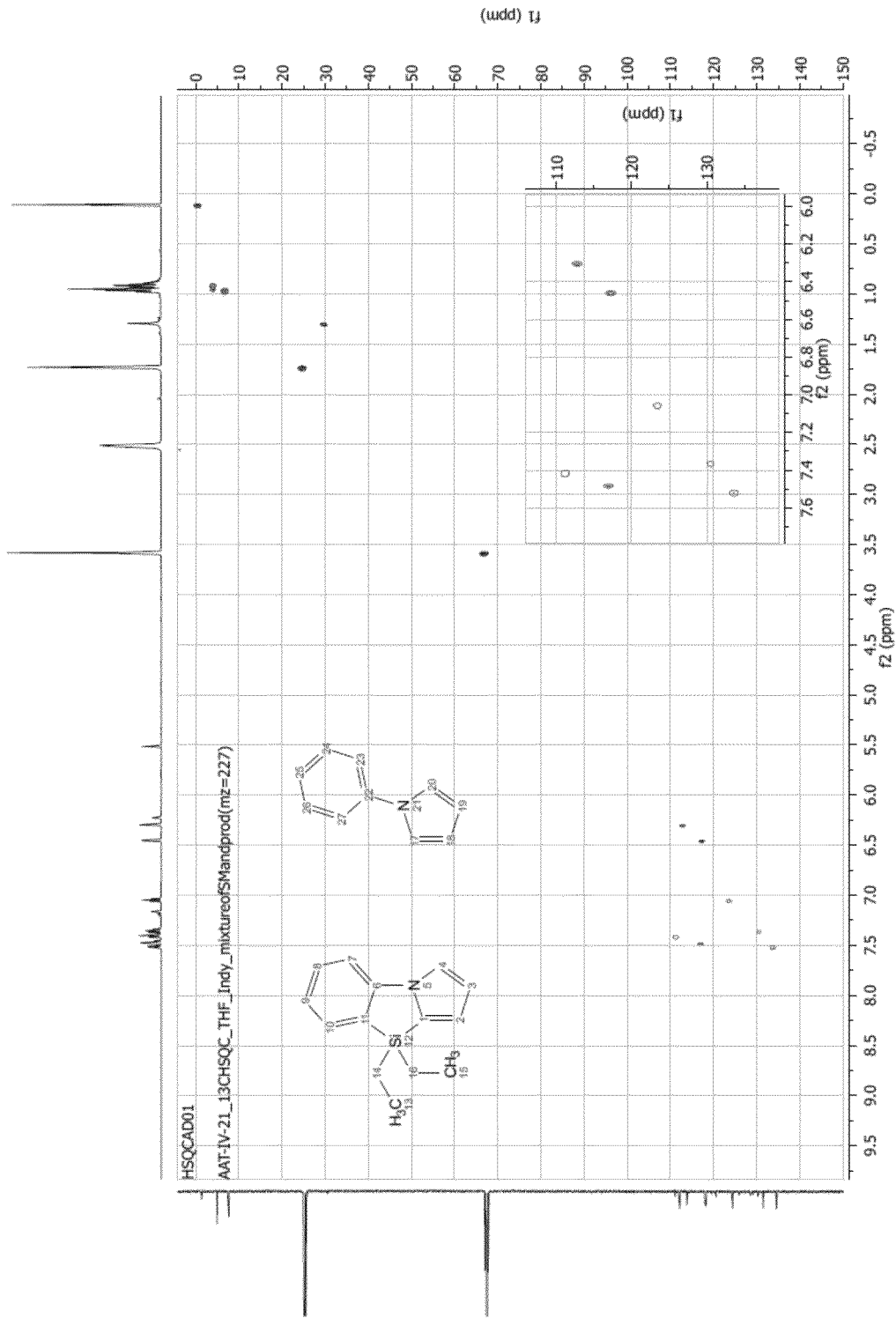

The reaction was conducted according to the General Procedure by heating 1-phenylpyrrole (161 mg, 0.5 mmol, 1 equiv.), KOt-Bu (11 mg, 0.1 mmol, 0.2 equiv) and Et$_2$SiH$_2$ (194 microliters, 1.5 mmol, 3 equiv.) in 1 mL of tetrahydrofuran for 65 hours at 60° C. After aqueous work up, the crude reaction mixture was purified by chromatography on silica using hexanes (isochratic) to obtain 97 mg (85%) of a mixture containing approximately a 7:1 mixture of the title compound and the starting material as a colourless oily solid. $^1$H NMR (500 MHz, THF-d8) δ 7.51 (ddd, J=7.1, 1.5, 0.6 Hz, 1H), 7.47 (dd, J=2.6, 1.1 Hz, 1H), 7.43-7.39 (m, 1H), 7.38-7.33 (m, 1H), 7.04 (td, J=7.2, 1.0 Hz, 1H), 6.45 (dd, J=3.2, 1.1 Hz, 1H), 6.29 (t, J=2.9 Hz, 1H), 1.00-0.94 (m, 6H), 0.94-0.86 (m, 4H). $^{13}$C NMR (126 MHz, THF-d$_8$) δ 134.81, 131.71, 130.28, 124.66, 120.80, 118.47, 118.18, 114.05, 112.42, 111.28, 7.91, 5.18. HRMS: [$C_{14}H_{18}NSi$] calculated 228.1213, measured 228.1208. The HSQC spectrum of this reaction product is provided in FIG. 12.

Example 6.9.11

Benzofuran-2-yltriethylsilane

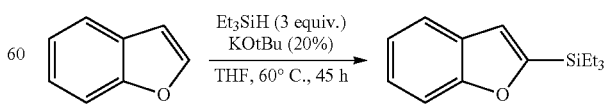

Figure 13:
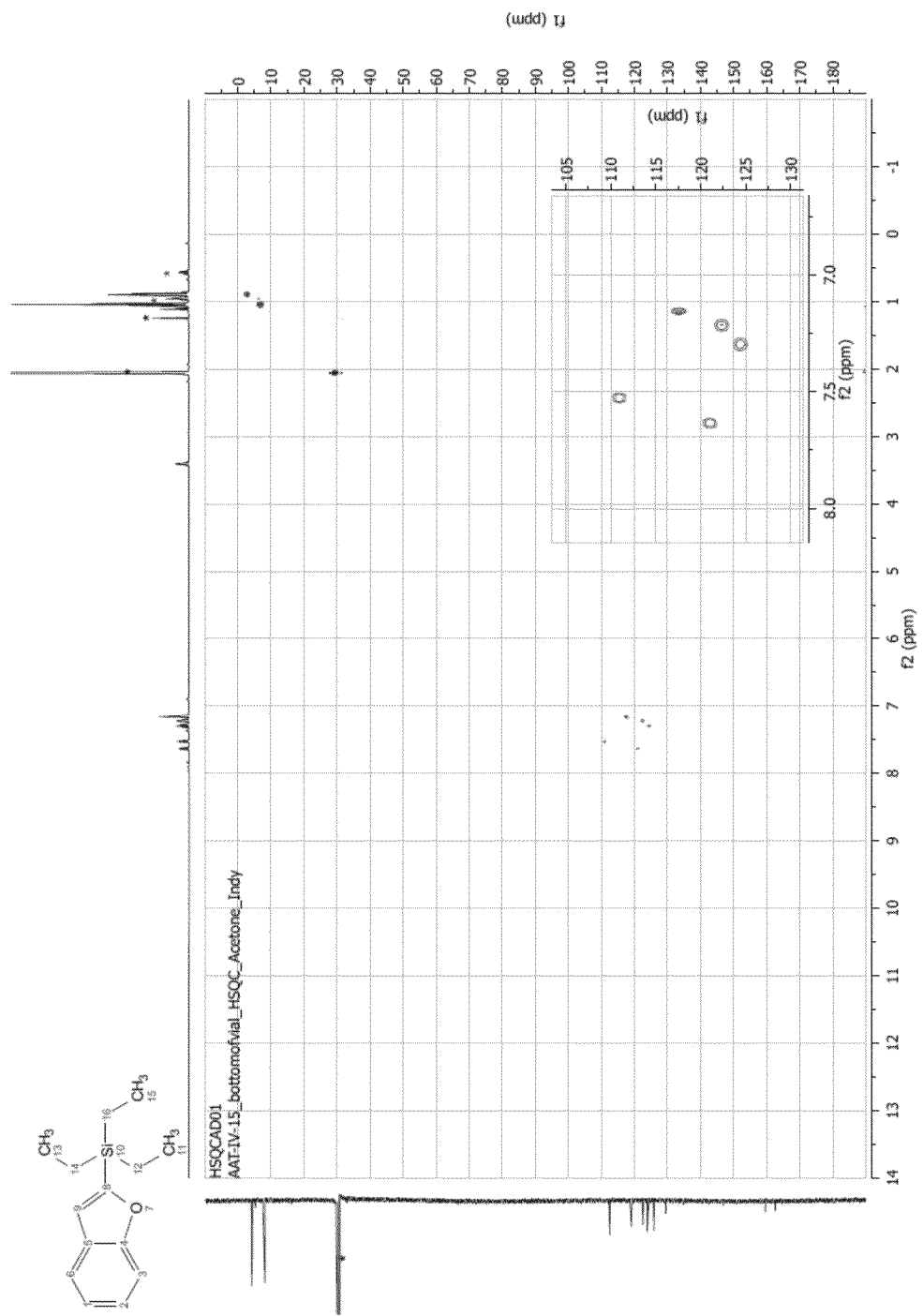

The reaction was conducted according to the General Procedure by heating benzofuran (59 mg, 0.5 mmol, 1 equiv.), KOt-Bu (19.6 mg, 0.18 mmol, 0.35 equiv.) and Et$_3$SiH (239 microliters, 1.5 mmol, 3 equiv.) in 1 mL of tetrahydrofuran for 45 hours at 60° C. After aqueous work up, the crude reaction mixture was purified by chromatography on silica eluting with hexanes (isochratic) to obtain 44 mg (38%) of the title compound as a colourless oil. $^1$H NMR (500 MHz, Acetone-d6) δ 7.64 (ddd, J=7.7, 1.3, 0.7 Hz, 1H), 7.53 (dd, J=8.2, 0.9 Hz, 1H), 7.30 (ddd, J=8.3, 7.2, 1.3 Hz, 1H), 7.22 (ddd, J=7.7, 7.2, 1.0 Hz, 1H), 7.16 (d, J=1.0 Hz, 1H), 1.09-0.98 (m, 9H), 0.92-0.84 (m, 6H). The HSQC spectrum of this reaction product as provided in FIG. 13.

Example 6.9.12

Benzo[b]thiophen-3-yltriethylsilane

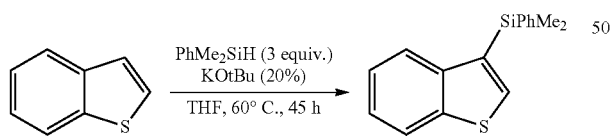

Figure 14A:
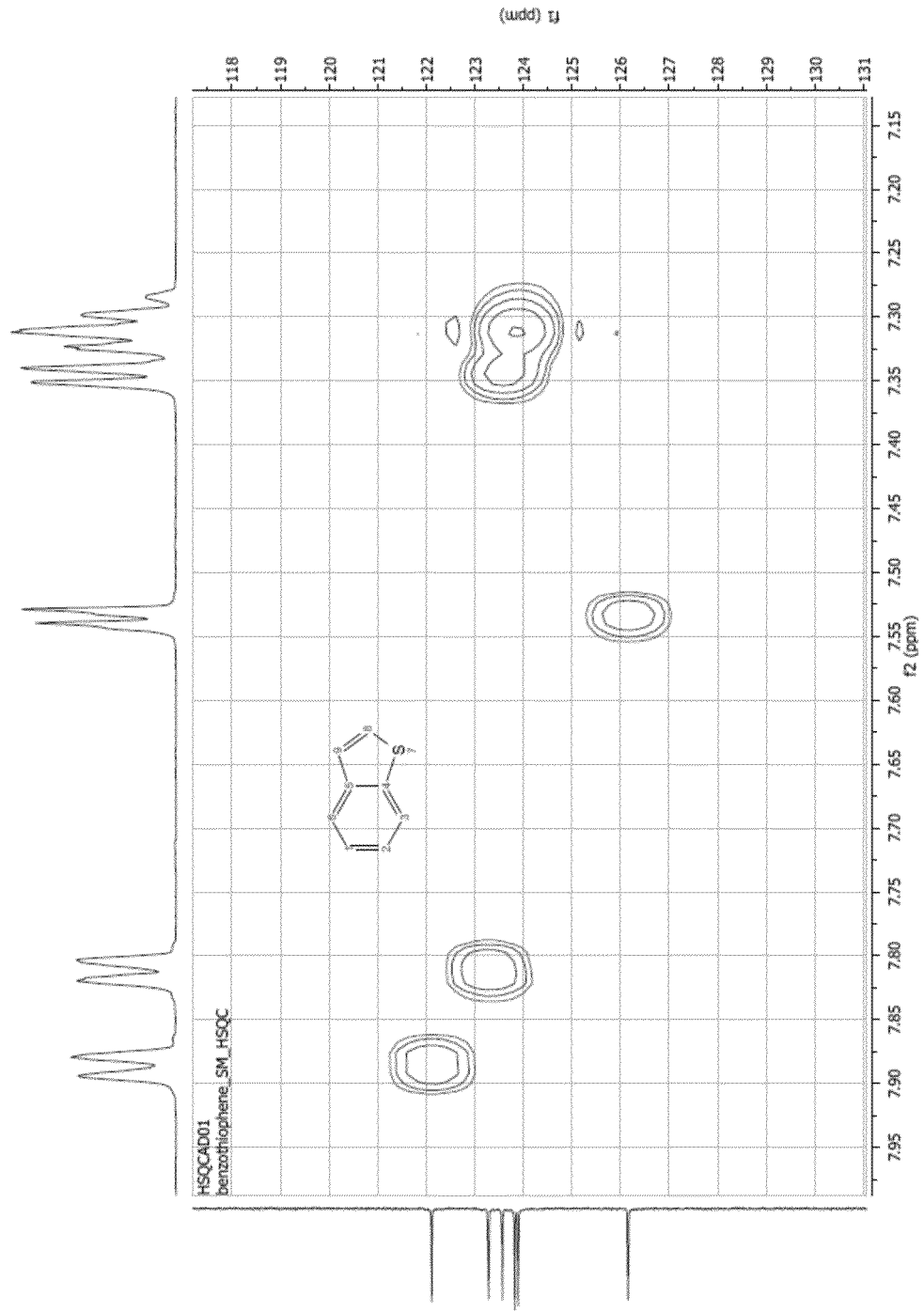
FIG. 14A-B are the HSQC spectra of (A) benzothiophene and (B) the product of its reaction with triethylsilane, as described in Example 6.9.12, characterized as benzo[b]thiophen-3-yltriethylsilane.
Figure 14B:
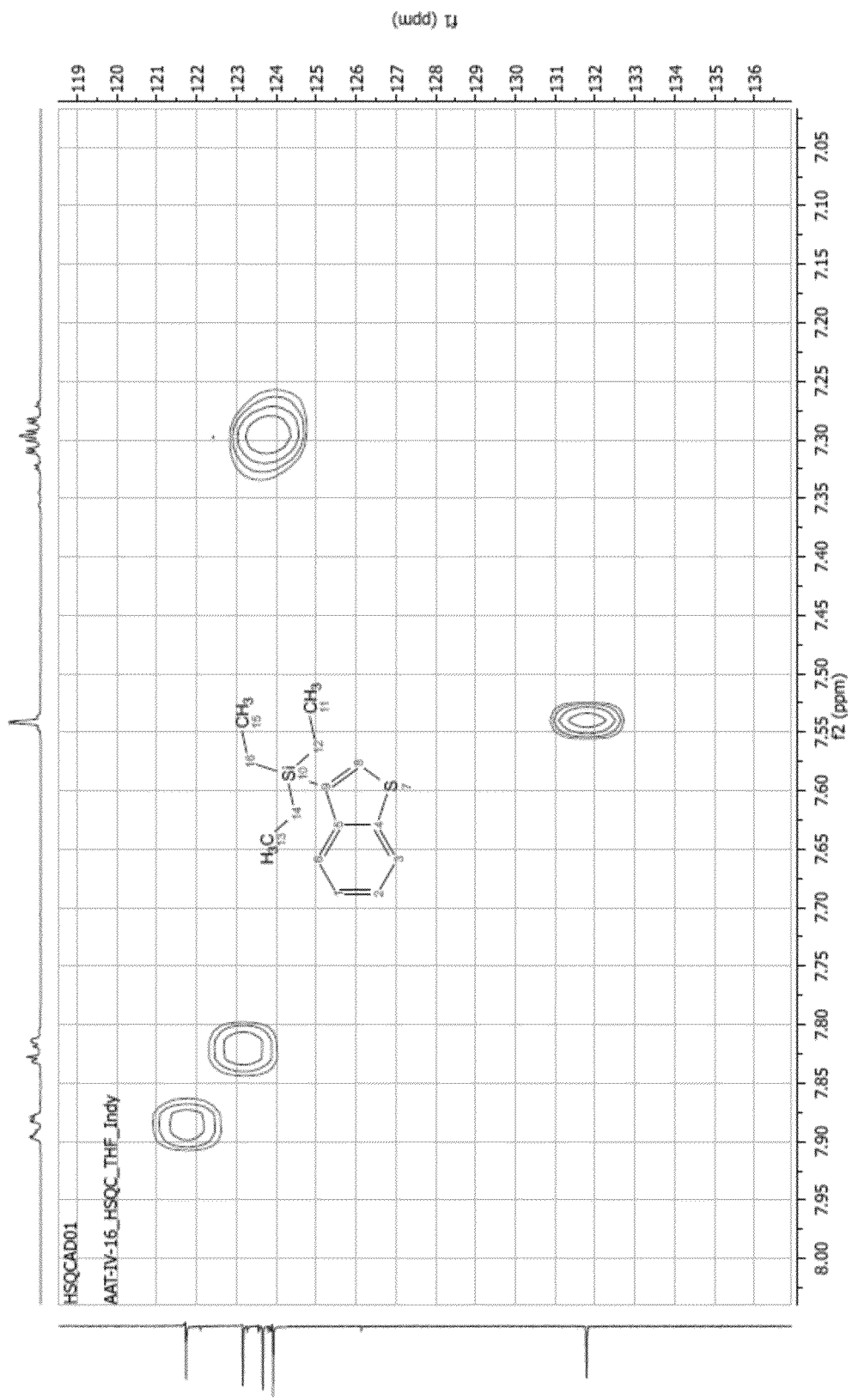

The reaction was conducted according to the General Procedure by heating thianaphthene (66 mg, 0.5 mmol, 1 equiv.), KOt-Bu (8.4 mg, 0.08 mmol, 0.15 equiv.) and Et$_3$SiH (239 microliters, 1.5 mmol, 3 equiv.) in 1 mL of tetrahydrofuran for 50 hours at 23° C. After aqueous work up, the crude reaction mixture was purified by chromatography on silica eluting with 80:2 hexanes:triethylamine to obtain 103 mg (83%) of the title compound as a colourless oil. $^1$H NMR (500 MHz, THF-d8) δ 7.90-7.85 (m, 1H), 7.84-7.76 (m, 1H), 7.53 (d, J=0.8 Hz, 1H), 7.34-7.20 (m, 2H), 1.08-0.99 (m, 9H), 0.95-0.80 (m, 6H). $^{13}$C NMR (126 MHz, THF-d8) δ 144.78, 142.34, 139.12, 132.97, 125.10, 124.84, 124.34, 122.91, 7.84, 5.10. HRMS: [C$_{14}$H$_{20}$SSi] calculated 248.1051, measured 248.1055. The HSQC spectrum of this reaction product as provided in FIG. 14.

Example 6.9.13

Benzo[b]thiophen-3-yldimethyl(phenyl)silane

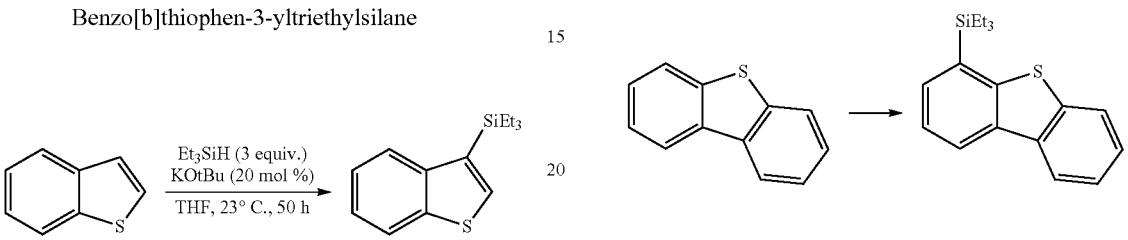

The reaction was conducted according to the General Procedure by heating thianaphthene (66 mg, 0.5 mmol, 1 equiv.), KOt-Bu (8.4 mg, 0.08 mmol, 0.15 equiv.) and PhMe$_2$SiH (239 microliters, 1.5 mmol, 3 equiv.) in 1 mL of tetrahydrofuran for 48 hours at 65° C. After aqueous work up, the crude reaction mixture was purified by chromatography on silica eluting with hexanes (isochratic) to obtain 102 mg (76%) of the title compound as a pale yellow oily solid. $^1$H NMR (500 MHz, CDCl$_3$) δ 7.94-7.87 (m, 1H), 7.85-7.78 (m, 1H), 7.71-7.58 (m, 2H), 7.51 (d, J=0.8 Hz, 1H), 7.46-7.39 (m, 3H), 7.38-7.30 (m, 2H), 0.69 (s, 6H). $^{13}$C NMR (126 MHz, CDCl$_3$) δ 144.01, 141.12, 140.18, 137.29, 134.13, 132.41, 129.70, 128.09, 124.45, 124.18, 123.69, 122.33, -1.42. HRMS: [C$_{16}$H$_{16}$SSi] calculated 268.0743, measured 268.0742

Example 6.9.14

Silylation of Dibenzothiophene

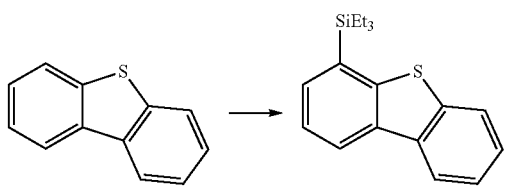

Figure 15:
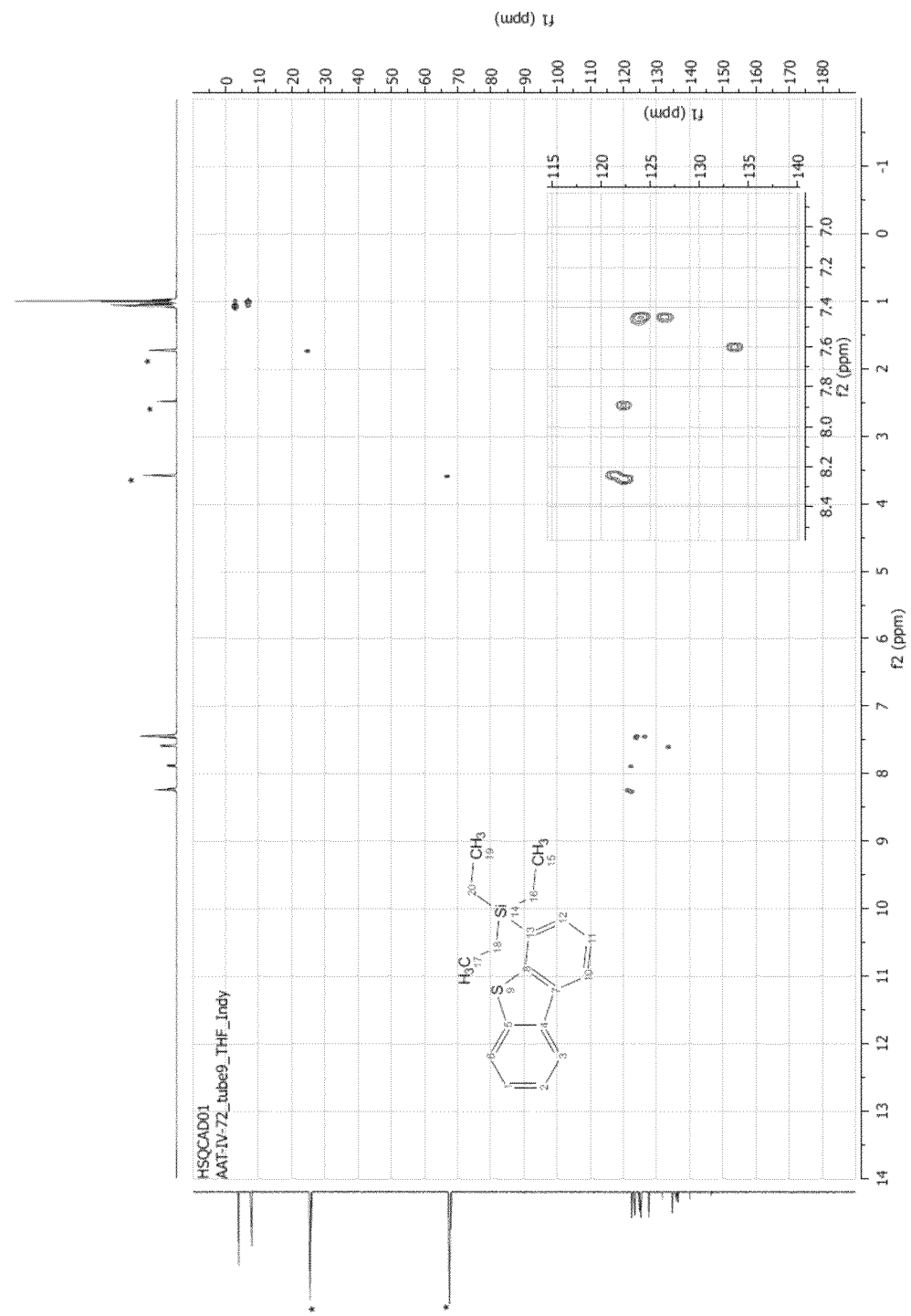

The reaction was conducted according to the General Procedure by heating dibenzothiophene (92 mg, 0.5 mmol, 1 equiv.), KOt-Bu (5.6 mg, 0.05 mmol, 0.1 equiv) and Et$_3$SiH (160 microliters, 1.0 mmol, 2 equiv.) in 1 mL of 1,4-dioxane for 14 hours at 75° C. After aqueous work up, the crude reaction mixture was purified by chromatography on silica using an 80:2 mixture of hexanes:triethylamine to obtain 51 mg (34%) of the title compound as a colourless oil. $^1$H NMR (500 MHz, THF-d$_8$) δ 8.26-8.22 (m, 2H), 7.90-7.86 (m, 1H), 7.59 (dd, J=7.1, 1.3 Hz, 1H), 7.47-7.41 (m, 3H), 1.11-1.02 (m, 6H), 1.02-0.95 (m, 9H). $^{13}$C NMR (126 MHz, THF-d$_8$) δ 146.49, 140.15, 136.57, 136.06, 134.74, 131.79, 127.63, 125.30, 124.86, 123.53, 123.39, 122.48, 7.94, 3.98. HRMS: [C$_{18}$H$_{22}$SSi] calculated 255.1205, measured 255.1206, The HSQC spectrum of this reaction product as provided in FIG. 15.

Example 6.9.15

Silylation of 2,5-dimethyl thiophene

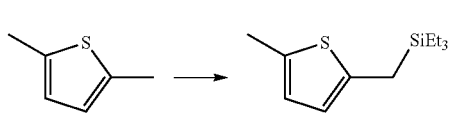

The reaction was conducted according to the General Procedure by heating 2,5,dimethyl thiophene (56 mg, 0.5 mmol, 1 equiv.), KOt-Bu (11.2 mg, 0.1 mmol, 0.2 equiv.) and Et$_3$SiH (3 equiv.) in tetrahydrofuran for 45 hours at 65° C. GC-MS of the crude product mixture yielded a mass peak associated with the monosilated derivative. $^1$H NMR data were consistent with formation of 2-methyl-5-(triethylsilylmethyl) thiophene. $^1$H NMR (500 MHz, THF-d8) δ 6.52-6.42 (m, 1H), 6.41-6.29 (m, 1H), 2.35 (s, 3H), 2.23 (s, 2H), 1.00-0.92 (m, 9H), 0.63-0.53 (m, 6H). $^{13}$C NMR (126 MHz, THF-d8) δ

140.78, 136.28, 125.96, 124.03, 15.73, 15.45, 7.97, 4.08. HRMS: [$C_{12}H_{22}SSi$] calculated 226.1212, measured 226.1220

Example 6.9.16

Silylation of Pyridine

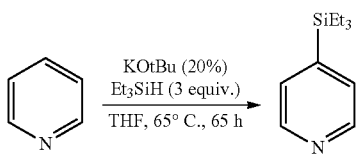

The reaction was conducted according to the General Procedure by heating pyridine (40 mg, 0.5 mmol, 1 equiv.), KOt-Bu (17 mg, 0.15 mmol, 0.3 equiv) and $Et_3SiH$ (240 microliters, 1.5 mmol, 3 equiv.) in 1 mL of tetrahydrofuran for 65 hours at 65° C. After aqueous work up, the crude reaction mixture was purified by chromatography on silica using an 80:1:4 mixture of hexanes:diethyl ether:triethylamine respectively to obtain 14 mg (15%) of the title compound as a colourless oily solid. $^1$H NMR (500 MHz, THF-$d_8$) δ 8.99-8.16 (m, 2H), 7.62-7.07 (m, 2H), 1.01-0.93 (m, 6H), 0.91-0.79 (m, 4H). $^{13}$C NMR (126 MHz, THF-$d_8$) δ 149.88, 129.76, 129.29, 7.70, 3.66. HRMS: [$C_{11}H_{20}NSi$] calculated 194.1365, measured 194.1367

Example 6.9.16

Attempted silylation of 4-methoxypyridine

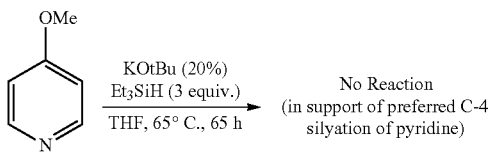

The reaction was conducted according to the General Procedure by heating 4-methoxypyridine (55 mg, 0.5 mmol, 1 equiv.), KOt-Bu (17 mg, 0.15 mmol, 0.3 equiv) and $Et_3SiH$ (240 microliters, 1.5 mmol, 3 equiv.) in 1 mL of tetrahydrofuran for 65 hours at 65° C. The reaction was diluted with diethyl ether (1 mL), quenched with water (0.5 mL) and the organic phase was analyzed by GC-MS, GC-FID and 1H NMR analysis and revealed no apparent conversion of the starting material to silylated products.

Example 6.9.17

Attempted silylation of 2,6 dimethoxypyridine

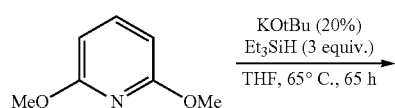

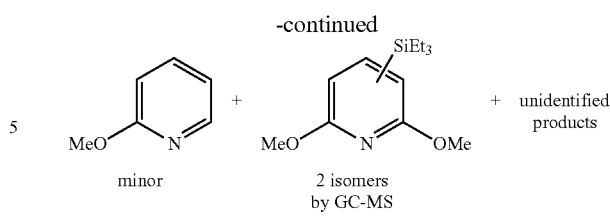

The reaction was conducted according to the General Procedure by heating 2,6-dimethoxypyridine (70 mg, 0.5 mmol, 1 equiv.), KOt-Bu (17 mg, 0.15 mmol, 0.3 equiv) and $Et_3SiH$ (240 microliters, 1.5 mmol, 3 equiv.) in 1 mL of tetrahydrofuran for 65 hours at 65° C. The reaction was diluted with diethyl ether (1 mL), quenched with water (0.5 mL) and the organic phase was analyzed by GC-MS, GC-FID and 1H NMR analysis. GC-MS analysis revealed major mass peaks corresponding to the formation of 2 silylated product isomers as well as several unidentified products.

Example 7

Evaluation of Basic Activators

The effects of various bases were evaluated under the following nominal conditions, with the results provided in Table 3:

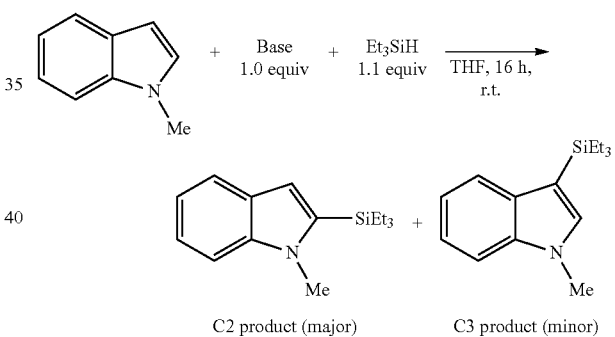

TABLE 3

Effect of bases on the silylation of N-methyl indole at ambient conditions

| Base | Yield C2 (%) | Selectivity |
|---|---|---|
| KOtBu | 66.7 | >95% |
| DABCO | 0 | — |
| KHMDS | 44 | >95% |
| LiOtBu | 0 | — |
| NaOtBu | 0 | — |
| NaOEt | 0 | — |
| KOEt | 14.2 | >95% |
| NaOAc | 0 | — |
| KOAc | 0 | — |
| KOMe | 4.6 | >95% |
| $Cs_2CO_3$ | 0 | — |
| KH | 0.1 | — |
| KOH | 0 | — |
| TBAF | 0 | — |
| KF | 0 | — |
| CsF | 0 | — |
| NaF | 0 | — |

TABLE 3-continued

Effect of bases on the silylation of
N-methyl indole at ambient conditions

| Base | Yield C2 (%) | Selectivity |
|---|---|---|
| Me₄NF | 0 | — |
| KOtBu + 18-crown-6 (1:1) | 0 | — |

Yields and selectivities calculated using GC-FID analysis with mesitylene added as a standard for quantification. C2 selectivity defined as (yield C2 product)/(yield C2 + C3 product) × 100%

As can be seen from Table 3, typical silicon activators such as fluoride salts are not competent in catalyzing the reactions described herein. TBAF, KF, CsF, Me₄NF, NaF all give no conversion of the substrate.

Interestingly, while KOR salts appear to be excellent catalysts for the silylation transformation (with KOtBu being superior to all others, and with efficiency of other potassium alkoxides correlating loosely with basicity), NaOR and LiOR where R is Me, Et, iPr, tBu all give 0% conversion. This demonstrates the critical, albeit unknown, role of the potassium cation in this reaction.

Notably, the addition of 18-crown-6 as a potassium chelator in an equimolar amount to KOtBu gives 0% conversion of the substrate under standard conditions, thus lending further support for a critical role of the potassium cation. Interestingly, other potential chelants did not inhibit, and in many cases, improved both yield and selectivity of the systems. This effect is not well understood. Without being bound by the correctness of this or any other theory, it is possible that these ligands chelated the potassium cation is proposed. Bipyridine-based ligand scaffolds as well as TMEDA (not shown) were demonstrated to be most effective in promoting high selectivity and efficiency in the silylation reaction. This is supported by the reaction with 1,7-phen, which is unable to chelate potassium, giving a lower product yield.

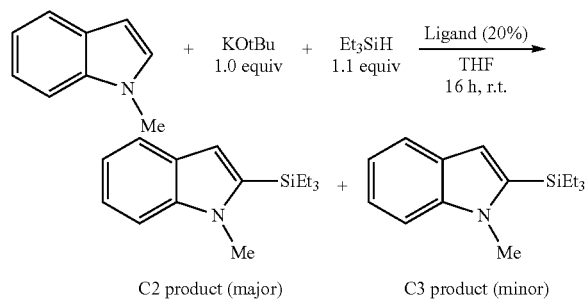

TABLE 4

Effect of bases on the silylation of
N-methyl indole at ambient conditions

| Ligand | Yield C2 | Selectivity |
|---|---|---|
| 1,10-phenanthroline | 20.7 | >95% |
| 1,7-phenanthroline | 11.4 | >95% |
| bathophenanthroline | 33.7 | >95% |
| bipyridine | 64.8 | >95% |
| 4,4'-di-t-Bu bipyridine | 60 | >95% |

Yields and selectivities calculated using GC-FID analysis with mesitylene added as a standard for quantification. C2 selectivity defined as yield (C2 product/yield C2 + C3 products) × 100%.

The activity of the inventive systems and methods were remarkably tolerant of different base loadings. In the N-methylindole model system, for example, decreasing base loading only mildly decreased efficiency. Remarkably, KOtBu even down to 1 mol % was effective and gave the major C2 product in 65% yield and a corresponding 89% C2 selectivity. This loading is even lower or equal to that required for the state-of-the-art transition-metal-based aromatic C—H silylation systems.

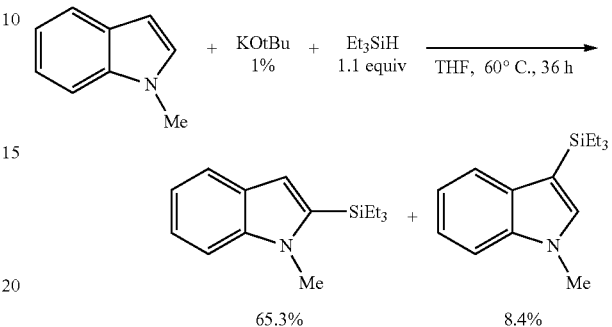

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed:

1. A chemical system for silylating aromatic substrates comprising an aromatic moiety, said system comprising a mixture of (a) at least one organosilane and (b) at least one strong hydride or alkoxide base, said system being capable of silylating the organic substrate; wherein the system is substantially free of transition-metal compounds.

2. The system of claim 1, wherein the mixture further comprises an optionally substituted tetraalkylethylenediamine (e.g., tetramethylethylenediamine), an optionally substituted 1,10-phenanthroline derivative, an optionally substituted 2,2'-bipyridine derivatives, or an optionally substituted 4-dimethylaminopyridine derivative.

3. The system of claim 1, that is substantially free of water, oxygen, or both water and oxygen.

4. The system of claim 1, wherein at least one organosilane comprises an organosilane of Formula (I) or Formula (II):

where
m is 1, 2, or 3;
n is 10 to 100; and
each R is independently optionally substituted $C_{1-12}$ alkyl or heteroalkyl, optionally substituted $C_{5-20}$ aryl or heteroaryl, optionally substituted $C_{6-30}$ alkaryl or heteroalkaryl, optionally substituted $C_{6-30}$ aralkyl or heteroaralkyl, optionally substituted —O—$C_{1-12}$ alkyl or heteroalkyl, optionally substituted —O—$C_{5-20}$ aryl or heteroaryl, optionally substituted —O—$C_{6-30}$ alkaryl or heteroalkaryl, or optionally substituted —O—$C_{6-30}$ aralkyl or heteroaralkyl, and, if substituted, the substituents may be phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents may optionally provide a tether to an insoluble or sparingly soluble support media comprising alumina, silica, or carbon.

5. The system of claim 1, wherein the organosilane is $(R)_3SiH$ or $(R)_2SiH_2$, where each R is independently $C_{1-6}$ alkyl.

6. The system of claim 1, wherein the at least one strong base comprises an alkali or alkaline earth metal hydride or alkoxide.

7. The system of claim 1, wherein the at least one strong base comprises an alkali or alkaline earth metal hydride.

8. The system of claim 7, wherein the at least one strong base comprises calcium hydride or potassium hydride.

9. The system of claim 1, wherein the at least one strong base comprises an alkali or alkaline earth metal alkoxide.

10. The system of claim 9, wherein the at least one alkoxide comprises a $C_{1-12}$ linear or branched alkyl moiety or a $C_{5-10}$ aryl or heteroaryl moiety.

11. The system of claim 10, wherein the at least one alkoxide comprises methoxide, ethoxide, propoxide, butoxide, or 2-ethyl-hexyl alkoxide.

12. The system of claim 6, wherein the alkali or alkaline earth metal hydride or alkoxide is a potassium or cesium alkoxide.

13. The system of claim 1, where the organosilane is triethylsilane and the strong base is potassium tert-butoxide.

14. The system of claim 1, wherein the organosilane and the at least one strong base are present together at a molar ratio, with respect to one another, in a range of from about 20:1 to about 1:1.

15. The system of claim 1, wherein the at least one strong base and substrate are present together at a molar ratio, with respect to one another, in a range of from about 0.01:1 to about 0.9:1.

16. The system of claim 1, wherein the organic substrate comprises an optionally substituted benzene, biphenyl, naphthalene, or anthracene ring structure.

17. The system of claim 1, wherein the organic substrate comprises an exocyclic aromatic C—X bond, where X is N, O, or S.

18. The system of claim 17, wherein the organic substrate comprises an exocyclic aromatic C—X bond and the silylation occurs ortho to the exocyclic C—X bond.

19. The system of claim 1, wherein the organic substrate comprises a heteroaryl moiety.

20. The system of claim 19, wherein the substrate comprises an optionally substituted furan, pyrrole, thiophene, pyrazole, imidazole, benzofuran, benzopyrrole, benzothiophene, indole, azaindole, dibenzofuran, xanthene, dibenzopyrrole, or a dibenzothiophene.

21. The system of claim 1, wherein the organic aromatic substrate comprises at least one of the following moieties:

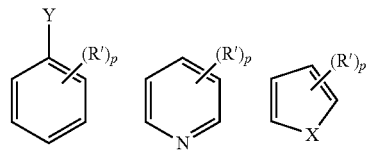

where
X is N—R", O, or S;
Y is H, N(R")$_2$, O—R", or S—R"
p is 0 to 4;
R' is a halo, hydroxyl, sulfhydryl, alkoxy, aryloxy, aralkyloxy, alkaryloxy, acyl, acyloxy), alkoxycarbonyl, aryloxycarbonyl, halocarbonyl, alkylcarbonato, arylcarbonato, carboxylato (—COO—), dialkyl-substituted carbamoyl, di haloalkyl-substituted carbamoyl, di aryl-substituted carbamoyl, di-alkyl-substituted thiocarbamoyl, di-aryl-substituted thiocarbamoyl, di-N-alkyl), N-aryl-substituted thiocarbamoyl, cyano, cyanato, thiocyanato, di-alkyl-substituted amino, di-aryl-substituted amino, arylimino (—CR═N(aryl), where R═alkyl, aryl, alkaryl, aralkyl), nitro, nitroso, alkylsulfanyl, arylsulfanyl, alkylsulfinyl, arylsulfinyl, alkylsulfonyl, boronato (—B(OR)$_2$ where R is alkyl or other hydrocarbyl); or (R')$_p$ is an optionally substituted fused alicyclic, heteroalicyclic, aryl or heteroaryl moiety; and
R" is an amine protecting group or an optionally substituted alkyl, aryl, heteroaryl, alkaryl or alk-heteroaryl, preferably optionally substituted $C_1$-$C_6$ alkyl, phenyl, tolyl, benzyl, or phenethyl.

22. The system of claim 1, wherein the substrate comprises at least one of the following moieties:

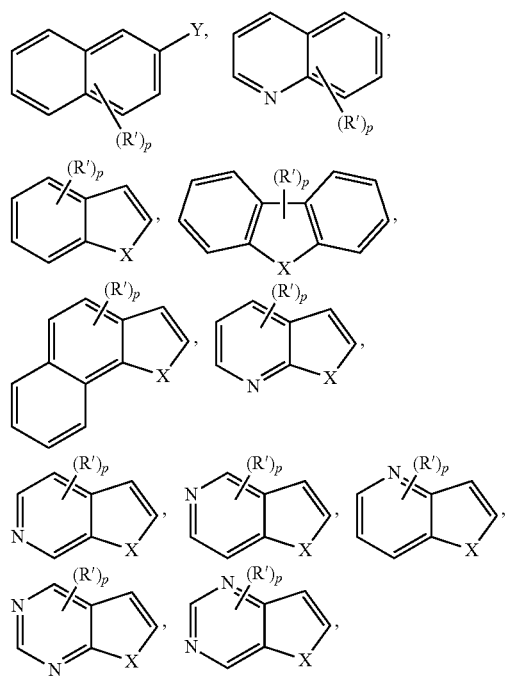

-continued

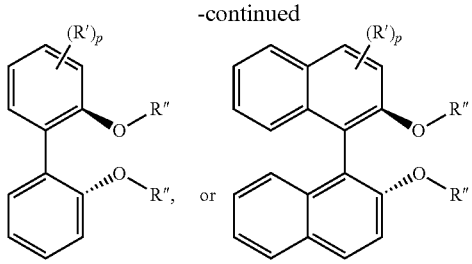

where
X is N—R", O, or S;
Y is H, N(R")₂, O—R", or S—R"
p is 0 to 4;
R' is a halo, hydroxyl, sulfhydryl, alkoxy, aryloxy, aralkyloxy, alkaryloxy, acyl, acyloxy), alkoxycarbonyl, aryloxycarbonyl, halocarbonyl, alkylcarbonato, arylcarbonato, carboxylato (—COO—), dialkyl-substituted carbamoyl, di haloalkyl-substituted carbamoyl, di aryl-substituted carbamoyl, di-alkyl-substituted thiocarbamoyl, di-aryl-substituted thiocarbamoyl, di-N-alkyl), N-aryl-substituted thiocarbamoyl, cyano, cyanato, thiocyanato, di-alkyl-substituted amino, di-aryl-substituted amino, arylimino (—CR=N(aryl), where R=alkyl, aryl, alkaryl, aralkyl), nitro, nitroso, alkylsulfanyl, arylsulfanyl, alkylsulfinyl, arylsulfinyl, alkylsulfonyl, boronato (—B(OR)₂ where R is alkyl or other hydrocarbyl); or (R')$_p$ is an optionally substituted fused alicyclic, heteroalicyclic, aryl or heteroaryl moiety; and
R" is an amine protecting group or an optionally substituted alkyl, aryl, heteroaryl, alkaryl or alk-heteroaryl, preferably optionally substituted $C_1$-$C_6$ alkyl, phenyl, tolyl, benzyl, or phenethyl.

23. The system of claim 21, wherein the organic substrate comprises a heteroaryl moiety of structure:

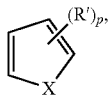

and the silylation occurs at the C-2 position of the heteroaryl ring.

24. The system of claim 21, wherein the organic substrate comprises a heteroaryl moiety of structure:

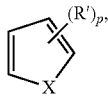

and the silylation occurs at the C-3 position of the heteroaryl ring.

25. The system of claim 1, wherein the aromatic substrate comprises at least one alpha-methyl or methylene C—H bond, said method resulting in the formation of an alpha silane.

26. The system of claim 1, wherein the aromatic substrate is polymeric.

27. The system of claim 1,
wherein said mixture and substrate are substantially free of transition-metal compounds;
wherein said mixture and substrate are substantially free of water, oxygen, or both water and oxygen;
wherein the at least one organosilane comprises an organosilane of Formula (I) or Formula (II):

$$(R)_{4-m}Si(H)_m \qquad (I)$$

$$R—[—SiH(R)—O—]_n—R \qquad (II)$$

where
m is 1, 2, or 3;
n is 10 to 100; and
each R is independently optionally substituted $C_{1-12}$ alkyl or heteroalkyl, optionally substituted $C_{5-20}$ aryl or heteroaryl, optionally substituted $C_{6-30}$ alkaryl or heteroalkaryl, optionally substituted $C_{6-30}$ aralkyl or heteroaralkyl, optionally substituted —O—$C_{1-12}$ alkyl or heteroalkyl, optionally substituted —O—$C_{5-20}$ aryl or heteroaryl, optionally substituted —O—$C_{6-30}$ alkaryl or heteroalkaryl, or optionally substituted —O—$C_{6-30}$ aralkyl or heteroaralkyl, and, if substituted, the substituents may be phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents may optionally provide a tether to an insoluble or sparingly soluble support media comprising alumina, silica, or carbon;
wherein the at least one strong base comprises:
(a) an alkali or alkaline earth metal hydride; or
(b) an alkali or alkaline earth metal alkoxide; or
(c) A combination thereof.

28. The system of claim 27, wherein the organosilane is $(R)_3SiH$ or $(R)_2SiH_2$, where each R is independently $C_{1-6}$ alkyl.

29. The system of claim 27, wherein the at least one strong base comprises an alkali or alkaline earth metal alkoxide, said alkali or alkaline earth metal comprising potassium or cesium, said alkoxide comprising tert-butoxide, or 2-ethylhexyl alkoxide.

* * * * *